(12) United States Patent
Borgel born Botbol et al.

(10) Patent No.: US 8,741,844 B2
(45) Date of Patent: Jun. 3, 2014

(54) USE OF MUTATED ANTITHROMBINS FOR TREATING OR PREVENTING COAGULATION DISORDERS

(75) Inventors: Delphine Borgel born Botbol, Paris (FR); Veronique Ferger born Picard, Sceaux (FR); Elsa Bianchini, Villeborn sur Yvette (FR)

(73) Assignee: Universite Paris-Sud XI, Orsay (FR)

( * ) Notice: Subject to any disclaimer, the term of this patent is extended or adjusted under 35 U.S.C. 154(b) by 514 days.

(21) Appl. No.: 12/669,855

(22) PCT Filed: Jul. 18, 2008

(86) PCT No.: PCT/EP2008/059486
§ 371 (c)(1),
(2), (4) Date: May 21, 2010

(87) PCT Pub. No.: WO2009/013251
PCT Pub. Date: Jan. 29, 2009

(65) Prior Publication Data
US 2010/0298224 A1    Nov. 25, 2010

(30) Foreign Application Priority Data
Jul. 20, 2007 (EP) .................................. 07290913

(51) Int. Cl.
*A61K 38/36* (2006.01)
*C07K 14/745* (2006.01)

(52) U.S. Cl.
CPC .............. *A61K 38/36* (2013.01); *C07K 14/745* (2013.01)
USPC ......... 514/13.7; 514/13.5; 514/21.2; 530/381

(58) Field of Classification Search
None
See application file for complete search history.

(56) References Cited

U.S. PATENT DOCUMENTS 5,618,713 A * 4/1997 Zettlmeissl et al. .......... 435/226

FOREIGN PATENT DOCUMENTS

WO            00/69256 A    11/2000

OTHER PUBLICATIONS

Devraj-Kizuk R. et al; "Antithrombin-III-Hamilton: a gene with a point mutation (guanine to adenine) in coden 382 causing impaired serine protease reactivity." Blood (1988) 72(5) p. 1518-1523.*
Wiebe, Ericka M. et al; "Mechanism of catalysis of inhibitionof factor IXa by antithrombin in the presence of heparin or pentasaccharide." J. Bio. Chem. (2003) 278(37) p. 35767-35774.*
Hirsh, Jack et al; "Oral anticoagulants: mechanism of action, clinical effectiveness, and optimal therapeutic range." Chest (2001) 119 p. 8S-21S.*
Watton, Jane et al; "Heparin binding affinity of normal and genetically modified antithrombin III measured using a monoclonal antibody to the heparin binding site of antithrombin III." Biochemistry (1993) 32 p. 7286-7293.*
Owen, Maurice C. et al; "Antithrombin Glasgow, 393 arg to his: A p1 reactive site variant with increased heparin affinity but no thrombin inhibitory activity." FEBS letters, (1988) 231(2) p. 317-320.*
Austin, Richard C. et al; "Site directed mutagenesis of alanine-382 of human antithrombin III." FEBS letters, (1991) 280(2) p. 254-258.*
Bock, Susan Clark et al; "Antithrombin III Utah: Proline-407 to leucine mutation in a highly conserved region near the inhibitor reactive site." Biochemistry (1988) 6171-6178.*
Seremetis S. et al; "Human recombinant DNA-derived antihaemophilic factor (factor VIII) in the treatment of haemophilia A: Conclusions of a 5 year study of home therapy." Haemophilia (1999) 5 p. 9-16.*
Portmann, A Frank and Holden, William D.; "Protamine (salmine) sulphate, heparin, and blood coagulation." J. Clin. Invest. (1949) 6(2) p. 1451-1458.*
Sharath, Murali D. et al; "Protamine induced fatal anaphylaxis." J. Thorac. Cardiovasc Surg. (1985) 90 p. 86-90.*
Bjork, Ingemar et al; "The active site of antithrombin." J. Bio. Chem. (1982) 257(5) p. 2406-2411.*
Ridker, Paul M et al; "Mutation in the gene coding for coagulation factor V and the risk of myocardial infarction, stroke, and venous thrombosis in apparently healthy men." NEJM (1995) 332 p. 912-7.*
Mauney, Michael C. et al; "Stroke rate is markedly reduced after carotid endoarterectomy by avoidance of protamine." J. Vasc. Surg. (1995) 22 p. 264-70.*
Mokdad, Ali H. et al, "Actual causes of death in the United States, 2000." JAMA (2004) 291(10) p. 1238-1245.*
Protamine sulfate drug information, www.drugs.com/mmx/protamine-sulfate.html, last revised May 18, 1999.*
Erdjument H et. al: "Antithrombin Chicago, amino acid substitution of arginine 393 to histidine." Thrombosis Research Jun. 15, 1989, pp. 613-619, vol. 54, No. 6, XP002471663.
Devraj-Kizuk R et al: "Antithrombin-III-Hamilton: a gene with a point mutation (guanine to adenine) in codon 382 causing impaired serine protease reactivity." Blood Nov. 1988, pp. 1518-1523, vol. 72, No. 5, XP002471664.
Desai Umesh R: "New antithrombin-based anticoagulants." Medicinal Research Reviews, Mar. 2004, pp. 151-181, vol. 24, No. 2, XP002471665.
Jairajpuri Mohamad Aman etal: "Elimination of PI arginine 393 interaction with underlying glutamic acid 255 partially activates antithrombin III for thrombin inhibition but not factor Xa inhibition." The Journal of Biological Chemistryy, Jul. 5, 2002, pp. 24460-24465, vol. 277, No. 27, XP002471666.
International Search Report in Corresponding Application No. PCT/EP2008/059486 Dated Oct. 28, 2008.
European Search Report in Corresponding Application No. EP07290913 Dated Mar. 6, 2008.

* cited by examiner

*Primary Examiner* — James H Alstrum Acevedo
*Assistant Examiner* — Fred Reynolds
(74) *Attorney, Agent, or Firm* — Young & Thompson

(57) ABSTRACT

Use of a mutated antithrombin having substantially no activity, in particular no anticoagulant activity, possibly in association with an anticoagulant, for the preparation of a drug intended for the prevention or treatment of pathologies linked to or associated with coagulation disorders.

16 Claims, 6 Drawing Sheets

SEQUENCE LISTING

```
<160> NUMBER OF SEQ ID NOS: 60

<210> SEQ ID NO 1
<211> LENGTH: 1387
<212> TYPE: DNA
<213> ORGANISM: Homo sapiens
<220> FEATURE:
<221> NAME/KEY: CDS
<222> LOCATION: (1)..(1296)

<400> SEQUENCE: 1 cac ggg agc cct gtg gac atc tgc aca gcc aag ccg cgg gac att ccc        48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag        96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc       144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag       192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc       240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat       288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct       336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc       384
Glu Lys Thr Ser Asp Gln Ile His Phe Phe Phe Ala Lys Leu Asn Cys
        115                 120                 125
```

```
cga ctc tat cga aaa gcc aac aaa tcc tcc aag tta gta tca gcc aat       432
Arg Leu Tyr Arg Lys Ala Asn Lys Ser Ser Lys Leu Val Ser Ala Asn
        130                 135                 140 cgc ctt ttt gga gac aaa tcc ctt acc ttc aat gag acc tac cag gac       480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag       528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat       576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat       624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg       672
Glu Leu Thr Val Leu Val Leu Val Asn Thr Ile Tyr Phe Lys Gly Leu
210                 215                 220 tgg aag tca aag ttc agc cct gag aac aca agg aag gaa ctg ttc tac       720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc       768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg       816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct       864
Pro Phe Lys Gly Asp Asp Ile Thr Met Val Leu Ile Leu Pro Lys Pro
        275                 280                 285 gag aag agc ctg gcc aag gta gag aag gaa ctc acc cca gag gtg ctg       912
Glu Lys Ser Leu Ala Lys Val Glu Lys Glu Leu Thr Pro Glu Val Leu
290                 295                 300 caa gag tgg ctg gat gaa ttg gag gag atg atg ctg gtg gtc cac atg       960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa      1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca      1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc      1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca      1152
His Lys Ala Phe Leu Glu Val Asn Glu Glu Gly Ser Glu Ala Ala Ala
370                 375                 380 agt acc gct gtt gtg att gct ggc cgt tcg cta aac ccc aac agg gtg      1200
Ser Thr Ala Val Val Ile Ala Gly Arg Ser Leu Asn Pro Asn Arg Val
385                 390                 395                 400 act ttc aag gcc aac agg cct ttc ctg gtt ttt ata aga gaa gtt cct      1248
Thr Phe Lys Ala Asn Arg Pro Phe Leu Val Phe Ile Arg Glu Val Pro
                405                 410                 415 ctg aac act att atc ttc atg ggc aga gta gcc aac cct tgt gtt aag      1296
Leu Asn Thr Ile Ile Phe Met Gly Arg Val Ala Asn Pro Cys Val Lys
            420                 425                 430 taaaatgttc ttattctttg cacctcttcc tattttggt tgtgaacag aagtaaaaat      1356 aaatacaaac tacttccatc tcacattaaa a                                   1387
```

<210> SEQ ID NO 2
<211> LENGTH: 432
<212> TYPE: PRT
<213> ORGANISM: Homo sapiens

<400> SEQUENCE: 2

```
His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Asn Lys Ser Ser Lys Leu Val Ser Ala Asn
130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380
```

| | | | | | | | | | | | | | | | |
|---|---|---|---|---|---|---|---|---|---|---|---|---|---|---|---|
|Ser|Thr|Ala|Val|Val|Ile|Ala|Gly|Arg|Ser|Leu|Asn|Pro|Asn|Arg|Val|
|385| | | |390| | | |395| | | |400| | | |

| | | | | | | | | | | | | | | |
|---|---|---|---|---|---|---|---|---|---|---|---|---|---|---|
|Thr|Phe|Lys|Ala|Asn|Arg|Pro|Phe|Leu|Val|Phe|Ile|Arg|Glu|Val|Pro|
| | | | |405| | | |410| | | |415| | |

| | | | | | | | | | | | | | | |
|---|---|---|---|---|---|---|---|---|---|---|---|---|---|---|
|Leu|Asn|Thr|Ile|Ile|Phe|Met|Gly|Arg|Val|Ala|Asn|Pro|Cys|Val|Lys|
| | | |420| | | |425| | | |430| | | |

```
<210> SEQ ID NO 3
<211> LENGTH: 1387
<212> TYPE: DNA
<213> ORGANISM: Homo sapiens
<220> FEATURE:
<221> NAME/KEY: CDS
<222> LOCATION: (1)..(1296)

<400> SEQUENCE: 3
```

| | | | | | | | | | | | | | | | |
|---|---|---|---|---|---|---|---|---|---|---|---|---|---|---|---|
|cac|ggg|agc|cct|gtg|gac|atc|tgc|aca|gcc|aag|ccg|cgg|gac|att|ccc| 48
|His|Gly|Ser|Pro|Val|Asp|Ile|Cys|Thr|Ala|Lys|Pro|Arg|Asp|Ile|Pro|
|1| | | |5| | | |10| | | |15| | | |

|atg|aat|ccc|atg|tgc|att|tac|cgc|tcc|ccg|gag|aag|aag|gca|act|gag| 96
|Met|Asn|Pro|Met|Cys|Ile|Tyr|Arg|Ser|Pro|Glu|Lys|Lys|Ala|Thr|Glu|
| | | |20| | | |25| | | |30| | | | |

|gat|gag|ggc|tca|gaa|cag|aag|atc|ccg|gag|gcc|acc|aac|cgg|cgt|gtc| 144
|Asp|Glu|Gly|Ser|Glu|Gln|Lys|Ile|Pro|Glu|Ala|Thr|Asn|Arg|Arg|Val|
| | |35| | | |40| | | |45| | | | | |

|tgg|gaa|ctg|tcc|aag|gcc|aat|tcc|cgc|ttt|gct|acc|act|ttc|tat|cag| 192
|Trp|Glu|Leu|Ser|Lys|Ala|Asn|Ser|Arg|Phe|Ala|Thr|Thr|Phe|Tyr|Gln|
| |50| | | |55| | | |60| | | | | | |

|cac|ctg|gca|gat|tcc|aag|aat|gac|aat|gat|aac|att|ttc|ctg|tca|ccc| 240
|His|Leu|Ala|Asp|Ser|Lys|Asn|Asp|Asn|Asp|Asn|Ile|Phe|Leu|Ser|Pro|
|65| | | |70| | | |75| | | |80| | | |

|ctg|agt|atc|tcc|acg|gct|ttt|gct|atg|acc|aag|ctg|ggt|gcc|tgt|aat| 288
|Leu|Ser|Ile|Ser|Thr|Ala|Phe|Ala|Met|Thr|Lys|Leu|Gly|Ala|Cys|Asn|
| | | |85| | | |90| | | |95| | | | |

|gac|acc|ctc|cag|caa|ctg|atg|gag|gta|ttt|aag|ttt|gac|acc|ata|tct| 336
|Asp|Thr|Leu|Gln|Gln|Leu|Met|Glu|Val|Phe|Lys|Phe|Asp|Thr|Ile|Ser|
| | |100| | | |105| | | |110| | | | | |

|gag|aaa|aca|tct|gat|cag|atc|cac|ttc|ttc|ttt|gcc|aaa|ctg|aac|tgc| 384
|Glu|Lys|Thr|Ser|Asp|Gln|Ile|His|Phe|Phe|Phe|Ala|Lys|Leu|Asn|Cys|
| |115| | | |120| | | |125| | | | | | |

|cga|ctc|tat|cga|aaa|gcc|aac|aaa|tcc|tcc|aag|tta|gta|tca|gcc|aat| 432
|Arg|Leu|Tyr|Arg|Lys|Ala|Asn|Lys|Ser|Ser|Lys|Leu|Val|Ser|Ala|Asn|
|130| | | |135| | | |140| | | | | | | |

|cgc|ctt|ttt|gga|gac|aaa|tcc|ctt|acc|ttc|aat|gag|acc|tac|cag|gac| 480
|Arg|Leu|Phe|Gly|Asp|Lys|Ser|Leu|Thr|Phe|Asn|Glu|Thr|Tyr|Gln|Asp|
|145| | | |150| | | |155| | | |160| | | |

|atc|agt|gag|ttg|gta|tat|gga|gcc|aag|ctc|cag|ccc|ctg|gac|ttc|aag| 528
|Ile|Ser|Glu|Leu|Val|Tyr|Gly|Ala|Lys|Leu|Gln|Pro|Leu|Asp|Phe|Lys|
| | |165| | | |170| | | |175| | | | | |

|gaa|aat|gca|gag|caa|tcc|aga|gcg|gcc|atc|aac|aaa|tgg|gtg|tcc|aat| 576
|Glu|Asn|Ala|Glu|Gln|Ser|Arg|Ala|Ala|Ile|Asn|Lys|Trp|Val|Ser|Asn|
| | |180| | | |185| | | |190| | | | | |

|aag|acc|gaa|ggc|cga|atc|acc|gat|gtc|att|ccc|tcg|gaa|gcc|atc|aat| 624
|Lys|Thr|Glu|Gly|Arg|Ile|Thr|Asp|Val|Ile|Pro|Ser|Glu|Ala|Ile|Asn|
| |195| | | |200| | | |205| | | | | | |

|gag|ctc|act|gtt|ctg|gtg|ctg|gtt|aac|acc|att|tac|ttc|aag|ggc|ctg| 672
|Glu|Leu|Thr|Val|Leu|Val|Leu|Val|Asn|Thr|Ile|Tyr|Phe|Lys|Gly|Leu|
| |210| | | |215| | | |220| | | | | | |

|tgg|aag|tca|aag|ttc|agc|cct|gag|aac|aca|agg|aag|gaa|ctg|ttc|tac| 720
|Trp|Lys|Ser|Lys|Phe|Ser|Pro|Glu|Asn|Thr|Arg|Lys|Glu|Leu|Phe|Tyr|
|225| | | |230| | | |235| | | |240| | | |

-continued

| | | |
|---|---|---|
| aag gct gat gga gag tcg tgt tca gca tct atg atg tac cag gaa ggc<br>Lys Ala Asp Gly Glu Ser Cys Ser Ala Ser Met Met Tyr Gln Glu Gly<br>                            245                        250                      255 | 768 |
| aag ttc cgt tat cgg cgc gtg gct gaa ggc acc cag gtg ctt gag ttg<br>Lys Phe Arg Tyr Arg Arg Val Ala Glu Gly Thr Gln Val Leu Glu Leu<br>             260                            265                        270 | 816 |
| ccc ttc aaa ggt gat gac atc acc atg gtc ctc atc ttg ccc aag cct<br>Pro Phe Lys Gly Asp Asp Ile Thr Met Val Leu Ile Leu Pro Lys Pro<br>        275                          280                        285 | 864 |
| gag aag agc ctg gcc aag gta gag aag gaa ctc acc cca gag gtg ctg<br>Glu Lys Ser Leu Ala Lys Val Glu Lys Glu Leu Thr Pro Glu Val Leu<br>290                        295                        300 | 912 |
| caa gag tgg ctg gat gaa ttg gag gag atg atg ctg gtg gtc cac atg<br>Gln Glu Trp Leu Asp Glu Leu Glu Glu Met Met Leu Val Val His Met<br>305                      310                        315                        320 | 960 |
| ccc cgc ttc cgc att gag gac ggc ttc agt ttg aag gag cag ctg caa<br>Pro Arg Phe Arg Ile Glu Asp Gly Phe Ser Leu Lys Glu Gln Leu Gln<br>                          325                            330                        335 | 1008 |
| gac atg ggc ctt gtc gat ctg ttc agc cct gaa aag tcc aaa ctc cca<br>Asp Met Gly Leu Val Asp Leu Phe Ser Pro Glu Lys Ser Lys Leu Pro<br>        340                          345                        350 | 1056 |
| ggt att gtt gca gaa ggc cga gat gac ctc tat gtc tca gat gca ttc<br>Gly Ile Val Ala Glu Gly Arg Asp Asp Leu Tyr Val Ser Asp Ala Phe<br>                355                        360                        365 | 1104 |
| cat aag gca ttt ctt gag gta aat gaa gaa ggc agt gaa gca gct gca<br>His Lys Ala Phe Leu Glu Val Asn Glu Glu Gly Ser Glu Ala Ala Ala<br>370                        375                        380 | 1152 |
| agt acc gct gtt gtg att gct ggc cat tcg cta aac ccc aac agg gtg<br>Ser Thr Ala Val Val Ile Ala Gly His Ser Leu Asn Pro Asn Arg Val<br>385                      390                        395                        400 | 1200 |
| act ttc aag gcc aac agg cct ttc ctg gtt ttt ata aga gaa gtt cct<br>Thr Phe Lys Ala Asn Arg Pro Phe Leu Val Phe Ile Arg Glu Val Pro<br>                          405                            410                        415 | 1248 |
| ctg aac act att atc ttc atg ggc aga gta gcc aac cct tgt gtt aag<br>Leu Asn Thr Ile Ile Phe Met Gly Arg Val Ala Asn Pro Cys Val Lys<br>        420                          425                        430 | 1296 |
| taaaatgttc ttattctttg cacctcttcc tattttggt ttgtgaacag aagtaaaaat | 1356 |
| aaatacaaac tacttccatc tcacattaaa a | 1387 |

<210> SEQ ID NO 4
<211> LENGTH: 432
<212> TYPE: PRT
<213> ORGANISM: Homo sapiens

<400> SEQUENCE: 4

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser

```
                        100                 105                 110
Glu Lys Thr Ser Asp Gln Ile His Phe Phe Ala Lys Leu Asn Cys
            115                 120                 125

Arg Leu Tyr Arg Lys Ala Asn Lys Ser Ser Lys Leu Val Ser Ala Asn
            130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
            195                 200                 205

Glu Leu Thr Val Leu Val Leu Val Asn Thr Ile Tyr Phe Lys Gly Leu
            210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
            245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
            275                 280                 285

Glu Lys Ser Leu Ala Lys Val Glu Lys Glu Leu Thr Pro Glu Val Leu
            290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
            325                 330                 335

Asp Met Gly Leu Val Asp Leu Phe Ser Pro Gly Lys Ser Lys Leu Pro
            340                 345                 350

Gly Ile Val Ala Glu Gly Arg Asp Asp Leu Tyr Val Ser Asp Ala Phe
            355                 360                 365

His Lys Ala Phe Leu Glu Val Asn Glu Glu Gly Ser Glu Ala Ala Ala
            370                 375                 380

Ser Thr Ala Val Val Ile Ala Gly His Ser Leu Asn Pro Asn Arg Val
385                 390                 395                 400

Thr Phe Lys Ala Asn Arg Pro Phe Leu Val Phe Ile Arg Glu Val Pro
            405                 410                 415

Leu Asn Thr Ile Ile Phe Met Gly Arg Val Ala Asn Pro Cys Val Lys
            420                 425                 430

<210> SEQ ID NO 5
<211> LENGTH: 1390
<212> TYPE: DNA
<213> ORGANISM: Homo sapiens
<220> FEATURE:
<221> NAME/KEY: CDS
<222> LOCATION: (1)..(1299)

<400> SEQUENCE: 5 cac ggg agc cct gtg gac atc tgc aca gcc aag ccg cgg gac att ccc    48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag    96
Met Asn Pro Met Cys Ile Tyr Arg Ser Pro Glu Lys Lys Ala Thr Glu
            20                  25                  30
```

```
gat gag ggc tca gaa cag aag atc ccg gag gcc acc aac cgg cgt gtc        144
Asp Glu Gly Ser Glu Gln Lys Ile Pro Glu Ala Thr Asn Arg Arg Val
         35                  40                  45 tgg gaa ctg tcc aag gcc aat tcc cgc ttt gct acc act ttc tat cag        192
Trp Glu Leu Ser Lys Ala Asn Ser Arg Phe Ala Thr Thr Phe Tyr Gln
 50                  55                  60 cac ctg gca gat tcc aag aat gac aat gat aac att ttc ctg tca ccc        240
His Leu Ala Asp Ser Lys Asn Asp Asn Asp Asn Ile Phe Leu Ser Pro
 65                  70                  75                  80 ctg agt atc tcc acg gct ttt gct atg acc aag ctg ggt gcc tgt aat        288
Leu Ser Ile Ser Thr Ala Phe Ala Met Thr Lys Leu Gly Ala Cys Asn
                 85                  90                  95 gac acc ctc cag caa ctg atg gag gta ttt aag ttt gac acc ata tct        336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc        384
Glu Lys Thr Ser Asp Gln Ile His Phe Phe Phe Ala Lys Leu Asn Cys
        115                 120                 125 cga ctc tat cga aaa gcc aac aaa tcc tcc aag tta gta tca gcc aat        432
Arg Leu Tyr Arg Lys Ala Asn Lys Ser Ser Lys Leu Val Ser Ala Asn
    130                 135                 140 cgc ctt ttt gga gac aaa tcc ctt acc ttc aat gag acc tac cag gac        480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag        528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat        576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat        624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg        672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac        720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc        768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg        816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct        864
Pro Phe Lys Gly Asp Asp Ile Thr Met Val Leu Ile Leu Pro Lys Pro
        275                 280                 285 gag aag agc ctg gcc aag gta gag aag gaa ctc acc cca gag gtg ctg        912
Glu Lys Ser Leu Ala Lys Val Glu Lys Glu Leu Thr Pro Glu Val Leu
    290                 295                 300 caa gag tgg ctg gat gaa ttg gag gag atg atg ctg gtg gtc cac atg        960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa       1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca       1056
Asp Met Gly Leu Val Asp Leu Phe Ser Pro Glu Lys Ser Lys Leu Pro
            340                 345                 350
```

-continued

```
ggt att gtt gca gaa ggc cga gat gac ctc tat gtc tca gat gca ttc     1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca     1152
His Lys Ala Phe Leu Glu Val Asn Glu Glu Gly Ser Glu Ala Ala Ala
370                 375                 380 agt acc gct gtt gtg att gct ggc cgt cca tcg cta aac ccc aac agg     1200
Ser Thr Ala Val Val Ile Ala Gly Arg Pro Ser Leu Asn Pro Asn Arg
385                 390                 395                 400 gtg act ttc aag gcc aac agg cct ttc ctg gtt ttt ata aga gaa gtt     1248
Val Thr Phe Lys Ala Asn Arg Pro Phe Leu Val Phe Ile Arg Glu Val
                405                 410                 415 cct ctg aac act att atc ttc atg ggc aga gta gcc aac cct tgt gtt     1296
Pro Leu Asn Thr Ile Ile Phe Met Gly Arg Val Ala Asn Pro Cys Val
            420                 425                 430 aag taaaatgttc ttattctttg cacctcttcc tattttggt ttgtgaacag           1349
Lys aagtaaaaat aaatacaaac tacttccatc tcacattaaa a                       1390

<210> SEQ ID NO 6
<211> LENGTH: 433
<212> TYPE: PRT
<213> ORGANISM: Homo sapiens

<400> SEQUENCE: 6

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Asn Lys Ser Ser Lys Leu Val Ser Ala Asn
    130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
```

-continued

```
                                 245                 250                 255
Lys Phe Arg Tyr Arg Val Ala Glu Gly Thr Gln Val Leu Glu Leu
            260                 265                 270

Pro Phe Lys Gly Asp Asp Ile Thr Met Val Leu Ile Leu Pro Lys Pro
            275                 280                 285

Glu Lys Ser Leu Ala Lys Val Glu Lys Glu Leu Thr Pro Glu Val Leu
            290                 295                 300

Gln Glu Trp Leu Asp Leu Glu Glu Met Met Leu Val Val His Met
305                 310                 315                 320

Pro Arg Phe Arg Ile Glu Asp Gly Phe Ser Leu Lys Glu Gln Leu Gln
            325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
            355                 360                 365

His Lys Ala Phe Leu Glu Val Asn Glu Glu Gly Ser Glu Ala Ala Ala
            370                 375                 380

Ser Thr Ala Val Val Ile Ala Gly Arg Pro Ser Leu Asn Pro Asn Arg
385                 390                 395                 400

Val Thr Phe Lys Ala Asn Arg Pro Phe Leu Val Phe Ile Arg Glu Val
                    405                 410                 415

Pro Leu Asn Thr Ile Ile Phe Met Gly Arg Val Ala Asn Pro Cys Val
                    420                 425                 430

Lys

<210> SEQ ID NO 7
<211> LENGTH: 1384
<212> TYPE: DNA
<213> ORGANISM: Homo sapiens
<220> FEATURE:
<221> NAME/KEY: CDS
<222> LOCATION: (1)..(1293)

<400> SEQUENCE: 7 cac ggg agc cct gtg gac atc tgc aca gcc aag ccg cgg gac att ccc     48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag     96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc    144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag    192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc    240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat    288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct    336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc    384
Glu Lys Thr Ser Asp Gln Ile His Phe Phe Phe Ala Lys Leu Asn Cys
        115                 120                 125
```

```
cga ctc tat cga aaa gcc aac aaa tcc tcc aag tta gta tca gcc aat         432
Arg Leu Tyr Arg Lys Ala Asn Lys Ser Ser Lys Leu Val Ser Ala Asn
    130             135             140 cgc ctt ttt gga gac aaa tcc ctt acc ttc aat gag acc tac cag gac         480
Arg Leu Phe Gly Asp Lys Ser Leu Thr Phe Asn Glu Thr Tyr Gln Asp
145             150             155             160 atc agt gag ttg gta tat gga gcc aag ctc cag ccc ctg gac ttc aag         528
Ile Ser Glu Leu Val Tyr Gly Ala Lys Leu Gln Pro Leu Asp Phe Lys
                165             170             175 gaa aat gca gag caa tcc aga gcg gcc atc aac aaa tgg gtg tcc aat         576
Glu Asn Ala Glu Gln Ser Arg Ala Ala Ile Asn Lys Trp Val Ser Asn
        180             185             190 aag acc gaa ggc cga atc acc gat gtc att ccc tcg gaa gcc atc aat         624
Lys Thr Glu Gly Arg Ile Thr Asp Val Ile Pro Ser Glu Ala Ile Asn
            195             200             205 gag ctc act gtt ctg gtg ctg gtt aac acc att tac ttc aag ggc ctg         672
Glu Leu Thr Val Leu Val Leu Val Asn Thr Ile Tyr Phe Lys Gly Leu
    210             215             220 tgg aag tca aag ttc agc cct gag aac aca agg aag gaa ctg ttc tac         720
Trp Lys Ser Lys Phe Ser Pro Glu Asn Thr Arg Lys Glu Leu Phe Tyr
225             230             235             240 aag gct gat gga gag tcg tgt tca gca tct atg atg tac cag gaa ggc         768
Lys Ala Asp Gly Glu Ser Cys Ser Ala Ser Met Met Tyr Gln Glu Gly
                245             250             255 aag ttc cgt tat cgg cgc gtg gct gaa ggc acc cag gtg ctt gag ttg         816
Lys Phe Arg Tyr Arg Arg Val Ala Glu Gly Thr Gln Val Leu Glu Leu
        260             265             270 ccc ttc aaa ggt gat gac atc acc atg gtc ctc atc ttg ccc aag cct         864
Pro Phe Lys Gly Asp Asp Ile Thr Met Val Leu Ile Leu Pro Lys Pro
            275             280             285 gag aag agc ctg gcc aag gta gag aag gaa ctc acc cca gag gtg ctg         912
Glu Lys Ser Leu Ala Lys Val Glu Lys Glu Leu Thr Pro Glu Val Leu
    290             295             300 caa gag tgg ctg gat gaa ttg gag gag atg atg ctg gtg gtc cac atg         960
Gln Glu Trp Leu Asp Glu Leu Glu Glu Met Met Leu Val Val His Met
305             310             315             320 ccc cgc ttc cgc att gag gac ggc ttc agt ttg aag gag cag ctg caa        1008
Pro Arg Phe Arg Ile Glu Asp Gly Phe Ser Leu Lys Glu Gln Leu Gln
                325             330             335 gac atg ggc ctt gtc gat ctg ttc agc cct gaa aag tcc aaa ctc cca        1056
Asp Met Gly Leu Val Asp Leu Phe Ser Pro Glu Lys Ser Lys Leu Pro
        340             345             350 ggt att gtt gca gaa ggc cga gat gac ctc tat gtc tca gat gca ttc        1104
Gly Ile Val Ala Glu Gly Arg Asp Asp Leu Tyr Val Ser Asp Ala Phe
            355             360             365 cat aag gca ttt ctt gag gta aat gaa gaa ggc agt gaa gca gct gca        1152
His Lys Ala Phe Leu Glu Val Asn Glu Glu Gly Ser Glu Ala Ala Ala
    370             375             380 agt acc gct gtt gtg att gct ggc tcg cta aac ccc aac agg gtg act        1200
Ser Thr Ala Val Val Ile Ala Gly Ser Leu Asn Pro Asn Arg Val Thr
385             390             395             400 ttc aag gcc aac agg cct ttc ctg gtt ttt ata aga gaa gtt cct ctg        1248
Phe Lys Ala Asn Arg Pro Phe Leu Val Phe Ile Arg Glu Val Pro Leu
                405             410             415 aac act att atc ttc atg ggc aga gta gcc aac cct tgt gtt aag            1293
Asn Thr Ile Ile Phe Met Gly Arg Val Ala Asn Pro Cys Val Lys
        420             425             430 taaaatgttc ttattctttg cacctcttcc tattttggt ttgtgaacag aagtaaaaat       1353
aaatacaaac tacttccatc tcacattaaa a                                     1384
```

<210> SEQ ID NO 8
<211> LENGTH: 431
<212> TYPE: PRT
<213> ORGANISM: Homo sapiens

<400> SEQUENCE: 8

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Asn Lys Ser Ser Lys Leu Val Ser Ala Asn
    130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

-continued

```
Ser Thr Ala Val Val Ile Ala Gly Ser Leu Asn Pro Asn Arg Val Thr
385                 390                 395                 400

Phe Lys Ala Asn Arg Pro Phe Leu Val Phe Ile Arg Glu Val Pro Leu
                405                 410                 415

Asn Thr Ile Ile Phe Met Gly Arg Val Ala Asn Pro Cys Val Lys
            420                 425                 430
```

<210> SEQ ID NO 9
<211> LENGTH: 1384
<212> TYPE: DNA
<213> ORGANISM: Homo sapiens
<220> FEATURE:
<221> NAME/KEY: CDS
<222> LOCATION: (1)..(1293)

<400> SEQUENCE: 9

```
cac ggg agc cct gtg gac atc tgc aca gcc aag ccg cgg gac att ccc       48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag       96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc      144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag      192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc      240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat      288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct      336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc      384
Glu Lys Thr Ser Asp Gln Ile His Phe Phe Phe Ala Lys Leu Asn Cys
        115                 120                 125 cga ctc tat cga aaa gcc aac aaa tcc tcc aag tta gta tca gcc aat      432
Arg Leu Tyr Arg Lys Ala Asn Lys Ser Ser Lys Leu Val Ser Ala Asn
    130                 135                 140 cgc ctt ttt gga gac aaa tcc ctt acc ttc aat gag acc tac cag gac      480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag      528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat      576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat      624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg      672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac      720
Trp Lys Ser Lys Phe Ser Pro Glu Asn Thr Arg Lys Glu Leu Phe Tyr
225                 230                 235                 240
```

```
aag gct gat gga gag tcg tgt tca gca tct atg atg tac cag gaa ggc    768
Lys Ala Asp Gly Glu Ser Cys Ser Ala Ser Met Met Tyr Gln Glu Gly
            245                 250                 255 aag ttc cgt tat cgg cgc gtg gct gaa ggc acc cag gtg ctt gag ttg    816
Lys Phe Arg Tyr Arg Arg Val Ala Glu Gly Thr Gln Val Leu Glu Leu
        260                 265                 270 ccc ttc aaa ggt gat gac atc acc atg gtc ctc atc ttg ccc aag cct    864
Pro Phe Lys Gly Asp Asp Ile Thr Met Val Leu Ile Leu Pro Lys Pro
    275                 280                 285 gag aag agc ctg gcc aag gta gag aag gaa ctc acc cca gag gtg ctg    912
Glu Lys Ser Leu Ala Lys Val Glu Lys Glu Leu Thr Pro Glu Val Leu
290                 295                 300 caa gag tgg ctg gat gaa ttg gag gag atg atg ctg gtg gtc cac atg    960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa   1008
Pro Arg Phe Arg Ile Glu Asp Gly Phe Ser Leu Lys Glu Gln Leu Gln
            325                 330                 335 gac atg ggc ctt gtc gat ctg ttc agc cct gaa aag tcc aaa ctc cca   1056
Asp Met Gly Leu Val Asp Leu Phe Ser Pro Glu Lys Ser Lys Leu Pro
        340                 345                 350 ggt att gtt gca gaa ggc cga gat gac ctc tat gtc tca gat gca ttc   1104
Gly Ile Val Ala Glu Gly Arg Asp Asp Leu Tyr Val Ser Asp Ala Phe
    355                 360                 365 cat aag gca ttt ctt gag gta aat gaa gaa ggc agt gaa gca gct gca   1152
His Lys Ala Phe Leu Glu Val Asn Glu Glu Gly Ser Glu Ala Ala Ala
370                 375                 380 agt acc gct gtt gtg att gct ggc cgt cta aac ccc aac agg gtg act   1200
Ser Thr Ala Val Val Ile Ala Gly Arg Leu Asn Pro Asn Arg Val Thr
385                 390                 395                 400 ttc aag gcc aac agg cct ttc ctg gtt ttt ata aga gaa gtt cct ctg   1248
Phe Lys Ala Asn Arg Pro Phe Leu Val Phe Ile Arg Glu Val Pro Leu
            405                 410                 415 aac act att atc ttc atg ggc aga gta gcc aac cct tgt gtt aag       1293
Asn Thr Ile Ile Phe Met Gly Arg Val Ala Asn Pro Cys Val Lys
        420                 425                 430 taaaatgttc ttattctttg cacctcttcc tattttggt ttgtgaacag aagtaaaaat   1353
aaatacaaac tacttccatc tcacattaaa a                                1384

<210> SEQ ID NO 10
<211> LENGTH: 431
<212> TYPE: PRT
<213> ORGANISM: Homo sapiens

<400> SEQUENCE: 10

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110
```

```
Glu Lys Thr Ser Asp Gln Ile His Phe Phe Ala Lys Leu Asn Cys
            115                 120                 125
Arg Leu Tyr Arg Lys Ala Asn Lys Ser Ser Lys Leu Val Ser Ala Asn
130                 135                 140
Arg Leu Phe Gly Asp Lys Ser Leu Thr Phe Asn Glu Thr Tyr Gln Asp
145                 150                 155                 160
Ile Ser Glu Leu Val Tyr Gly Ala Lys Leu Gln Pro Leu Asp Phe Lys
                165                 170                 175
Glu Asn Ala Glu Gln Ser Arg Ala Ala Ile Asn Lys Trp Val Ser Asn
            180                 185                 190
Lys Thr Glu Gly Arg Ile Thr Asp Val Ile Pro Ser Glu Ala Ile Asn
            195                 200                 205
Glu Leu Thr Val Leu Val Leu Val Asn Thr Ile Tyr Phe Lys Gly Leu
            210                 215                 220
Trp Lys Ser Lys Phe Ser Pro Glu Asn Thr Arg Lys Glu Leu Phe Tyr
225                 230                 235                 240
Lys Ala Asp Gly Glu Ser Cys Ser Ala Ser Met Met Tyr Gln Glu Gly
                245                 250                 255
Lys Phe Arg Tyr Arg Arg Val Ala Glu Gly Thr Gln Val Leu Glu Leu
            260                 265                 270
Pro Phe Lys Gly Asp Asp Ile Thr Met Val Leu Ile Leu Pro Lys Pro
            275                 280                 285
Glu Lys Ser Leu Ala Lys Val Glu Lys Glu Leu Thr Pro Glu Val Leu
            290                 295                 300
Gln Glu Trp Leu Asp Glu Leu Glu Glu Met Met Leu Val Val His Met
305                 310                 315                 320
Pro Arg Phe Arg Ile Glu Asp Gly Phe Ser Leu Lys Glu Gln Leu Gln
                325                 330                 335
Asp Met Gly Leu Val Asp Leu Phe Ser Pro Glu Lys Ser Lys Leu Pro
            340                 345                 350
Gly Ile Val Ala Glu Gly Arg Asp Asp Leu Tyr Val Ser Asp Ala Phe
            355                 360                 365
His Lys Ala Phe Leu Glu Val Asn Glu Glu Gly Ser Glu Ala Ala Ala
            370                 375                 380
Ser Thr Ala Val Val Ile Ala Gly Arg Leu Asn Pro Asn Arg Val Thr
385                 390                 395                 400
Phe Lys Ala Asn Arg Pro Phe Leu Val Phe Ile Arg Glu Val Pro Leu
                405                 410                 415
Asn Thr Ile Ile Phe Met Gly Arg Val Ala Asn Pro Cys Val Lys
            420                 425                 430
```

<210> SEQ ID NO 11
<211> LENGTH: 1387
<212> TYPE: DNA
<213> ORGANISM: Homo sapiens
<220> FEATURE:
<221> NAME/KEY: CDS
<222> LOCATION: (1)..(1296)

<400> SEQUENCE: 11

```
cac ggg agc cct gtg gac atc tgc aca gcc aag ccg cgg gac att ccc      48
His Gly Ser Pro Val Asp Ile Cys Thr Ala Lys Pro Arg Asp Ile Pro
1               5                  10                  15 atg aat ccc atg tgc att tac cgc tcc ccg gag aag aag gca act gag      96
Met Asn Pro Met Cys Ile Tyr Arg Ser Pro Glu Lys Lys Ala Thr Glu
                20                  25                  30
```

```
gat gag ggc tca gaa cag aag atc ccg gag gcc acc aac cgg cgt gtc        144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag        192
Trp Glu Leu Ser Lys Ala Asn Ser Arg Phe Ala Thr Thr Phe Tyr Gln
 50                  55                  60 cac ctg gca gat tcc aag aat gac aat gat aac att ttc ctg tca ccc        240
His Leu Ala Asp Ser Lys Asn Asp Asn Asp Asn Ile Phe Leu Ser Pro
 65                  70                  75                  80 ctg agt atc tcc acg gct ttt gct atg acc aag ctg ggt gcc tgt aat        288
Leu Ser Ile Ser Thr Ala Phe Ala Met Thr Lys Leu Gly Ala Cys Asn
                     85                  90                  95 gac acc ctc cag caa ctg atg gag gta ttt aag ttt gac acc ata tct        336
Asp Thr Leu Gln Gln Leu Met Glu Val Phe Lys Phe Asp Thr Ile Ser
        100                 105                 110 gag aaa aca tct gat cag atc cac ttc ttc ttt gcc aaa ctg aac tgc        384
Glu Lys Thr Ser Asp Gln Ile His Phe Phe Phe Ala Lys Leu Asn Cys
        115                 120                 125 cga ctc tat cga aaa gcc cag aaa tcc tcc aag tta gta tca gcc aat        432
Arg Leu Tyr Arg Lys Ala Gln Lys Ser Ser Lys Leu Val Ser Ala Asn
130                 135                 140 cgc ctt ttt gga gac aaa tcc ctt acc ttc aat gag acc tac cag gac        480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag        528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat        576
Glu Asn Ala Glu Gln Ser Arg Ala Ala Ile Asn Lys Trp Val Ser Asn
                180                 185                 190 aag acc gaa ggc cga atc acc gat gtc att ccc tcg gaa gcc atc aat        624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg        672
Glu Leu Thr Val Leu Val Leu Val Asn Thr Ile Tyr Phe Lys Gly Leu
        210                 215                 220 tgg aag tca aag ttc agc cct gag aac aca agg aag gaa ctg ttc tac        720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc        768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg        816
Lys Phe Arg Tyr Arg Arg Val Ala Glu Gly Thr Gln Val Leu Glu Leu
                260                 265                 270 ccc ttc aaa ggt gat gac atc acc atg gtc ctc atc ttg ccc aag cct        864
Pro Phe Lys Gly Asp Asp Ile Thr Met Val Leu Ile Leu Pro Lys Pro
        275                 280                 285 gag aag agc ctg gcc aag gta gag aag gaa ctc acc cca gag gtg ctg        912
Glu Lys Ser Leu Ala Lys Val Glu Lys Glu Leu Thr Pro Glu Val Leu
        290                 295                 300 caa gag tgg ctg gat gaa ttg gag gag atg atg ctg gtg gtc cac atg        960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa       1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca       1056
Asp Met Gly Leu Val Asp Leu Phe Ser Pro Glu Lys Ser Lys Leu Pro
        340                 345                 350
```

```
ggt att gtt gca gaa ggc cga gat gac ctc tat gtc tca gat gca ttc      1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca      1152
His Lys Ala Phe Leu Glu Val Asn Glu Glu Gly Ser Glu Ala Ala Ala
    370                 375                 380 agt acc gct gtt gtg att gct ggc cgt tcg cta aac ccc aac agg gtg      1200
Ser Thr Ala Val Val Ile Ala Gly Arg Ser Leu Asn Pro Asn Arg Val
385                 390                 395                 400 act ttc aag gcc aac agg cct ttc ctg gtt ttt ata aga gaa gtt cct      1248
Thr Phe Lys Ala Asn Arg Pro Phe Leu Val Phe Ile Arg Glu Val Pro
                405                 410                 415 ctg aac act att atc ttc atg ggc aga gta gcc aac cct tgt gtt aag      1296
Leu Asn Thr Ile Ile Phe Met Gly Arg Val Ala Asn Pro Cys Val Lys
            420                 425                 430 taaaatgttc ttattctttg cacctcttcc tattttggt ttgtgaacag aagtaaaaat     1356
aaatacaaac tacttccatc tcacattaaa a                                   1387

<210> SEQ ID NO 12
<211> LENGTH: 432
<212> TYPE: PRT
<213> ORGANISM: Homo sapiens

<400> SEQUENCE: 12

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Gln Lys Ser Ser Lys Leu Val Ser Ala Asn
    130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255
```

```
Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly Arg Ser Leu Asn Pro Asn Arg Val
385                 390                 395                 400

Thr Phe Lys Ala Asn Arg Pro Phe Leu Val Phe Ile Arg Glu Val Pro
                405                 410                 415

Leu Asn Thr Ile Ile Phe Met Gly Arg Val Ala Asn Pro Cys Val Lys
            420                 425                 430

<210> SEQ ID NO 13
<211> LENGTH: 1387
<212> TYPE: DNA
<213> ORGANISM: Homo sapiens
<220> FEATURE:
<221> NAME/KEY: CDS
<222> LOCATION: (1)..(1296)

<400> SEQUENCE: 13 cac ggg agc cct gtg gac atc tgc aca gcc aag ccg cgg gac att ccc      48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag      96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc     144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag     192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc     240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat     288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct     336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc     384
Glu Lys Thr Ser Asp Gln Ile His Phe Phe Phe Ala Lys Leu Asn Cys
        115                 120                 125 cga ctc tat cga aaa gcc cag aaa tcc tcc aag tta gta tca gcc aat     432
Arg Leu Tyr Arg Lys Ala Gln Lys Ser Ser Lys Leu Val Ser Ala Asn
    130                 135                 140
```

| | | | | | | | | | | | | | | | | |
|---|---|---|---|---|---|---|---|---|---|---|---|---|---|---|---|---|
| cgc | ctt | ttt | gga | gac | aaa | tcc | ctt | acc | ttc | aat | gag | acc | tac | cag | gac | 480 |
| Arg | Leu | Phe | Gly | Asp | Lys | Ser | Leu | Thr | Phe | Asn | Glu | Thr | Tyr | Gln | Asp | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| atc | agt | gag | ttg | gta | tat | gga | gcc | aag | ctc | cag | ccc | ctg | gac | ttc | aag | 528 |
| Ile | Ser | Glu | Leu | Val | Tyr | Gly | Ala | Lys | Leu | Gln | Pro | Leu | Asp | Phe | Lys | |
| | | | | 165 | | | | | 170 | | | | | 175 | | |

| | | | | | | | | | | | | | | | | |
|---|---|---|---|---|---|---|---|---|---|---|---|---|---|---|---|---|
| gaa | aat | gca | gag | caa | tcc | aga | gcg | gcc | atc | aac | aaa | tgg | gtg | tcc | aat | 576 |
| Glu | Asn | Ala | Glu | Gln | Ser | Arg | Ala | Ala | Ile | Asn | Lys | Trp | Val | Ser | Asn | |
| | | 180 | | | | | 185 | | | | | 190 | | | | |

| | | | | | | | | | | | | | | | | |
|---|---|---|---|---|---|---|---|---|---|---|---|---|---|---|---|---|
| aag | acc | gaa | ggc | cga | atc | acc | gat | gtc | att | ccc | tcg | gaa | gcc | atc | aat | 624 |
| Lys | Thr | Glu | Gly | Arg | Ile | Thr | Asp | Val | Ile | Pro | Ser | Glu | Ala | Ile | Asn | |
| | | 195 | | | | | 200 | | | | | 205 | | | | |

| | | | | | | | | | | | | | | | | |
|---|---|---|---|---|---|---|---|---|---|---|---|---|---|---|---|---|
| gag | ctc | act | gtt | ctg | gtg | ctg | gtt | aac | acc | att | tac | ttc | aag | ggc | ctg | 672 |
| Glu | Leu | Thr | Val | Leu | Val | Leu | Val | Asn | Thr | Ile | Tyr | Phe | Lys | Gly | Leu | |
| 210 | | | | | 215 | | | | | 220 | | | | | | |

| | | | | | | | | | | | | | | | | |
|---|---|---|---|---|---|---|---|---|---|---|---|---|---|---|---|---|
| tgg | aag | tca | aag | ttc | agc | cct | gag | aac | aca | agg | aag | gaa | ctg | ttc | tac | 720 |
| Trp | Lys | Ser | Lys | Phe | Ser | Pro | Glu | Asn | Thr | Arg | Lys | Glu | Leu | Phe | Tyr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aag | gct | gat | gga | gag | tcg | tgt | tca | gca | tct | atg | atg | tac | cag | gaa | ggc | 768 |
| Lys | Ala | Asp | Gly | Glu | Ser | Cys | Ser | Ala | Ser | Met | Met | Tyr | Gln | Glu | Gly | |
| | | | | 245 | | | | | 250 | | | | | 255 | | |

| | | | | | | | | | | | | | | | | |
|---|---|---|---|---|---|---|---|---|---|---|---|---|---|---|---|---|
| aag | ttc | cgt | tat | cgg | cgc | gtg | gct | gaa | ggc | acc | cag | gtg | ctt | gag | ttg | 816 |
| Lys | Phe | Arg | Tyr | Arg | Arg | Val | Ala | Glu | Gly | Thr | Gln | Val | Leu | Glu | Leu | |
| | | 260 | | | | | 265 | | | | | 270 | | | | |

| | | | | | | | | | | | | | | | | |
|---|---|---|---|---|---|---|---|---|---|---|---|---|---|---|---|---|
| ccc | ttc | aaa | ggt | gat | gac | atc | acc | atg | gtc | ctc | atc | ttg | ccc | aag | cct | 864 |
| Pro | Phe | Lys | Gly | Asp | Asp | Ile | Thr | Met | Val | Leu | Ile | Leu | Pro | Lys | Pro | |
| | | 275 | | | | | 280 | | | | | 285 | | | | |

| | | | | | | | | | | | | | | | | |
|---|---|---|---|---|---|---|---|---|---|---|---|---|---|---|---|---|
| gag | aag | agc | ctg | gcc | aag | gta | gag | aag | gaa | ctc | acc | cca | gag | gtg | ctg | 912 |
| Glu | Lys | Ser | Leu | Ala | Lys | Val | Glu | Lys | Glu | Leu | Thr | Pro | Glu | Val | Leu | |
| | | 290 | | | | | 295 | | | | | 300 | | | | |

| | | | | | | | | | | | | | | | | |
|---|---|---|---|---|---|---|---|---|---|---|---|---|---|---|---|---|
| caa | gag | tgg | ctg | gat | gaa | ttg | gag | gag | atg | atg | ctg | gtg | gtc | cac | atg | 960 |
| Gln | Glu | Trp | Leu | Asp | Glu | Leu | Glu | Glu | Met | Met | Leu | Val | Val | His | Met | |
| 305 | | | | 310 | | | | | 315 | | | | | 320 | | |

| | | | | | | | | | | | | | | | | |
|---|---|---|---|---|---|---|---|---|---|---|---|---|---|---|---|---|
| ccc | cgc | ttc | cgc | att | gag | gac | ggc | ttc | agt | ttg | aag | gag | cag | ctg | caa | 1008 |
| Pro | Arg | Phe | Arg | Ile | Glu | Asp | Gly | Phe | Ser | Leu | Lys | Glu | Gln | Leu | Gln | |
| | | | | 325 | | | | | 330 | | | | | 335 | | |

| | | | | | | | | | | | | | | | | |
|---|---|---|---|---|---|---|---|---|---|---|---|---|---|---|---|---|
| gac | atg | ggc | ctt | gtc | gat | ctg | ttc | agc | cct | gaa | aag | tcc | aaa | ctc | cca | 1056 |
| Asp | Met | Gly | Leu | Val | Asp | Leu | Phe | Ser | Pro | Glu | Lys | Ser | Lys | Leu | Pro | |
| | | | | 340 | | | | | 345 | | | | | 350 | | |

| | | | | | | | | | | | | | | | | |
|---|---|---|---|---|---|---|---|---|---|---|---|---|---|---|---|---|
| ggt | att | gtt | gca | gaa | ggc | cga | gat | gac | ctc | tat | gtc | tca | gat | gca | ttc | 1104 |
| Gly | Ile | Val | Ala | Glu | Gly | Arg | Asp | Asp | Leu | Tyr | Val | Ser | Asp | Ala | Phe | |
| | | 355 | | | | | 360 | | | | | 365 | | | | |

| | | | | | | | | | | | | | | | | |
|---|---|---|---|---|---|---|---|---|---|---|---|---|---|---|---|---|
| cat | aag | gca | ttt | ctt | gag | gta | aat | gaa | gaa | ggc | agt | gaa | gca | gct | gca | 1152 |
| His | Lys | Ala | Phe | Leu | Glu | Val | Asn | Glu | Glu | Gly | Ser | Glu | Ala | Ala | Ala | |
| | 370 | | | | | 375 | | | | | 380 | | | | | |

| | | | | | | | | | | | | | | | | |
|---|---|---|---|---|---|---|---|---|---|---|---|---|---|---|---|---|
| agt | acc | gct | gtt | gtg | att | gct | ggc | cat | tcg | cta | aac | ccc | aac | agg | gtg | 1200 |
| Ser | Thr | Ala | Val | Val | Ile | Ala | Gly | His | Ser | Leu | Asn | Pro | Asn | Arg | Val | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| act | ttc | aag | gcc | aac | agg | cct | ttc | ctg | gtt | ttt | ata | aga | gaa | gtt | cct | 1248 |
| Thr | Phe | Lys | Ala | Asn | Arg | Pro | Phe | Leu | Val | Phe | Ile | Arg | Glu | Val | Pro | |
| | | | | 405 | | | | | 410 | | | | | 415 | | |

| | | | | | | | | | | | | | | | | |
|---|---|---|---|---|---|---|---|---|---|---|---|---|---|---|---|---|
| ctg | aac | act | att | atc | ttc | atg | ggc | aga | gta | gcc | aac | cct | tgt | gtt | aag | 1296 |
| Leu | Asn | Thr | Ile | Ile | Phe | Met | Gly | Arg | Val | Ala | Asn | Pro | Cys | Val | Lys | |
| | | | | 420 | | | | | 425 | | | | | 430 | | |

| | | | |
|---|---|---|---|
| taaaatgttc | ttattctttg | cacctcttcc | tattttggt ttgtgaacag aagtaaaaat | 1356 |
| aaatacaaac | tacttccatc | tcacattaaa | a | 1387 |

<210> SEQ ID NO 14
<211> LENGTH: 432
<212> TYPE: PRT

-continued

<213> ORGANISM: Homo sapiens

<400> SEQUENCE: 14

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Gln Lys Ser Ser Lys Leu Val Ser Ala Asn
130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly His Ser Leu Asn Pro Asn Arg Val
385                 390                 395                 400

Thr Phe Lys Ala Asn Arg Pro Phe Leu Val Phe Ile Arg Glu Val Pro

```
                    405                 410                 415
Leu Asn Thr Ile Ile Phe Met Gly Arg Val Ala Asn Pro Cys Val Lys
        420                 425                 430

<210> SEQ ID NO 15
<211> LENGTH: 1390
<212> TYPE: DNA
<213> ORGANISM: Homo sapiens
<220> FEATURE:
<221> NAME/KEY: CDS
<222> LOCATION: (1)..(1299)

<400> SEQUENCE: 15 cac ggg agc cct gtg gac atc tgc aca gcc aag ccg cgg gac att ccc      48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag      96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc     144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag     192
Trp Glu Leu Ser Lys Ala Asn Ser Arg Phe Ala Thr Thr Phe Tyr Gln
50                  55                  60 cac ctg gca gat tcc aag aat gac aat gat aac att ttc ctg tca ccc     240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat     288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct     336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc     384
Glu Lys Thr Ser Asp Gln Ile His Phe Phe Phe Ala Lys Leu Asn Cys
        115                 120                 125 cga ctc tat cga aaa gcc cag aaa tcc tcc aag tta gta tca gcc aat     432
Arg Leu Tyr Arg Lys Ala Gln Lys Ser Ser Lys Leu Val Ser Ala Asn
130                 135                 140 cgc ctt ttt gga gac aaa tcc ctt acc ttc aat gag acc tac cag gac     480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag     528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat     576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat     624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg     672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac     720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc     768
Lys Ala Asp Gly Glu Ser Cys Ser Ala Ser Met Met Tyr Gln Glu Gly
                245                 250                 255
```

| | | |
|---|---|---|
| aag ttc cgt tat cgg cgc gtg gct gaa ggc acc cag gtg ctt gag ttg<br>Lys Phe Arg Tyr Arg Arg Val Ala Glu Gly Thr Gln Val Leu Glu Leu<br>260                        265                  270 | | 816 |
| ccc ttc aaa ggt gat gac atc acc atg gtc ctc atc ttg ccc aag cct<br>Pro Phe Lys Gly Asp Asp Ile Thr Met Val Leu Ile Leu Pro Lys Pro<br>275                        280                  285 | | 864 |
| gag aag agc ctg gcc aag gta gag aag gaa ctc acc cca gag gtg ctg<br>Glu Lys Ser Leu Ala Lys Val Glu Lys Glu Leu Thr Pro Glu Val Leu<br>290                        295                  300 | | 912 |
| caa gag tgg ctg gat gaa ttg gag gag atg atg ctg gtg gtc cac atg<br>Gln Glu Trp Leu Asp Glu Leu Glu Glu Met Met Leu Val Val His Met<br>305                 310                  315                  320 | | 960 |
| ccc cgc ttc cgc att gag gac ggc ttc agt ttg aag gag cag ctg caa<br>Pro Arg Phe Arg Ile Glu Asp Gly Phe Ser Leu Lys Glu Gln Leu Gln<br>                      325                  330                  335 | | 1008 |
| gac atg ggc ctt gtc gat ctg ttc agc cct gaa aag tcc aaa ctc cca<br>Asp Met Gly Leu Val Asp Leu Phe Ser Pro Glu Lys Ser Lys Leu Pro<br>340                        345                  350 | | 1056 |
| ggt att gtt gca gaa ggc cga gat gac ctc tat gtc tca gat gca ttc<br>Gly Ile Val Ala Glu Gly Arg Asp Asp Leu Tyr Val Ser Asp Ala Phe<br>                      355                  360                  365 | | 1104 |
| cat aag gca ttt ctt gag gta aat gaa gaa ggc agt gaa gca gct gca<br>His Lys Ala Phe Leu Glu Val Asn Glu Glu Gly Ser Glu Ala Ala Ala<br>370                        375                  380 | | 1152 |
| agt acc gct gtt gtg att gct ggc cgt cca tcg cta aac ccc aac agg<br>Ser Thr Ala Val Val Ile Ala Gly Arg Pro Ser Leu Asn Pro Asn Arg<br>385                 390                  395                  400 | | 1200 |
| gtg act ttc aag gcc aac agg cct ttc ctg gtt ttt ata aga gaa gtt<br>Val Thr Phe Lys Ala Asn Arg Pro Phe Leu Val Phe Ile Arg Glu Val<br>                      405                  410                  415 | | 1248 |
| cct ctg aac act att atc ttc atg ggc aga gta gcc aac cct tgt gtt<br>Pro Leu Asn Thr Ile Ile Phe Met Gly Arg Val Ala Asn Pro Cys Val<br>420                        425                  430 | | 1296 |
| aag taaaatgttc ttattctttg caccctcttcc tattttggt ttgtgaacag<br>Lys | | 1349 |
| aagtaaaaat aaatacaaac tacttccatc tcacattaaa a | | 1390 |

<210> SEQ ID NO 16
<211> LENGTH: 433
<212> TYPE: PRT
<213> ORGANISM: Homo sapiens

<400> SEQUENCE: 16

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
                20                  25                  30

Asp Glu Gly Ser Glu Gln Lys Ile Pro Glu Ala Thr Asn Arg Arg Val
            35                  40                  45

Trp Glu Leu Ser Lys Ala Asn Ser Arg Phe Ala Thr Thr Phe Tyr Gln
        50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Gln Lys Ser Ser Lys Leu Val Ser Ala Asn
            130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly Arg Pro Ser Leu Asn Pro Asn Arg
385                 390                 395                 400

Val Thr Phe Lys Ala Asn Arg Pro Phe Leu Val Phe Ile Arg Glu Val
                405                 410                 415

Pro Leu Asn Thr Ile Ile Phe Met Gly Arg Val Ala Asn Pro Cys Val
            420                 425                 430

Lys

```
<210> SEQ ID NO 17
<211> LENGTH: 1381
<212> TYPE: DNA
<213> ORGANISM: Homo sapiens
<220> FEATURE:
<221> NAME/KEY: CDS
<222> LOCATION: (1)..(1290)

<400> SEQUENCE: 17
``` cac ggg agc cct gtg gac atc tgc aca gcc aag ccg cgg gac att ccc        48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag        96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc       144

```
Asp Glu Gly Ser Glu Gln Lys Ile Pro Glu Ala Thr Asn Arg Arg Val
         35                  40                  45 tgg gaa ctg tcc aag gcc aat tcc cgc ttt gct acc act ttc tat cag    192
Trp Glu Leu Ser Lys Ala Asn Ser Arg Phe Ala Thr Thr Phe Tyr Gln
 50                  55                  60 cac ctg gca gat tcc aag aat gac aat gat aac att ttc ctg tca ccc    240
His Leu Ala Asp Ser Lys Asn Asp Asn Asp Asn Ile Phe Leu Ser Pro
 65                  70                  75                  80 ctg agt atc tcc acg gct ttt gct atg acc aag ctg ggt gcc tgt aat    288
Leu Ser Ile Ser Thr Ala Phe Ala Met Thr Lys Leu Gly Ala Cys Asn
                 85                  90                  95 gac acc ctc cag caa ctg atg gag gta ttt aag ttt gac acc ata tct    336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc    384
Glu Lys Thr Ser Asp Gln Ile His Phe Phe Phe Ala Lys Leu Asn Cys
        115                 120                 125 cga ctc tat cga aaa gcc aac aaa tcc tcc aag tta gta tca gcc aat    432
Arg Leu Tyr Arg Lys Ala Asn Lys Ser Ser Lys Leu Val Ser Ala Asn
130                 135                 140 cgc ctt ttt gga gac aaa tcc ctt acc ttc aat gag acc tac cag gac    480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag    528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat    576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat    624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg    672
Glu Leu Thr Val Leu Val Leu Val Asn Thr Ile Tyr Phe Lys Gly Leu
210                 215                 220 tgg aag tca aag ttc agc cct gag aac aca agg aag gaa ctg ttc tac    720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc    768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg    816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct    864
Pro Phe Lys Gly Asp Asp Ile Thr Met Val Leu Ile Leu Pro Lys Pro
        275                 280                 285 gag aag agc ctg gcc aag gta gag aag gaa ctc acc cca gag gtg ctg    912
Glu Lys Ser Leu Ala Lys Val Glu Lys Glu Leu Thr Pro Glu Val Leu
290                 295                 300 caa gag tgg ctg gat gaa ttg gag gag atg atg ctg gtg gtc cac atg    960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa   1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca   1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc   1104
Gly Ile Val Ala Glu Gly Arg Asp Asp Leu Tyr Val Ser Asp Ala Phe
```

-continued

```
Gly Ile Val Ala Glu Gly Arg Asp Asp Leu Tyr Val Ser Asp Ala Phe
            355                 360                 365 cat aag gca ttt ctt gag gta aat gaa gaa ggc agt gaa gca gct gca      1152
His Lys Ala Phe Leu Glu Val Asn Glu Glu Gly Ser Glu Ala Ala Ala
            370                 375                 380 agt acc gct gtt gtg att gct ggc cta aac ccc aac agg gtg act ttc      1200
Ser Thr Ala Val Val Ile Ala Gly Leu Asn Pro Asn Arg Val Thr Phe
385                 390                 395                 400 aag gcc aac agg cct ttc ctg gtt ttt ata aga gaa gtt cct ctg aac      1248
Lys Ala Asn Arg Pro Phe Leu Val Phe Ile Arg Glu Val Pro Leu Asn
                405                 410                 415 act att atc ttc atg ggc aga gta gcc aac cct tgt gtt aag               1290
Thr Ile Ile Phe Met Gly Arg Val Ala Asn Pro Cys Val Lys
            420                 425                 430 taaaatgttc ttattctttg cacctcttcc tattttggt tgtgaacag aagtaaaaat      1350 aaatacaaac tacttccatc tcacattaaa a                                   1381

<210> SEQ ID NO 18
<211> LENGTH: 430
<212> TYPE: PRT
<213> ORGANISM: Homo sapiens

<400> SEQUENCE: 18

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Asn Lys Ser Ser Lys Leu Val Ser Ala Asn
    130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
```

-continued

```
                     260                 265                 270
Pro Phe Lys Gly Asp Asp Ile Thr Met Val Leu Ile Leu Pro Lys Pro
                275                 280                 285

Glu Lys Ser Leu Ala Lys Val Glu Lys Glu Leu Thr Pro Glu Val Leu
            290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
            355                 360                 365

His Lys Ala Phe Leu Glu Val Asn Glu Glu Gly Ser Glu Ala Ala Ala
            370                 375                 380

Ser Thr Ala Val Val Ile Ala Gly Leu Asn Pro Asn Arg Val Thr Phe
385                 390                 395                 400

Lys Ala Asn Arg Pro Phe Leu Val Phe Ile Arg Glu Val Pro Leu Asn
                405                 410                 415

Thr Ile Ile Phe Met Gly Arg Val Ala Asn Pro Cys Val Lys
                420                 425                 430

<210> SEQ ID NO 19
<211> LENGTH: 1384
<212> TYPE: DNA
<213> ORGANISM: Homo sapiens
<220> FEATURE:
<221> NAME/KEY: CDS
<222> LOCATION: (1)..(1293)

<400> SEQUENCE: 19 cac ggg agc cct gtg gac atc tgc aca gcc aag ccg cgg gac att ccc      48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag      96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc     144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag     192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc     240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat     288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct     336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc     384
Glu Lys Thr Ser Asp Gln Ile His Phe Phe Phe Ala Lys Leu Asn Cys
        115                 120                 125 cga ctc tat cga aaa gcc cag aaa tcc tcc aag tta gta tca gcc aat     432
Arg Leu Tyr Arg Lys Ala Gln Lys Ser Ser Lys Leu Val Ser Ala Asn
    130                 135                 140 cgc ctt ttt gga gac aaa tcc ctt acc ttc aat gag acc tac cag gac     480
```

| | | | | | | | | | | | | | | |
|---|---|---|---|---|---|---|---|---|---|---|---|---|---|---|
| Arg | Leu | Phe | Gly | Asp | Lys | Ser | Leu | Thr | Phe | Asn | Glu | Thr | Tyr | Gln | Asp |
| 145 | | | | | 150 | | | | | 155 | | | | | 160 |

```
atc agt gag ttg gta tat gga gcc aag ctc cag ccc ctg gac ttc aag     528
Ile Ser Glu Leu Val Tyr Gly Ala Lys Leu Gln Pro Leu Asp Phe Lys
                    165                 170                 175 gaa aat gca gag caa tcc aga gcg gcc atc aac aaa tgg gtg tcc aat     576
Glu Asn Ala Glu Gln Ser Arg Ala Ala Ile Asn Lys Trp Val Ser Asn
                180                 185                 190 aag acc gaa ggc cga atc acc gat gtc att ccc tcg gaa gcc atc aat     624
Lys Thr Glu Gly Arg Ile Thr Asp Val Ile Pro Ser Glu Ala Ile Asn
            195                 200                 205 gag ctc act gtt ctg gtg ctg gtt aac acc att tac ttc aag ggc ctg     672
Glu Leu Thr Val Leu Val Leu Val Asn Thr Ile Tyr Phe Lys Gly Leu
        210                 215                 220 tgg aag tca aag ttc agc cct gag aac aca agg aag gaa ctg ttc tac     720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc     768
Lys Ala Asp Gly Glu Ser Cys Ser Ala Ser Met Met Tyr Gln Glu Gly
                    245                 250                 255 aag ttc cgt tat cgg cgc gtg gct gaa ggc acc cag gtg ctt gag ttg     816
Lys Phe Arg Tyr Arg Arg Val Ala Glu Gly Thr Gln Val Leu Glu Leu
                260                 265                 270 ccc ttc aaa ggt gat gac atc acc atg gtc ctc atc ttg ccc aag cct     864
Pro Phe Lys Gly Asp Asp Ile Thr Met Val Leu Ile Leu Pro Lys Pro
            275                 280                 285 gag aag agc ctg gcc aag gta gag aag gaa ctc acc cca gag gtg ctg     912
Glu Lys Ser Leu Ala Lys Val Glu Lys Glu Leu Thr Pro Glu Val Leu
        290                 295                 300 caa gag tgg ctg gat gaa ttg gag gag atg atg ctg gtg gtc cac atg     960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa    1008
Pro Arg Phe Arg Ile Glu Asp Gly Phe Ser Leu Lys Glu Gln Leu Gln
                    325                 330                 335 gac atg ggc ctt gtc gat ctg ttc agc cct gaa aag tcc aaa ctc cca    1056
Asp Met Gly Leu Val Asp Leu Phe Ser Pro Glu Lys Ser Lys Leu Pro
                340                 345                 350 ggt att gtt gca gaa ggc cga gat gac ctc tat gtc tca gat gca ttc    1104
Gly Ile Val Ala Glu Gly Arg Asp Asp Leu Tyr Val Ser Asp Ala Phe
            355                 360                 365 cat aag gca ttt ctt gag gta aat gaa gaa ggc agt gaa gca gct gca    1152
His Lys Ala Phe Leu Glu Val Asn Glu Glu Gly Ser Glu Ala Ala Ala
        370                 375                 380 agt acc gct gtt gtg att gct ggc tcg cta aac ccc aac agg gtg act    1200
Ser Thr Ala Val Val Ile Ala Gly Ser Leu Asn Pro Asn Arg Val Thr
385                 390                 395                 400 ttc aag gcc aac agg cct ttc ctg gtt ttt ata aga gaa gtt cct ctg    1248
Phe Lys Ala Asn Arg Pro Phe Leu Val Phe Ile Arg Glu Val Pro Leu
                    405                 410                 415 aac act att atc ttc atg ggc aga gta gcc aac cct tgt gtt aag         1293
Asn Thr Ile Ile Phe Met Gly Arg Val Ala Asn Pro Cys Val Lys
                420                 425                 430 taaaatgttc ttattctttg cacctcttcc tattttggt tgtgaacag aagtaaaaat    1353 aaatacaaac tacttccatc tcacattaaa a                                 1384

<210> SEQ ID NO 20
<211> LENGTH: 431
<212> TYPE: PRT
<213> ORGANISM: Homo sapiens
```

<400> SEQUENCE: 20

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Ala Lys Leu Asn Cys
        115                 120                 125

Arg Leu Tyr Arg Lys Ala Gln Lys Ser Ser Lys Leu Val Ser Ala Asn
130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly Ser Leu Asn Pro Asn Arg Val Thr
385                 390                 395                 400

Phe Lys Ala Asn Arg Pro Phe Leu Val Phe Ile Arg Glu Val Pro Leu
                405                 410                 415

```
Asn Thr Ile Ile Phe Met Gly Arg Val Ala Asn Pro Cys Val Lys
            420                 425                 430

<210> SEQ ID NO 21
<211> LENGTH: 1384
<212> TYPE: DNA
<213> ORGANISM: Homo sapiens
<220> FEATURE:
<221> NAME/KEY: CDS
<222> LOCATION: (1)..(1293)

<400> SEQUENCE: 21 cac ggg agc cct gtg gac atc tgc aca gcc aag ccg cgg gac att ccc        48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag        96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc       144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag       192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc       240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat       288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct       336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc       384
Glu Lys Thr Ser Asp Gln Ile His Phe Phe Phe Ala Lys Leu Asn Cys
        115                 120                 125 cga ctc tat cga aaa gcc cag aaa tcc tcc aag tta gta tca gcc aat       432
Arg Leu Tyr Arg Lys Ala Gln Lys Ser Ser Lys Leu Val Ser Ala Asn
    130                 135                 140 cgc ctt ttt gga gac aaa tcc ctt acc ttc aat gag acc tac cag gac       480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag       528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat       576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat       624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg       672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac       720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc       768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg       816
Lys Phe Arg Tyr Arg Arg Val Ala Glu Gly Thr Gln Val Leu Glu Leu
```

-continued

```
                    Lys Phe Arg Tyr Arg Arg Val Ala Glu Gly Thr Gln Val Leu Glu Leu
                                    260                 265                 270 ccc ttc aaa ggt gat gac atc acc atg gtc ctc atc ttg ccc aag cct          864
Pro Phe Lys Gly Asp Asp Ile Thr Met Val Leu Ile Leu Pro Lys Pro
            275                 280                 285 gag aag agc ctg gcc aag gta gag aag gaa ctc acc cca gag gtg ctg          912
Glu Lys Ser Leu Ala Lys Val Glu Lys Glu Leu Thr Pro Glu Val Leu
    290                 295                 300 caa gag tgg ctg gat gaa ttg gag gag atg atg ctg gtg gtc cac atg          960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa         1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca         1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc         1104
Gly Ile Val Ala Glu Gly Arg Asp Asp Leu Tyr Val Ser Asp Ala Phe
    355                 360                 365 cat aag gca ttt ctt gag gta aat gaa gaa ggc agt gaa gca gct gca         1152
His Lys Ala Phe Leu Glu Val Asn Glu Glu Gly Ser Glu Ala Ala Ala
370                 375                 380 agt acc gct gtt gtg att gct ggc cgt cta aac ccc aac agg gtg act         1200
Ser Thr Ala Val Val Ile Ala Gly Arg Leu Asn Pro Asn Arg Val Thr
385                 390                 395                 400 ttc aag gcc aac agg cct ttc ctg gtt ttt ata aga gaa gtt cct ctg         1248
Phe Lys Ala Asn Arg Pro Phe Leu Val Phe Ile Arg Glu Val Pro Leu
                405                 410                 415 aac act att atc ttc atg ggc aga gta gcc aac cct tgt gtt aag             1293
Asn Thr Ile Ile Phe Met Gly Arg Val Ala Asn Pro Cys Val Lys
            420                 425                 430 taaaatgttc ttattctttg cacctcttcc tattttggt tgtgaacag aagtaaaaat         1353 aaatacaaac tacttccatc tcacattaaa a                                      1384

<210> SEQ ID NO 22
<211> LENGTH: 431
<212> TYPE: PRT
<213> ORGANISM: Homo sapiens

<400> SEQUENCE: 22

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Gln Lys Ser Ser Lys Leu Val Ser Ala Asn
```

```
                130                 135                 140
Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly Arg Leu Asn Pro Asn Arg Val Thr
385                 390                 395                 400

Phe Lys Ala Asn Arg Pro Phe Leu Val Phe Ile Arg Glu Val Pro Leu
                405                 410                 415

Asn Thr Ile Ile Phe Met Gly Arg Val Ala Asn Pro Cys Val Lys
            420                 425                 430

<210> SEQ ID NO 23
<211> LENGTH: 1381
<212> TYPE: DNA
<213> ORGANISM: Homo sapiens
<220> FEATURE:
<221> NAME/KEY: CDS
<222> LOCATION: (1)..(1290)

<400> SEQUENCE: 23 cac ggg agc cct gtg gac atc tgc aca gcc aag ccg cgg gac att ccc      48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag      96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc     144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag     192
Trp Glu Leu Ser Lys Ala Asn Ser Arg Phe Ala Thr Thr Phe Tyr Gln
```

-continued

```
Trp Glu Leu Ser Lys Ala Asn Ser Arg Phe Ala Thr Thr Phe Tyr Gln
    50              55                  60 cac ctg gca gat tcc aag aat gac aat gat aac att ttc ctg tca ccc    240
His Leu Ala Asp Ser Lys Asn Asp Asn Asp Asn Ile Phe Leu Ser Pro
65              70                  75                  80 ctg agt atc tcc acg gct ttt gct atg acc aag ctg ggt gcc tgt aat    288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct    336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc    384
Glu Lys Thr Ser Asp Gln Ile His Phe Phe Phe Ala Lys Leu Asn Cys
        115                 120                 125 cga ctc tat cga aaa gcc cag aaa tcc tcc aag tta gta tca gcc aat    432
Arg Leu Tyr Arg Lys Ala Gln Lys Ser Ser Lys Leu Val Ser Ala Asn
    130                 135                 140 cgc ctt ttt gga gac aaa tcc ctt acc ttc aat gag acc tac cag gac    480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag    528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat    576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat    624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg    672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac    720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc    768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg    816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct    864
Pro Phe Lys Gly Asp Asp Ile Thr Met Val Leu Ile Leu Pro Lys Pro
        275                 280                 285 gag aag agc ctg gcc aag gta gag aag gaa ctc acc cca gag gtg ctg    912
Glu Lys Ser Leu Ala Lys Val Glu Lys Glu Leu Thr Pro Glu Val Leu
    290                 295                 300 caa gag tgg ctg gat gaa ttg gag gag atg atg ctg gtg gtc cac atg    960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa   1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca   1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc   1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca   1152
```

```
His Lys Ala Phe Leu Glu Val Asn Glu Glu Gly Ser Glu Ala Ala Ala
        370                 375                 380 agt acc gct gtt gtg att gct ggc cta aac ccc aac agg gtg act ttc    1200
Ser Thr Ala Val Val Ile Ala Gly Leu Asn Pro Asn Arg Val Thr Phe
385                 390                 395                 400 aag gcc aac agg cct ttc ctg gtt ttt ata aga gaa gtt cct ctg aac    1248
Lys Ala Asn Arg Pro Phe Leu Val Phe Ile Arg Glu Val Pro Leu Asn
                405                 410                 415 act att atc ttc atg ggc aga gta gcc aac cct tgt gtt aag            1290
Thr Ile Ile Phe Met Gly Arg Val Ala Asn Pro Cys Val Lys
                420                 425                 430 taaaatgttc ttattctttg cacctcttcc tattttggt ttgtgaacag aagtaaaaat    1350
aaatacaaac tacttccatc tcacattaaa a                                 1381

<210> SEQ ID NO 24
<211> LENGTH: 430
<212> TYPE: PRT
<213> ORGANISM: Homo sapiens

<400> SEQUENCE: 24

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Gln Lys Ser Ser Lys Leu Val Ser Ala Asn
    130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285
```

```
Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly Leu Asn Pro Asn Arg Val Thr Phe
385                 390                 395                 400

Lys Ala Asn Arg Pro Phe Leu Val Phe Ile Arg Glu Val Pro Leu Asn
                405                 410                 415

Thr Ile Ile Phe Met Gly Arg Val Ala Asn Pro Cys Val Lys
            420                 425                 430

<210> SEQ ID NO 25
<211> LENGTH: 1483
<212> TYPE: DNA
<213> ORGANISM: Homo sapiens
<220> FEATURE:
<221> NAME/KEY: CDS
<222> LOCATION: (1)..(1392)

<400> SEQUENCE: 25 atg tat tcc aat gtg ata gga act gta acc tct gga aaa agg aag gtt         48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt         96
Tyr Leu Leu Ser Leu Leu Leu Ile Gly Phe Trp Asp Cys Val Thr Cys
                20                  25                  30 cac ggg agc cct gtg gac atc tgc aca gcc aag ccg cgg gac att ccc        144
His Gly Ser Pro Val Asp Ile Cys Thr Ala Lys Pro Arg Asp Ile Pro
            35                  40                  45 atg aat ccc atg tgc att tac cgc tcc ccg gag aag aag gca act gag        192
Met Asn Pro Met Cys Ile Tyr Arg Ser Pro Glu Lys Lys Ala Thr Glu
        50                  55                  60 gat gag ggc tca gaa cag aag atc ccg gag gcc acc aac cgg cgt gtc        240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag        288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc        336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat        384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct        432
Asp Thr Leu Gln Gln Leu Met Glu Val Phe Lys Phe Asp Thr Ile Ser
130                 135                 140 gag aaa aca tct gat cag atc cac ttc ttc ttt gcc aaa ctg aac tgc        480
Glu Lys Thr Ser Asp Gln Ile His Phe Phe Phe Ala Lys Leu Asn Cys
145                 150                 155                 160 cga ctc tat cga aaa gcc aac aaa tcc tcc aag tta gta tca gcc aat        528
```

```
                Arg Leu Tyr Arg Lys Ala Asn Lys Ser Ser Lys Leu Val Ser Ala Asn
                                165                 170                 175 cgc ctt ttt gga gac aaa tcc ctt acc ttc aat gag acc tac cag gac              576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag              624
Ile Ser Glu Leu Val Tyr Gly Ala Lys Leu Gln Pro Leu Asp Phe Lys
            195                 200                 205 gaa aat gca gag caa tcc aga gcg gcc atc aac aaa tgg gtg tcc aat              672
Glu Asn Ala Glu Gln Ser Arg Ala Ala Ile Asn Lys Trp Val Ser Asn
210                 215                 220 aag acc gaa ggc cga atc acc gat gtc att ccc tcg gaa gcc atc aat              720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg              768
Glu Leu Thr Val Leu Val Leu Val Asn Thr Ile Tyr Phe Lys Gly Leu
            245                 250                 255 tgg aag tca aag ttc agc cct gag aac aca agg aag gaa ctg ttc tac              816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc              864
Lys Ala Asp Gly Glu Ser Cys Ser Ala Ser Met Met Tyr Gln Glu Gly
            275                 280                 285 aag ttc cgt tat cgg cgc gtg gct gaa ggc acc cag gtg ctt gag ttg              912
Lys Phe Arg Tyr Arg Arg Val Ala Glu Gly Thr Gln Val Leu Glu Leu
            290                 295                 300 ccc ttc aaa ggt gat gac atc acc atg gtc ctc atc ttg ccc aag cct              960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg             1008
Glu Lys Ser Leu Ala Lys Val Glu Lys Glu Leu Thr Pro Glu Val Leu
            325                 330                 335 caa gag tgg ctg gat gaa ttg gag gag atg atg ctg gtg gtc cac atg             1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa             1104
Pro Arg Phe Arg Ile Glu Asp Gly Phe Ser Leu Lys Glu Gln Leu Gln
            355                 360                 365 gac atg ggc ctt gtc gat ctg ttc agc cct gaa aag tcc aaa ctc cca             1152
Asp Met Gly Leu Val Asp Leu Phe Ser Pro Glu Lys Ser Lys Leu Pro
370                 375                 380 ggt att gtt gca gaa ggc cga gat gac ctc tat gtc tca gat gca ttc             1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca             1248
His Lys Ala Phe Leu Glu Val Asn Glu Glu Gly Ser Glu Ala Ala Ala
            405                 410                 415 agt acc gct gtt gtg att gct ggc cgt tcg cta aac ccc aac agg gtg             1296
Ser Thr Ala Val Val Ile Ala Gly Arg Ser Leu Asn Pro Asn Arg Val
            420                 425                 430 act ttc aag gcc aac agg cct ttc ctg gtt ttt ata aga gaa gtt cct             1344
Thr Phe Lys Ala Asn Arg Pro Phe Leu Val Phe Ile Arg Glu Val Pro
            435                 440                 445 ctg aac act att atc ttc atg ggc aga gta gcc aac cct tgt gtt aag             1392
Leu Asn Thr Ile Ile Phe Met Gly Arg Val Ala Asn Pro Cys Val Lys
450                 455                 460 taaaatgttc ttattctttg cacctcttcc tattttggt ttgtgaacag aagtaaaaat            1452
aaatacaaac tacttccatc tcacattaaa a                                          1483
```

```
<210> SEQ ID NO 26
<211> LENGTH: 464
<212> TYPE: PRT
<213> ORGANISM: Homo sapiens

<400> SEQUENCE: 26

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
            85                  90                  95

His Leu Ala Asp Ser Lys Asn Asp Asn Asp Asn Ile Phe Leu Ser Pro
        100                 105                 110

Leu Ser Ile Ser Thr Ala Phe Ala Met Thr Lys Leu Gly Ala Cys Asn
    115                 120                 125

Asp Thr Leu Gln Gln Leu Met Glu Val Phe Lys Phe Asp Thr Ile Ser
130                 135                 140

Glu Lys Thr Ser Asp Gln Ile His Phe Phe Phe Ala Lys Leu Asn Cys
145                 150                 155                 160

Arg Leu Tyr Arg Lys Ala Asn Lys Ser Ser Lys Leu Val Ser Ala Asn
            165                 170                 175

Arg Leu Phe Gly Asp Lys Ser Leu Thr Phe Asn Glu Thr Tyr Gln Asp
        180                 185                 190

Ile Ser Glu Leu Val Tyr Gly Ala Lys Leu Gln Pro Leu Asp Phe Lys
    195                 200                 205

Glu Asn Ala Glu Gln Ser Arg Ala Ala Ile Asn Lys Trp Val Ser Asn
210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
            245                 250                 255

Trp Lys Ser Lys Phe Ser Pro Glu Asn Thr Arg Lys Glu Leu Phe Tyr
        260                 265                 270

Lys Ala Asp Gly Glu Ser Cys Ser Ala Ser Met Met Tyr Gln Glu Gly
    275                 280                 285

Lys Phe Arg Tyr Arg Arg Val Ala Glu Gly Thr Gln Val Leu Glu Leu
290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
            325                 330                 335

Gln Glu Trp Leu Asp Glu Leu Glu Glu Met Met Leu Val Val His Met
        340                 345                 350

Pro Arg Phe Arg Ile Glu Asp Gly Phe Ser Leu Lys Glu Gln Leu Gln
    355                 360                 365

Asp Met Gly Leu Val Asp Leu Phe Ser Pro Glu Lys Ser Lys Leu Pro
370                 375                 380

Gly Ile Val Ala Glu Gly Arg Asp Asp Leu Tyr Val Ser Asp Ala Phe
```

-continued

```
                385                 390                 395                 400
His Lys Ala Phe Leu Glu Val Asn Glu Glu Gly Ser Glu Ala Ala Ala
                    405                 410                 415

Ser Thr Ala Val Val Ile Ala Gly Arg Ser Leu Asn Pro Asn Arg Val
            420                 425                 430

Thr Phe Lys Ala Asn Arg Pro Phe Leu Val Phe Ile Arg Glu Val Pro
        435                 440                 445

Leu Asn Thr Ile Ile Phe Met Gly Arg Val Ala Asn Pro Cys Val Lys
        450                 455                 460

<210> SEQ ID NO 27
<211> LENGTH: 1483
<212> TYPE: DNA
<213> ORGANISM: Homo sapiens
<220> FEATURE:
<221> NAME/KEY: CDS
<222> LOCATION: (1)..(1392)

<400> SEQUENCE: 27 atg tat tcc aat gtg ata gga act gta acc tct gga aaa agg aag gtt    48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt    96
Tyr Leu Leu Ser Leu Leu Leu Ile Gly Phe Trp Asp Cys Val Thr Cys
                20                  25                  30 cac ggg agc cct gtg gac atc tgc aca gcc aag ccg cgg gac att ccc   144
His Gly Ser Pro Val Asp Ile Cys Thr Ala Lys Pro Arg Asp Ile Pro
            35                  40                  45 atg aat ccc atg tgc att tac cgc tcc ccg gag aag aag gca act gag   192
Met Asn Pro Met Cys Ile Tyr Arg Ser Pro Glu Lys Lys Ala Thr Glu
        50                  55                  60 gat gag ggc tca gaa cag aag atc ccg gag gcc acc aac cgg cgt gtc   240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag   288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc   336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat   384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct   432
Asp Thr Leu Gln Gln Leu Met Glu Val Phe Lys Phe Asp Thr Ile Ser
    130                 135                 140 gag aaa aca tct gat cag atc cac ttc ttc ttt gcc aaa ctg aac tgc   480
Glu Lys Thr Ser Asp Gln Ile His Phe Phe Phe Ala Lys Leu Asn Cys
145                 150                 155                 160 cga ctc tat cga aaa gcc aac aaa tcc tcc aag tta gta tca gcc aat   528
Arg Leu Tyr Arg Lys Ala Asn Lys Ser Ser Lys Leu Val Ser Ala Asn
                165                 170                 175 cgc ctt ttt gga gac aaa tcc ctt acc ttc aat gag acc tac cag gac   576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag   624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat   672
Glu Asn Ala Glu Gln Ser Arg Ala Ala Ile Asn Lys Trp Val Ser Asn
    210                 215                 220
```

```
aag acc gaa ggc cga atc acc gat gtc att ccc tcg gaa gcc atc aat      720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg      768
Glu Leu Thr Val Leu Val Leu Val Asn Thr Ile Tyr Phe Lys Gly Leu
            245                 250                 255 tgg aag tca aag ttc agc cct gag aac aca agg aag gaa ctg ttc tac      816
Trp Lys Ser Lys Phe Ser Pro Glu Asn Thr Arg Lys Glu Leu Phe Tyr
        260                 265                 270 aag gct gat gga gag tcg tgt tca gca tct atg atg tac cag gaa ggc      864
Lys Ala Asp Gly Glu Ser Cys Ser Ala Ser Met Met Tyr Gln Glu Gly
    275                 280                 285 aag ttc cgt tat cgg cgc gtg gct gaa ggc acc cag gtg ctt gag ttg      912
Lys Phe Arg Tyr Arg Arg Val Ala Glu Gly Thr Gln Val Leu Glu Leu
290                 295                 300 ccc ttc aaa ggt gat gac atc acc atg gtc ctc atc ttg ccc aag cct      960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg     1008
Glu Lys Ser Leu Ala Lys Val Glu Lys Glu Leu Thr Pro Glu Val Leu
            325                 330                 335 caa gag tgg ctg gat gaa ttg gag gag atg atg ctg gtg gtc cac atg     1056
Gln Glu Trp Leu Asp Glu Leu Glu Glu Met Met Leu Val Val His Met
        340                 345                 350 ccc cgc ttc cgc att gag gac ggc ttc agt ttg aag gag cag ctg caa     1104
Pro Arg Phe Arg Ile Glu Asp Gly Phe Ser Leu Lys Glu Gln Leu Gln
    355                 360                 365 gac atg ggc ctt gtc gat ctg ttc agc cct gaa aag tcc aaa ctc cca     1152
Asp Met Gly Leu Val Asp Leu Phe Ser Pro Glu Lys Ser Lys Leu Pro
370                 375                 380 ggt att gtt gca gaa ggc cga gat gac ctc tat gtc tca gat gca ttc     1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca     1248
His Lys Ala Phe Leu Glu Val Asn Glu Glu Gly Ser Glu Ala Ala Ala
            405                 410                 415 agt acc gct gtt gtg att gct ggc cat tcg cta aac ccc aac agg gtg     1296
Ser Thr Ala Val Val Ile Ala Gly His Ser Leu Asn Pro Asn Arg Val
        420                 425                 430 act ttc aag gcc aac agg cct ttc ctg gtt ttt ata aga gaa gtt cct     1344
Thr Phe Lys Ala Asn Arg Pro Phe Leu Val Phe Ile Arg Glu Val Pro
    435                 440                 445 ctg aac act att atc ttc atg ggc aga gta gcc aac cct tgt gtt aag     1392
Leu Asn Thr Ile Ile Phe Met Gly Arg Val Ala Asn Pro Cys Val Lys
450                 455                 460 taaaatgttc ttattctttg cacctcttcc tattttggt tgtgaacag aagtaaaaat     1452 aaatacaaac tacttccatc tcacattaaa a                                  1483

<210> SEQ ID NO 28
<211> LENGTH: 464
<212> TYPE: PRT
<213> ORGANISM: Homo sapiens

<400> SEQUENCE: 28

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
```

-continued

```
                  35                   40                    45
Met Asn Pro Met Cys Ile Tyr Arg Ser Pro Glu Lys Lys Ala Thr Glu
 50                   55                   60
Asp Glu Gly Ser Glu Gln Lys Ile Pro Glu Ala Thr Asn Arg Arg Val
 65                   70                   75                   80
Trp Glu Leu Ser Lys Ala Asn Ser Arg Phe Ala Thr Thr Phe Tyr Gln
                  85                   90                   95
His Leu Ala Asp Ser Lys Asn Asp Asn Asp Asn Ile Phe Leu Ser Pro
                 100                  105                  110
Leu Ser Ile Ser Thr Ala Phe Ala Met Thr Lys Leu Gly Ala Cys Asn
                 115                  120                  125
Asp Thr Leu Gln Gln Leu Met Glu Val Phe Lys Phe Asp Thr Ile Ser
                 130                  135                  140
Glu Lys Thr Ser Asp Gln Ile His Phe Phe Phe Ala Lys Leu Asn Cys
145                  150                  155                  160
Arg Leu Tyr Arg Lys Ala Asn Lys Ser Ser Lys Leu Val Ser Ala Asn
                 165                  170                  175
Arg Leu Phe Gly Asp Lys Ser Leu Thr Phe Asn Glu Thr Tyr Gln Asp
                 180                  185                  190
Ile Ser Glu Leu Val Tyr Gly Ala Lys Leu Gln Pro Leu Asp Phe Lys
                 195                  200                  205
Glu Asn Ala Glu Gln Ser Arg Ala Ala Ile Asn Lys Trp Val Ser Asn
                 210                  215                  220
Lys Thr Glu Gly Arg Ile Thr Asp Val Ile Pro Ser Glu Ala Ile Asn
225                  230                  235                  240
Glu Leu Thr Val Leu Val Leu Val Asn Thr Ile Tyr Phe Lys Gly Leu
                 245                  250                  255
Trp Lys Ser Lys Phe Ser Pro Glu Asn Thr Arg Lys Glu Leu Phe Tyr
                 260                  265                  270
Lys Ala Asp Gly Glu Ser Cys Ser Ala Ser Met Met Tyr Gln Glu Gly
                 275                  280                  285
Lys Phe Arg Tyr Arg Arg Val Ala Glu Gly Thr Gln Val Leu Glu Leu
                 290                  295                  300
Pro Phe Lys Gly Asp Asp Ile Thr Met Val Leu Ile Leu Pro Lys Pro
305                  310                  315                  320
Glu Lys Ser Leu Ala Lys Val Glu Lys Glu Leu Thr Pro Glu Val Leu
                 325                  330                  335
Gln Glu Trp Leu Asp Glu Leu Glu Glu Met Met Leu Val Val His Met
                 340                  345                  350
Pro Arg Phe Arg Ile Glu Asp Gly Phe Ser Leu Lys Glu Gln Leu Gln
                 355                  360                  365
Asp Met Gly Leu Val Asp Leu Phe Ser Pro Glu Lys Ser Lys Leu Pro
                 370                  375                  380
Gly Ile Val Ala Glu Gly Arg Asp Asp Leu Tyr Val Ser Asp Ala Phe
385                  390                  395                  400
His Lys Ala Phe Leu Glu Val Asn Glu Glu Gly Ser Glu Ala Ala Ala
                 405                  410                  415
Ser Thr Ala Val Val Ile Ala Gly His Ser Leu Asn Pro Asn Arg Val
                 420                  425                  430
Thr Phe Lys Ala Asn Arg Pro Phe Leu Val Phe Ile Arg Glu Val Pro
                 435                  440                  445
Leu Asn Thr Ile Ile Phe Met Gly Arg Val Ala Asn Pro Cys Val Lys
                 450                  455                  460
```

-continued

```
<210> SEQ ID NO 29
<211> LENGTH: 1486
<212> TYPE: DNA
<213> ORGANISM: Homo sapiens
<220> FEATURE:
<221> NAME/KEY: CDS
<222> LOCATION: (1)..(1395)

<400> SEQUENCE: 29 atg tat tcc aat gtg ata gga act gta acc tct gga aaa agg aag gtt      48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt      96
Tyr Leu Leu Ser Leu Leu Leu Ile Gly Phe Trp Asp Cys Val Thr Cys
            20                  25                  30 cac ggg agc cct gtg gac atc tgc aca gcc aag ccg cgg gac att ccc     144
His Gly Ser Pro Val Asp Ile Cys Thr Ala Lys Pro Arg Asp Ile Pro
        35                  40                  45 atg aat ccc atg tgc att tac cgc tcc ccg gag aag aag gca act gag     192
Met Asn Pro Met Cys Ile Tyr Arg Ser Pro Glu Lys Lys Ala Thr Glu
    50                  55                  60 gat gag ggc tca gaa cag aag atc ccg gag gcc acc aac cgg cgt gtc     240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag     288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc     336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat     384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct     432
Asp Thr Leu Gln Gln Leu Met Glu Val Phe Lys Phe Asp Thr Ile Ser
    130                 135                 140 gag aaa aca tct gat cag atc cac ttc ttc ttt gcc aaa ctg aac tgc     480
Glu Lys Thr Ser Asp Gln Ile His Phe Phe Phe Ala Lys Leu Asn Cys
145                 150                 155                 160 cga ctc tat cga aaa gcc aac aaa tcc tcc aag tta gta tca gcc aat     528
Arg Leu Tyr Arg Lys Ala Asn Lys Ser Ser Lys Leu Val Ser Ala Asn
                165                 170                 175 cgc ctt ttt gga gac aaa tcc ctt acc ttc aat gag acc tac cag gac     576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag     624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat     672
Glu Asn Ala Glu Gln Ser Arg Ala Ala Ile Asn Lys Trp Val Ser Asn
    210                 215                 220 aag acc gaa ggc cga atc acc gat gtc att ccc tcg gaa gcc atc aat     720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg     768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac     816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc     864
Lys Ala Asp Gly Glu Ser Cys Ser Ala Ser Met Met Tyr Gln Glu Gly
```

```
          Lys Ala Asp Gly Glu Ser Cys Ser Ala Ser Met Met Tyr Gln Glu Gly
              275                 280                 285 aag ttc cgt tat cgg cgc gtg gct gaa ggc acc cag gtg ctt gag ttg       912
Lys Phe Arg Tyr Arg Arg Val Ala Glu Gly Thr Gln Val Leu Glu Leu
    290                 295                 300 ccc ttc aaa ggt gat gac atc acc atg gtc ctc atc ttg ccc aag cct       960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg      1008
Glu Lys Ser Leu Ala Lys Val Glu Lys Glu Leu Thr Pro Glu Val Leu
                325                 330                 335 caa gag tgg ctg gat gaa ttg gag gag atg atg ctg gtg gtc cac atg      1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa      1104
Pro Arg Phe Arg Ile Glu Asp Gly Phe Ser Leu Lys Glu Gln Leu Gln
        355                 360                 365 gac atg ggc ctt gtc gat ctg ttc agc cct gaa aag tcc aaa ctc cca      1152
Asp Met Gly Leu Val Asp Leu Phe Ser Pro Glu Lys Ser Lys Leu Pro
370                 375                 380 ggt att gtt gca gaa ggc cga gat gac ctc tat gtc tca gat gca ttc      1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca      1248
His Lys Ala Phe Leu Glu Val Asn Glu Glu Gly Ser Glu Ala Ala Ala
                405                 410                 415 agt acc gct gtt gtg att gct ggc cgt cca tcg cta aac ccc aac agg      1296
Ser Thr Ala Val Val Ile Ala Gly Arg Pro Ser Leu Asn Pro Asn Arg
            420                 425                 430 gtg act ttc aag gcc aac agg cct ttc ctg gtt ttt ata aga gaa gtt      1344
Val Thr Phe Lys Ala Asn Arg Pro Phe Leu Val Phe Ile Arg Glu Val
        435                 440                 445 cct ctg aac act att atc ttc atg ggc aga gta gcc aac cct tgt gtt      1392
Pro Leu Asn Thr Ile Ile Phe Met Gly Arg Val Ala Asn Pro Cys Val
450                 455                 460 aag taaaatgttc ttattctttg cacctcttcc tattttggt ttgtgaacag            1445
Lys
465 aagtaaaaat aaatacaaac tacttccatc tcacattaaa a                        1486

<210> SEQ ID NO 30
<211> LENGTH: 465
<212> TYPE: PRT
<213> ORGANISM: Homo sapiens

<400> SEQUENCE: 30

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
```

```
                100                 105                 110
Leu Ser Ile Ser Thr Ala Phe Ala Met Thr Lys Leu Gly Ala Cys Asn
            115                 120                 125

Asp Thr Leu Gln Gln Leu Met Glu Val Phe Lys Phe Asp Thr Ile Ser
        130                 135                 140

Glu Lys Thr Ser Asp Gln Ile His Phe Phe Ala Lys Leu Asn Cys
145                 150                 155                 160

Arg Leu Tyr Arg Lys Ala Asn Lys Ser Ser Lys Leu Val Ser Ala Asn
            165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
            195                 200                 205

Glu Asn Ala Glu Gln Ser Arg Ala Ala Ile Asn Lys Trp Val Ser Asn
        210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
            245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
            275                 280                 285

Lys Phe Arg Tyr Arg Arg Val Ala Glu Gly Thr Gln Val Leu Glu Leu
            290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
            325                 330                 335

Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
            355                 360                 365

Asp Met Gly Leu Val Asp Leu Phe Ser Pro Glu Lys Ser Lys Leu Pro
        370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
            405                 410                 415

Ser Thr Ala Val Val Ile Ala Gly Arg Pro Ser Leu Asn Pro Asn Arg
            420                 425                 430

Val Thr Phe Lys Ala Asn Arg Pro Phe Leu Val Phe Ile Arg Glu Val
            435                 440                 445

Pro Leu Asn Thr Ile Ile Phe Met Gly Arg Val Ala Asn Pro Cys Val
            450                 455                 460

Lys
465

<210> SEQ ID NO 31
<211> LENGTH: 1480
<212> TYPE: DNA
<213> ORGANISM: Homo sapiens
<220> FEATURE:
<221> NAME/KEY: CDS
<222> LOCATION: (1)..(1389)
```

-continued

```
<400> SEQUENCE: 31 atg tat tcc aat gtg ata gga act gta acc tct gga aaa agg aag gtt    48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt    96
Tyr Leu Leu Ser Leu Leu Leu Ile Gly Phe Trp Asp Cys Val Thr Cys
            20                  25                  30 cac ggg agc cct gtg gac atc tgc aca gcc aag ccg cgg gac att ccc   144
His Gly Ser Pro Val Asp Ile Cys Thr Ala Lys Pro Arg Asp Ile Pro
        35                  40                  45 atg aat ccc atg tgc att tac cgc tcc ccg gag aag aag gca act gag   192
Met Asn Pro Met Cys Ile Tyr Arg Ser Pro Glu Lys Lys Ala Thr Glu
    50                  55                  60 gat gag ggc tca gaa cag aag atc ccg gag gcc acc aac cgg cgt gtc   240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag   288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc   336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat   384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct   432
Asp Thr Leu Gln Gln Leu Met Glu Val Phe Lys Phe Asp Thr Ile Ser
    130                 135                 140 gag aaa aca tct gat cag atc cac ttc ttc ttt gcc aaa ctg aac tgc   480
Glu Lys Thr Ser Asp Gln Ile His Phe Phe Phe Ala Lys Leu Asn Cys
145                 150                 155                 160 cga ctc tat cga aaa gcc aac aaa tcc tcc aag tta gta tca gcc aat   528
Arg Leu Tyr Arg Lys Ala Asn Lys Ser Ser Lys Leu Val Ser Ala Asn
                165                 170                 175 cgc ctt ttt gga gac aaa tcc ctt acc ttc aat gag acc tac cag gac   576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag   624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat   672
Glu Asn Ala Glu Gln Ser Arg Ala Ala Ile Asn Lys Trp Val Ser Asn
    210                 215                 220 aag acc gaa ggc cga atc acc gat gtc att ccc tcg gaa gcc atc aat   720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg   768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac   816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc   864
Lys Ala Asp Gly Glu Ser Cys Ser Ala Ser Met Met Tyr Gln Glu Gly
        275                 280                 285 aag ttc cgt tat cgg cgc gtg gct gaa ggc acc cag gtg ctt gag ttg   912
Lys Phe Arg Tyr Arg Arg Val Ala Glu Gly Thr Gln Val Leu Glu Leu
    290                 295                 300 ccc ttc aaa ggt gat gac atc acc atg gtc ctc atc ttg ccc aag cct   960
Pro Phe Lys Gly Asp Asp Ile Thr Met Val Leu Ile Leu Pro Lys Pro
```

```
                     305                 310                 315                 320
gag aag agc ctg gcc aag gta gag aag gaa ctc acc cca gag gtg ctg       1008
Glu Lys Ser Leu Ala Lys Val Glu Lys Glu Leu Thr Pro Glu Val Leu
                325                 330                 335 caa gag tgg ctg gat gaa ttg gag gag atg atg ctg gtg gtc cac atg       1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa       1104
Pro Arg Phe Arg Ile Glu Asp Gly Phe Ser Leu Lys Glu Gln Leu Gln
        355                 360                 365 gac atg ggc ctt gtc gat ctg ttc agc cct gaa aag tcc aaa ctc cca       1152
Asp Met Gly Leu Val Asp Leu Phe Ser Pro Glu Lys Ser Lys Leu Pro
    370                 375                 380 ggt att gtt gca gaa ggc cga gat gac ctc tat gtc tca gat gca ttc       1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca       1248
His Lys Ala Phe Leu Glu Val Asn Glu Glu Gly Ser Glu Ala Ala Ala
                405                 410                 415 agt acc gct gtt gtg att gct ggc tcg cta aac ccc aac agg gtg act       1296
Ser Thr Ala Val Val Ile Ala Gly Ser Leu Asn Pro Asn Arg Val Thr
            420                 425                 430 ttc aag gcc aac agg cct ttc ctg gtt ttt ata aga gaa gtt cct ctg       1344
Phe Lys Ala Asn Arg Pro Phe Leu Val Phe Ile Arg Glu Val Pro Leu
        435                 440                 445 aac act att atc ttc atg ggc aga gta gcc aac cct tgt gtt aag           1389
Asn Thr Ile Ile Phe Met Gly Arg Val Ala Asn Pro Cys Val Lys
    450                 455                 460 taaaatgttc ttattctttg cacctcttcc tattttggt tgtgaacag aagtaaaaat       1449 aaatacaaac tacttccatc tcacattaaa a                                    1480

<210> SEQ ID NO 32
<211> LENGTH: 463
<212> TYPE: PRT
<213> ORGANISM: Homo sapiens

<400> SEQUENCE: 32

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160
```

```
Arg Leu Tyr Arg Lys Ala Asn Lys Ser Ser Lys Leu Val Ser Ala Asn
                165                 170                 175
Arg Leu Phe Gly Asp Lys Ser Leu Thr Phe Asn Glu Thr Tyr Gln Asp
            180                 185                 190
Ile Ser Glu Leu Val Tyr Gly Ala Lys Leu Gln Pro Leu Asp Phe Lys
        195                 200                 205
Glu Asn Ala Glu Gln Ser Arg Ala Ala Ile Asn Lys Trp Val Ser Asn
    210                 215                 220
Lys Thr Glu Gly Arg Ile Thr Asp Val Ile Pro Ser Glu Ala Ile Asn
225                 230                 235                 240
Glu Leu Thr Val Leu Val Leu Asn Thr Ile Tyr Phe Lys Gly Leu
                245                 250                 255
Trp Lys Ser Lys Phe Ser Pro Glu Asn Thr Arg Lys Glu Leu Phe Tyr
                260                 265                 270
Lys Ala Asp Gly Glu Ser Cys Ser Ala Ser Met Met Tyr Gln Glu Gly
            275                 280                 285
Lys Phe Arg Tyr Arg Arg Val Ala Glu Gly Thr Gln Val Leu Glu Leu
        290                 295                 300
Pro Phe Lys Gly Asp Asp Ile Thr Met Val Leu Ile Leu Pro Lys Pro
305                 310                 315                 320
Glu Lys Ser Leu Ala Lys Val Glu Lys Glu Leu Thr Pro Glu Val Leu
                325                 330                 335
Gln Glu Trp Leu Asp Glu Leu Glu Glu Met Met Leu Val Val His Met
                340                 345                 350
Pro Arg Phe Arg Ile Glu Asp Gly Phe Ser Leu Lys Glu Gln Leu Gln
                355                 360                 365
Asp Met Gly Leu Val Asp Leu Phe Ser Pro Glu Lys Ser Lys Leu Pro
    370                 375                 380
Gly Ile Val Ala Glu Gly Arg Asp Asp Leu Tyr Val Ser Asp Ala Phe
385                 390                 395                 400
His Lys Ala Phe Leu Glu Val Asn Glu Glu Gly Ser Glu Ala Ala Ala
                405                 410                 415
Ser Thr Ala Val Val Ile Ala Gly Ser Leu Asn Pro Asn Arg Val Thr
            420                 425                 430
Phe Lys Ala Asn Arg Pro Phe Leu Val Phe Ile Arg Glu Val Pro Leu
        435                 440                 445
Asn Thr Ile Ile Phe Met Gly Arg Val Ala Asn Pro Cys Val Lys
    450                 455                 460

<210> SEQ ID NO 33
<211> LENGTH: 1480
<212> TYPE: DNA
<213> ORGANISM: Homo sapiens
<220> FEATURE:
<221> NAME/KEY: CDS
<222> LOCATION: (1)..(1389)

<400> SEQUENCE: 33 atg tat tcc aat gtg ata gga act gta acc tct gga aaa agg aag gtt      48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt      96
Tyr Leu Leu Ser Leu Leu Leu Ile Gly Phe Trp Asp Cys Val Thr Cys
                20                  25                  30 cac ggg agc cct gtg gac atc tgc aca gcc aag ccg cgg gac att ccc     144
His Gly Ser Pro Val Asp Ile Cys Thr Ala Lys Pro Arg Asp Ile Pro
            35                  40                  45
```

```
atg aat ccc atg tgc att tac cgc tcc ccg gag aag aag gca act gag      192
Met Asn Pro Met Cys Ile Tyr Arg Ser Pro Glu Lys Lys Ala Thr Glu
    50              55                  60 gat gag ggc tca gaa cag aag atc ccg gag gcc acc aac cgg cgt gtc      240
Asp Glu Gly Ser Glu Gln Lys Ile Pro Glu Ala Thr Asn Arg Arg Val
65              70                  75                  80 tgg gaa ctg tcc aag gcc aat tcc cgc ttt gct acc act ttc tat cag      288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc      336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat      384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct      432
Asp Thr Leu Gln Gln Leu Met Glu Val Phe Lys Phe Asp Thr Ile Ser
130                 135                 140 gag aaa aca tct gat cag atc cac ttc ttc ttt gcc aaa ctg aac tgc      480
Glu Lys Thr Ser Asp Gln Ile His Phe Phe Phe Ala Lys Leu Asn Cys
145                 150                 155                 160 cga ctc tat cga aaa gcc aac aaa tcc tcc aag tta gta tca gcc aat      528
Arg Leu Tyr Arg Lys Ala Asn Lys Ser Ser Lys Leu Val Ser Ala Asn
                165                 170                 175 cgc ctt ttt gga gac aaa tcc ctt acc ttc aat gag acc tac cag gac      576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag      624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat      672
Glu Asn Ala Glu Gln Ser Arg Ala Ala Ile Asn Lys Trp Val Ser Asn
210                 215                 220 aag acc gaa ggc cga atc acc gat gtc att ccc tcg gaa gcc atc aat      720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg      768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac      816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc      864
Lys Ala Asp Gly Glu Ser Cys Ser Ala Ser Met Met Tyr Gln Glu Gly
        275                 280                 285 aag ttc cgt tat cgg cgc gtg gct gaa ggc acc cag gtg ctt gag ttg      912
Lys Phe Arg Tyr Arg Arg Val Ala Glu Gly Thr Gln Val Leu Glu Leu
290                 295                 300 ccc ttc aaa ggt gat gac atc acc atg gtc ctc atc ttg ccc aag cct      960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg     1008
Glu Lys Ser Leu Ala Lys Val Glu Lys Glu Leu Thr Pro Glu Val Leu
                325                 330                 335 caa gag tgg ctg gat gaa ttg gag gag atg atg ctg gtg gtc cac atg     1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa     1104
Pro Arg Phe Arg Ile Glu Asp Gly Phe Ser Leu Lys Glu Gln Leu Gln
        355                 360                 365
```

```
gac atg ggc ctt gtc gat ctg ttc agc cct gaa aag tcc aaa ctc cca    1152
Asp Met Gly Leu Val Asp Leu Phe Ser Pro Glu Lys Ser Lys Leu Pro
    370                 375                 380 ggt att gtt gca gaa ggc cga gat gac ctc tat gtc tca gat gca ttc    1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca    1248
His Lys Ala Phe Leu Glu Val Asn Glu Glu Gly Ser Glu Ala Ala Ala
                405                 410                 415 agt acc gct gtt gtg att gct ggc cgt cta aac ccc aac agg gtg act    1296
Ser Thr Ala Val Val Ile Ala Gly Arg Leu Asn Pro Asn Arg Val Thr
            420                 425                 430 ttc aag gcc aac agg cct ttc ctg gtt ttt ata aga gaa gtt cct ctg    1344
Phe Lys Ala Asn Arg Pro Phe Leu Val Phe Ile Arg Glu Val Pro Leu
        435                 440                 445 aac act att atc ttc atg ggc aga gta gcc aac cct tgt gtt aag        1389
Asn Thr Ile Ile Phe Met Gly Arg Val Ala Asn Pro Cys Val Lys
    450                 455                 460 taaaatgttc ttattctttg cacctcttcc tattttggt ttgtgaacag aagtaaaaat   1449
aaatacaaac tacttccatc tcacattaaa a                                 1480

<210> SEQ ID NO 34
<211> LENGTH: 463
<212> TYPE: PRT
<213> ORGANISM: Homo sapiens

<400> SEQUENCE: 34

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240
```

```
Glu Leu Thr Val Leu Val Leu Val Asn Thr Ile Tyr Phe Lys Gly Leu
            245                 250                 255

Trp Lys Ser Lys Phe Ser Pro Glu Asn Thr Arg Lys Glu Leu Phe Tyr
        260                 265                 270

Lys Ala Asp Gly Glu Ser Cys Ser Ala Ser Met Met Tyr Gln Glu Gly
    275                 280                 285

Lys Phe Arg Tyr Arg Arg Val Ala Glu Gly Thr Gln Val Leu Glu Leu
290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
            325                 330                 335

Gln Glu Trp Leu Asp Glu Leu Glu Met Met Leu Val Val His Met
        340                 345                 350

Pro Arg Phe Arg Ile Glu Asp Gly Phe Ser Leu Lys Glu Gln Leu Gln
    355                 360                 365

Asp Met Gly Leu Val Asp Leu Phe Ser Pro Glu Lys Ser Lys Leu Pro
370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
            405                 410                 415

Ser Thr Ala Val Val Ile Ala Gly Arg Leu Asn Pro Asn Arg Val Thr
        420                 425                 430

Phe Lys Ala Asn Arg Pro Phe Leu Val Phe Ile Arg Glu Val Pro Leu
    435                 440                 445

Asn Thr Ile Ile Phe Met Gly Arg Val Ala Asn Pro Cys Val Lys
450                 455                 460

<210> SEQ ID NO 35
<211> LENGTH: 1483
<212> TYPE: DNA
<213> ORGANISM: Homo sapiens
<220> FEATURE:
<221> NAME/KEY: CDS
<222> LOCATION: (1)..(1392)

<400> SEQUENCE: 35 atg tat tcc aat gtg ata gga act gta acc tct gga aaa agg aag gtt      48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt      96
Tyr Leu Leu Ser Leu Leu Leu Ile Gly Phe Trp Asp Cys Val Thr Cys
            20                  25                  30 cac ggg agc cct gtg gac atc tgc aca gcc aag ccg cgg gac att ccc     144
His Gly Ser Pro Val Asp Ile Cys Thr Ala Lys Pro Arg Asp Ile Pro
        35                  40                  45 atg aat ccc atg tgc att tac cgc tcc ccg gag aag aag gca act gag     192
Met Asn Pro Met Cys Ile Tyr Arg Ser Pro Glu Lys Lys Ala Thr Glu
    50                  55                  60 gat gag ggc tca gaa cag aag atc ccg gag gcc acc aac cgg cgt gtc     240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag     288
Trp Glu Leu Ser Lys Ala Asn Ser Arg Phe Ala Thr Thr Phe Tyr Gln
            85                  90                  95 cac ctg gca gat tcc aag aat gac aat gat aac att ttc ctg tca ccc     336
His Leu Ala Asp Ser Lys Asn Asp Asn Asp Asn Ile Phe Leu Ser Pro
```

```
                        100                 105                 110
ctg agt atc tcc acg gct ttt gct atg acc aag ctg ggt gcc tgt aat       384
Leu Ser Ile Ser Thr Ala Phe Ala Met Thr Lys Leu Gly Ala Cys Asn
            115                 120                 125 gac acc ctc cag caa ctg atg gag gta ttt aag ttt gac acc ata tct       432
Asp Thr Leu Gln Gln Leu Met Glu Val Phe Lys Phe Asp Thr Ile Ser
130                 135                 140 gag aaa aca tct gat cag atc cac ttc ttc ttt gcc aaa ctg aac tgc       480
Glu Lys Thr Ser Asp Gln Ile His Phe Phe Phe Ala Lys Leu Asn Cys
145                 150                 155                 160 cga ctc tat cga aaa gcc cag aaa tcc tcc aag tta gta tca gcc aat       528
Arg Leu Tyr Arg Lys Ala Gln Lys Ser Ser Lys Leu Val Ser Ala Asn
                165                 170                 175 cgc ctt ttt gga gac aaa tcc ctt acc ttc aat gag acc tac cag gac       576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag       624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat       672
Glu Asn Ala Glu Gln Ser Arg Ala Ala Ile Asn Lys Trp Val Ser Asn
210                 215                 220 aag acc gaa ggc cga atc acc gat gtc att ccc tcg gaa gcc atc aat       720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg       768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac       816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc       864
Lys Ala Asp Gly Glu Ser Cys Ser Ala Ser Met Met Tyr Gln Glu Gly
        275                 280                 285 aag ttc cgt tat cgg cgc gtg gct gaa ggc acc cag gtg ctt gag ttg       912
Lys Phe Arg Tyr Arg Arg Val Ala Glu Gly Thr Gln Val Leu Glu Leu
290                 295                 300 ccc ttc aaa ggt gat gac atc acc atg gtc ctc atc ttg ccc aag cct       960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg      1008
Glu Lys Ser Leu Ala Lys Val Glu Lys Glu Leu Thr Pro Glu Val Leu
                325                 330                 335 caa gag tgg ctg gat gaa ttg gag gag atg atg ctg gtg gtc cac atg      1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa      1104
Pro Arg Phe Arg Ile Glu Asp Gly Phe Ser Leu Lys Glu Gln Leu Gln
        355                 360                 365 gac atg ggc ctt gtc gat ctg ttc agc cct gaa aag tcc aaa ctc cca      1152
Asp Met Gly Leu Val Asp Leu Phe Ser Pro Glu Lys Ser Lys Leu Pro
370                 375                 380 ggt att gtt gca gaa ggc cga gat gac ctc tat gtc tca gat gca ttc      1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca      1248
His Lys Ala Phe Leu Glu Val Asn Glu Glu Gly Ser Glu Ala Ala Ala
                405                 410                 415 agt acc gct gtt gtg att gct ggc cgt tcg cta aac ccc aac agg gtg      1296
Ser Thr Ala Val Val Ile Ala Gly Arg Ser Leu Asn Pro Asn Arg Val
```

-continued

```
                420             425             430
act ttc aag gcc aac agg cct ttc ctg gtt ttt ata aga gaa gtt cct     1344
Thr Phe Lys Ala Asn Arg Pro Phe Leu Val Phe Ile Arg Glu Val Pro
        435                 440                 445 ctg aac act att atc ttc atg ggc aga gta gcc aac cct tgt gtt aag     1392
Leu Asn Thr Ile Ile Phe Met Gly Arg Val Ala Asn Pro Cys Val Lys
    450                 455                 460 taaaatgttc ttattctttg cacctcttcc tattttggt ttgtgaacag aagtaaaaat    1452
aaatacaaac tacttccatc tcacattaaa a                                  1483

<210> SEQ ID NO 36
<211> LENGTH: 464
<212> TYPE: PRT
<213> ORGANISM: Homo sapiens

<400> SEQUENCE: 36

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160

Arg Leu Tyr Arg Lys Ala Gln Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
```

```
                         305                 310                 315                 320
Glu Lys Ser Leu Ala Lys Val Glu Lys Glu Leu Thr Pro Glu Val Leu
                 325                 330                 335

Gln Glu Trp Leu Asp Glu Leu Glu Glu Met Met Leu Val Val His Met
                 340                 345                 350

Pro Arg Phe Arg Ile Glu Asp Gly Phe Ser Leu Lys Glu Gln Leu Gln
                 355                 360                 365

Asp Met Gly Leu Val Asp Leu Phe Ser Pro Glu Lys Ser Lys Leu Pro
                 370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Gly Ser Glu Ala Ala Ala
                 405                 410                 415

Ser Thr Ala Val Val Ile Ala Gly Arg Ser Leu Asn Pro Asn Arg Val
                 420                 425                 430

Thr Phe Lys Ala Asn Arg Pro Phe Leu Val Phe Ile Arg Glu Val Pro
                 435                 440                 445

Leu Asn Thr Ile Ile Phe Met Gly Arg Val Ala Asn Pro Cys Val Lys
                 450                 455                 460

<210> SEQ ID NO 37
<211> LENGTH: 1483
<212> TYPE: DNA
<213> ORGANISM: Homo sapiens
<220> FEATURE:
<221> NAME/KEY: CDS
<222> LOCATION: (1)..(1392)

<400> SEQUENCE: 37 atg tat tcc aat gtg ata gga act gta acc tct gga aaa agg aag gtt      48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt      96
Tyr Leu Leu Ser Leu Leu Leu Ile Gly Phe Trp Asp Cys Val Thr Cys
            20                  25                  30 cac ggg agc cct gtg gac atc tgc aca gcc aag ccg cgg gac att ccc     144
His Gly Ser Pro Val Asp Ile Cys Thr Ala Lys Pro Arg Asp Ile Pro
        35                  40                  45 atg aat ccc atg tgc att tac cgc tcc ccg gag aag aag gca act gag     192
Met Asn Pro Met Cys Ile Tyr Arg Ser Pro Glu Lys Lys Ala Thr Glu
    50                  55                  60 gat gag ggc tca gaa cag aag atc ccg gag gcc acc aac cgg cgt gtc     240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag     288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc     336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat     384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct     432
Asp Thr Leu Gln Gln Leu Met Glu Val Phe Lys Phe Asp Thr Ile Ser
    130                 135                 140 gag aaa aca tct gat cag atc cac ttc ttc ttt gcc aaa ctg aac tgc     480
Glu Lys Thr Ser Asp Gln Ile His Phe Phe Phe Ala Lys Leu Asn Cys
145                 150                 155                 160
```

```
cga ctc tat cga aaa gcc cag aaa tcc tcc aag tta gta tca gcc aat      528
Arg Leu Tyr Arg Lys Ala Gln Lys Ser Ser Lys Leu Val Ser Ala Asn
            165                 170                 175 cgc ctt ttt gga gac aaa tcc ctt acc ttc aat gag acc tac cag gac      576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag      624
Ile Ser Glu Leu Val Tyr Gly Ala Lys Leu Gln Pro Leu Asp Phe Lys
            195                 200                 205 gaa aat gca gag caa tcc aga gcg gcc atc aac aaa tgg gtg tcc aat      672
Glu Asn Ala Glu Gln Ser Arg Ala Ala Ile Asn Lys Trp Val Ser Asn
    210                 215                 220 aag acc gaa ggc cga atc acc gat gtc att ccc tcg gaa gcc atc aat      720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg      768
Glu Leu Thr Val Leu Val Leu Val Asn Thr Ile Tyr Phe Lys Gly Leu
            245                 250                 255 tgg aag tca aag ttc agc cct gag aac aca agg aag gaa ctg ttc tac      816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc      864
Lys Ala Asp Gly Glu Ser Cys Ser Ala Ser Met Met Tyr Gln Glu Gly
            275                 280                 285 aag ttc cgt tat cgg cgc gtg gct gaa ggc acc cag gtg ctt gag ttg      912
Lys Phe Arg Tyr Arg Arg Val Ala Glu Gly Thr Gln Val Leu Glu Leu
            290                 295                 300 ccc ttc aaa ggt gat gac atc acc atg gtc ctc atc ttg ccc aag cct      960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg     1008
Glu Lys Ser Leu Ala Lys Val Glu Lys Glu Leu Thr Pro Glu Val Leu
            325                 330                 335 caa gag tgg ctg gat gaa ttg gag gag atg atg ctg gtg gtc cac atg     1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa     1104
Pro Arg Phe Arg Ile Glu Asp Gly Phe Ser Leu Lys Glu Gln Leu Gln
            355                 360                 365 gac atg ggc ctt gtc gat ctg ttc agc cct gaa aag tcc aaa ctc cca     1152
Asp Met Gly Leu Val Asp Leu Phe Ser Pro Glu Lys Ser Lys Leu Pro
            370                 375                 380 ggt att gtt gca gaa ggc cga gat gac ctc tat gtc tca gat gca ttc     1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca     1248
His Lys Ala Phe Leu Glu Val Asn Glu Glu Gly Ser Glu Ala Ala Ala
            405                 410                 415 agt acc gct gtt gtg att gct ggc cat tcg cta aac ccc aac agg gtg     1296
Ser Thr Ala Val Val Ile Ala Gly His Ser Leu Asn Pro Asn Arg Val
            420                 425                 430 act ttc aag gcc aac agg cct ttc ctg gtt ttt ata aga gaa gtt cct     1344
Thr Phe Lys Ala Asn Arg Pro Phe Leu Val Phe Ile Arg Glu Val Pro
            435                 440                 445 ctg aac act att atc ttc atg ggc aga gta gcc aac cct tgt gtt aag     1392
Leu Asn Thr Ile Ile Phe Met Gly Arg Val Ala Asn Pro Cys Val Lys
            450                 455                 460 taaaatgttc ttattctttg cacctcttcc tattttggt ttgtgaacag aagtaaaaat    1452
aaatacaaac tacttccatc tcacattaaa a                                  1483
```

<210> SEQ ID NO 38
<211> LENGTH: 464
<212> TYPE: PRT
<213> ORGANISM: Homo sapiens

<400> SEQUENCE: 38

```
Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160

Arg Leu Tyr Arg Lys Ala Gln Lys Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
    370                 375                 380
```

```
Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
            405                 410                 415

Ser Thr Ala Val Val Ile Ala Gly His Ser Leu Asn Pro Asn Arg Val
        420                 425                 430

Thr Phe Lys Ala Asn Arg Pro Phe Leu Val Phe Ile Arg Glu Val Pro
    435                 440                 445

Leu Asn Thr Ile Ile Phe Met Gly Arg Val Ala Asn Pro Cys Val Lys
450                 455                 460

<210> SEQ ID NO 39
<211> LENGTH: 1486
<212> TYPE: DNA
<213> ORGANISM: Homo sapiens
<220> FEATURE:
<221> NAME/KEY: CDS
<222> LOCATION: (1)..(1395)

<400> SEQUENCE: 39 atg tat tcc aat gtg ata gga act gta acc tct gga aaa agg aag gtt      48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt      96
Tyr Leu Leu Ser Leu Leu Leu Ile Gly Phe Trp Asp Cys Val Thr Cys
            20                  25                  30 cac ggg agc cct gtg gac atc tgc aca gcc aag ccg cgg gac att ccc     144
His Gly Ser Pro Val Asp Ile Cys Thr Ala Lys Pro Arg Asp Ile Pro
        35                  40                  45 atg aat ccc atg tgc att tac cgc tcc ccg gag aag aag gca act gag     192
Met Asn Pro Met Cys Ile Tyr Arg Ser Pro Glu Lys Lys Ala Thr Glu
50                  55                  60 gat gag ggc tca gaa cag aag atc ccg gag gcc acc aac cgg cgt gtc     240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag     288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc     336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat     384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct     432
Asp Thr Leu Gln Gln Leu Met Glu Val Phe Lys Phe Asp Thr Ile Ser
130                 135                 140 gag aaa aca tct gat cag atc cac ttc ttc ttt gcc aaa ctg aac tgc     480
Glu Lys Thr Ser Asp Gln Ile His Phe Phe Phe Ala Lys Leu Asn Cys
145                 150                 155                 160 cga ctc tat cga aaa gcc cag aaa tcc tcc aag tta gta tca gcc aat     528
Arg Leu Tyr Arg Lys Ala Gln Lys Ser Ser Lys Leu Val Ser Ala Asn
                165                 170                 175 cgc ctt ttt gga gac aaa tcc ctt acc ttc aat gag acc tac cag gac     576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag     624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat     672
Glu Asn Ala Glu Gln Ser Arg Ala Ala Ile Asn Lys Trp Val Ser Asn
```

-continued

```
              210                 215                 220
aag acc gaa ggc cga atc acc gat gtc att ccc tcg gaa gcc atc aat    720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg    768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac    816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc    864
Lys Ala Asp Gly Glu Ser Cys Ser Ala Ser Met Met Tyr Gln Glu Gly
        275                 280                 285 aag ttc cgt tat cgg cgc gtg gct gaa ggc acc cag gtg ctt gag ttg    912
Lys Phe Arg Tyr Arg Arg Val Ala Glu Gly Thr Gln Val Leu Glu Leu
    290                 295                 300 ccc ttc aaa ggt gat gac atc acc atg gtc ctc atc ttg ccc aag cct    960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg   1008
Glu Lys Ser Leu Ala Lys Val Glu Lys Glu Leu Thr Pro Glu Val Leu
                325                 330                 335 caa gag tgg ctg gat gaa ttg gag gag atg atg ctg gtg gtc cac atg   1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa   1104
Pro Arg Phe Arg Ile Glu Asp Gly Phe Ser Leu Lys Glu Gln Leu Gln
        355                 360                 365 gac atg ggc ctt gtc gat ctg ttc agc cct gaa aag tcc aaa ctc cca   1152
Asp Met Gly Leu Val Asp Leu Phe Ser Pro Glu Lys Ser Lys Leu Pro
    370                 375                 380 ggt att gtt gca gaa ggc cga gat gac ctc tat gtc tca gat gca ttc   1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca   1248
His Lys Ala Phe Leu Glu Val Asn Glu Glu Gly Ser Glu Ala Ala Ala
                405                 410                 415 agt acc gct gtt gtg att gct ggc cgt cca tcg cta aac ccc aac agg   1296
Ser Thr Ala Val Val Ile Ala Gly Arg Pro Ser Leu Asn Pro Asn Arg
            420                 425                 430 gtg act ttc aag gcc aac agg cct ttc ctg gtt ttt ata aga gaa gtt   1344
Val Thr Phe Lys Ala Asn Arg Pro Phe Leu Val Phe Ile Arg Glu Val
        435                 440                 445 cct ctg aac act att atc ttc atg ggc aga gta gcc aac cct tgt gtt   1392
Pro Leu Asn Thr Ile Ile Phe Met Gly Arg Val Ala Asn Pro Cys Val
    450                 455                 460 aag taaaatgttc ttattctttg cacctcttcc tattttggt ttgtgaacag         1445
Lys
465 aagtaaaaat aaatacaaac tacttccatc tcacattaaa a                     1486
```

<210> SEQ ID NO 40
<211> LENGTH: 465
<212> TYPE: PRT
<213> ORGANISM: Homo sapiens

<400> SEQUENCE: 40

```
Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
```

-continued

```
                    20                  25                  30
His Gly Ser Pro Val Asp Ile Cys Thr Ala Lys Pro Arg Asp Ile Pro
                35                  40                  45
Met Asn Pro Met Cys Ile Tyr Arg Ser Pro Glu Lys Lys Ala Thr Glu
            50                  55                  60
Asp Glu Gly Ser Glu Gln Lys Ile Pro Glu Ala Thr Asn Arg Arg Val
65                  70                  75                  80
Trp Glu Leu Ser Lys Ala Asn Ser Arg Phe Ala Thr Thr Phe Tyr Gln
                85                  90                  95
His Leu Ala Asp Ser Lys Asn Asp Asn Asp Asn Ile Phe Leu Ser Pro
            100                 105                 110
Leu Ser Ile Ser Thr Ala Phe Ala Met Thr Lys Leu Gly Ala Cys Asn
            115                 120                 125
Asp Thr Leu Gln Gln Leu Met Glu Val Phe Lys Phe Asp Thr Ile Ser
            130                 135                 140
Glu Lys Thr Ser Asp Gln Ile His Phe Phe Ala Lys Leu Asn Cys
145                 150                 155                 160
Arg Leu Tyr Arg Lys Ala Gln Lys Ser Ser Lys Leu Val Ser Ala Asn
                165                 170                 175
Arg Leu Phe Gly Asp Lys Ser Leu Thr Phe Asn Glu Thr Tyr Gln Asp
                180                 185                 190
Ile Ser Glu Leu Val Tyr Gly Ala Lys Leu Gln Pro Leu Asp Phe Lys
            195                 200                 205
Glu Asn Ala Glu Gln Ser Arg Ala Ala Ile Asn Lys Trp Val Ser Asn
            210                 215                 220
Lys Thr Glu Gly Arg Ile Thr Asp Val Ile Pro Ser Glu Ala Ile Asn
225                 230                 235                 240
Glu Leu Thr Val Leu Val Leu Val Asn Thr Ile Tyr Phe Lys Gly Leu
                245                 250                 255
Trp Lys Ser Lys Phe Ser Pro Glu Asn Thr Arg Lys Glu Leu Phe Tyr
                260                 265                 270
Lys Ala Asp Gly Glu Ser Cys Ser Ala Ser Met Met Tyr Gln Glu Gly
            275                 280                 285
Lys Phe Arg Tyr Arg Arg Val Ala Glu Gly Thr Gln Val Leu Glu Leu
            290                 295                 300
Pro Phe Lys Gly Asp Asp Ile Thr Met Val Leu Ile Leu Pro Lys Pro
305                 310                 315                 320
Glu Lys Ser Leu Ala Lys Val Glu Lys Glu Leu Thr Pro Glu Val Leu
                325                 330                 335
Gln Glu Trp Leu Asp Glu Leu Glu Glu Met Met Leu Val Val His Met
                340                 345                 350
Pro Arg Phe Arg Ile Glu Asp Gly Phe Ser Leu Lys Glu Gln Leu Gln
            355                 360                 365
Asp Met Gly Leu Val Asp Leu Phe Ser Pro Glu Lys Ser Lys Leu Pro
            370                 375                 380
Gly Ile Val Ala Glu Gly Arg Asp Asp Leu Tyr Val Ser Asp Ala Phe
385                 390                 395                 400
His Lys Ala Phe Leu Glu Val Asn Glu Glu Gly Ser Glu Ala Ala Ala
                405                 410                 415
Ser Thr Ala Val Val Ile Ala Gly Arg Pro Ser Leu Asn Pro Asn Arg
            420                 425                 430
Val Thr Phe Lys Ala Asn Arg Pro Phe Leu Val Phe Ile Arg Glu Val
            435                 440                 445
```

```
Pro Leu Asn Thr Ile Ile Phe Met Gly Arg Val Ala Asn Pro Cys Val
    450                 455                 460
Lys
465

<210> SEQ ID NO 41
<211> LENGTH: 1477
<212> TYPE: DNA
<213> ORGANISM: Homo sapiens
<220> FEATURE:
<221> NAME/KEY: CDS
<222> LOCATION: (1)..(1386)

<400> SEQUENCE: 41 atg tat tcc aat gtg ata gga act gta acc tct gga aaa agg aag gtt     48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt     96
Tyr Leu Leu Ser Leu Leu Leu Ile Gly Phe Trp Asp Cys Val Thr Cys
                20                  25                  30 cac ggg agc cct gtg gac atc tgc aca gcc aag ccg cgg gac att ccc    144
His Gly Ser Pro Val Asp Ile Cys Thr Ala Lys Pro Arg Asp Ile Pro
            35                  40                  45 atg aat ccc atg tgc att tac cgc tcc ccg gag aag aag gca act gag    192
Met Asn Pro Met Cys Ile Tyr Arg Ser Pro Glu Lys Lys Ala Thr Glu
        50                  55                  60 gat gag ggc tca gaa cag aag atc ccg gag gcc acc aac cgg cgt gtc    240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag    288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc    336
His Leu Ala Asp Ser Lys Asn Asp Asn Asp Asn Ile Phe Leu Ser Pro
                100                 105                 110 ctg agt atc tcc acg gct ttt gct atg acc aag ctg ggt gcc tgt aat    384
Leu Ser Ile Ser Thr Ala Phe Ala Met Thr Lys Leu Gly Ala Cys Asn
            115                 120                 125 gac acc ctc cag caa ctg atg gag gta ttt aag ttt gac acc ata tct    432
Asp Thr Leu Gln Gln Leu Met Glu Val Phe Lys Phe Asp Thr Ile Ser
        130                 135                 140 gag aaa aca tct gat cag atc cac ttc ttc ttt gcc aaa ctg aac tgc    480
Glu Lys Thr Ser Asp Gln Ile His Phe Phe Phe Ala Lys Leu Asn Cys
145                 150                 155                 160 cga ctc tat cga aaa gcc aac aaa tcc tcc aag tta gta tca gcc aat    528
Arg Leu Tyr Arg Lys Ala Asn Lys Ser Ser Lys Leu Val Ser Ala Asn
                165                 170                 175 cgc ctt ttt gga gac aaa tcc ctt acc ttc aat gag acc tac cag gac    576
Arg Leu Phe Gly Asp Lys Ser Leu Thr Phe Asn Glu Thr Tyr Gln Asp
                180                 185                 190 atc agt gag ttg gta tat gga gcc aag ctc cag ccc ctg gac ttc aag    624
Ile Ser Glu Leu Val Tyr Gly Ala Lys Leu Gln Pro Leu Asp Phe Lys
            195                 200                 205 gaa aat gca gag caa tcc aga gcg gcc atc aac aaa tgg gtg tcc aat    672
Glu Asn Ala Glu Gln Ser Arg Ala Ala Ile Asn Lys Trp Val Ser Asn
        210                 215                 220 aag acc gaa ggc cga atc acc gat gtc att ccc tcg gaa gcc atc aat    720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg    768
Glu Leu Thr Val Leu Val Leu Val Asn Thr Ile Tyr Phe Lys Gly Leu
                245                 250                 255
```

-continued

| | | |
|---|---|---|
| tgg aag tca aag ttc agc cct gag aac aca agg aag gaa ctg ttc tac<br>Trp Lys Ser Lys Phe Ser Pro Glu Asn Thr Arg Lys Glu Leu Phe Tyr<br>260                     265                          270 | | 816 |
| aag gct gat gga gag tcg tgt tca gca tct atg atg tac cag gaa ggc<br>Lys Ala Asp Gly Glu Ser Cys Ser Ala Ser Met Met Tyr Gln Glu Gly<br>          275                      280                     285 | | 864 |
| aag ttc cgt tat cgg cgc gtg gct gaa ggc acc cag gtg ctt gag ttg<br>Lys Phe Arg Tyr Arg Arg Val Ala Glu Gly Thr Gln Val Leu Glu Leu<br>290                     295                          300 | | 912 |
| ccc ttc aaa ggt gat gac atc acc atg gtc ctc atc ttg ccc aag cct<br>Pro Phe Lys Gly Asp Asp Ile Thr Met Val Leu Ile Leu Pro Lys Pro<br>305                     310                      315                   320 | | 960 |
| gag aag agc ctg gcc aag gta gag aag gaa ctc acc cca gag gtg ctg<br>Glu Lys Ser Leu Ala Lys Val Glu Lys Glu Leu Thr Pro Glu Val Leu<br>                   325                      330                      335 | | 1008 |
| caa gag tgg ctg gat gaa ttg gag gag atg atg ctg gtg gtc cac atg<br>Gln Glu Trp Leu Asp Glu Leu Glu Glu Met Met Leu Val Val His Met<br>                 340                      345                      350 | | 1056 |
| ccc cgc ttc cgc att gag gac ggc ttc agt ttg aag gag cag ctg caa<br>Pro Arg Phe Arg Ile Glu Asp Gly Phe Ser Leu Lys Glu Gln Leu Gln<br>             355                      360                      365 | | 1104 |
| gac atg ggc ctt gtc gat ctg ttc agc cct gaa aag tcc aaa ctc cca<br>Asp Met Gly Leu Val Asp Leu Phe Ser Pro Glu Lys Ser Lys Leu Pro<br>370                     375                      380 | | 1152 |
| ggt att gtt gca gaa ggc cga gat gac ctc tat gtc tca gat gca ttc<br>Gly Ile Val Ala Glu Gly Arg Asp Asp Leu Tyr Val Ser Asp Ala Phe<br>385                     390                     395                   400 | | 1200 |
| cat aag gca ttt ctt gag gta aat gaa gaa ggc agt gaa gca gct gca<br>His Lys Ala Phe Leu Glu Val Asn Glu Glu Gly Ser Glu Ala Ala Ala<br>                 405                      410                      415 | | 1248 |
| agt acc gct gtt gtg att gct ggc cta aac ccc aac agg gtg act ttc<br>Ser Thr Ala Val Val Ile Ala Gly Leu Asn Pro Asn Arg Val Thr Phe<br>                   420                      425                      430 | | 1296 |
| aag gcc aac agg cct ttc ctg gtt ttt ata aga gaa gtt cct ctg aac<br>Lys Ala Asn Arg Pro Phe Leu Val Phe Ile Arg Glu Val Pro Leu Asn<br>             435                      440                      445 | | 1344 |
| act att atc ttc atg ggc aga gta gcc aac cct tgt gtt aag<br>Thr Ile Ile Phe Met Gly Arg Val Ala Asn Pro Cys Val Lys<br>450                     455                     460 | | 1386 |
| taaaatgttc ttattctttg cacctcttcc tattttggt ttgtgaacag aagtaaaaat | | 1446 |
| aaatacaaac tacttccatc tcacattaaa a | | 1477 |

<210> SEQ ID NO 42
<211> LENGTH: 462
<212> TYPE: PRT
<213> ORGANISM: Homo sapiens

<400> SEQUENCE: 42

Met Tyr Ser Asn Val Ile Gly Thr Val Thr Ser Gly Lys Arg Lys Val
1               5                   10                 15

Tyr Leu Leu Ser Leu Leu Leu Ile Gly Phe Trp Asp Cys Val Thr Cys
                 20                      25                     30

His Gly Ser Pro Val Asp Ile Cys Thr Ala Lys Pro Arg Asp Ile Pro
             35                      40                      45

Met Asn Pro Met Cys Ile Tyr Arg Ser Pro Glu Lys Lys Ala Thr Glu
     50                   55                   60

Asp Glu Gly Ser Glu Gln Lys Ile Pro Glu Ala Thr Asn Arg Arg Val
65                   70                     75                   80

```
Trp Glu Leu Ser Lys Ala Asn Ser Arg Phe Ala Thr Thr Phe Tyr Gln
                85                  90                  95

His Leu Ala Asp Ser Lys Asn Asp Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Ala Lys Leu Asn Cys
145                 150                 155                 160

Arg Leu Tyr Arg Lys Ala Asn Lys Ser Lys Leu Val Ser Ala Asn
            165                 170                 175

Arg Leu Phe Gly Asp Lys Ser Leu Thr Phe Asn Glu Thr Tyr Gln Asp
        180                 185                 190

Ile Ser Glu Leu Val Tyr Gly Ala Lys Leu Gln Pro Leu Asp Phe Lys
    195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
            245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
        290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
            325                 330                 335

Gln Glu Trp Leu Asp Glu Leu Glu Glu Met Met Leu Val Val His Met
        340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
            405                 410                 415

Ser Thr Ala Val Val Ile Ala Gly Leu Asn Pro Asn Arg Val Thr Phe
        420                 425                 430

Lys Ala Asn Arg Pro Phe Leu Val Phe Ile Arg Glu Val Pro Leu Asn
        435                 440                 445

Thr Ile Ile Phe Met Gly Arg Val Ala Asn Pro Cys Val Lys
    450                 455                 460

<210> SEQ ID NO 43
<211> LENGTH: 1480
<212> TYPE: DNA
<213> ORGANISM: Homo sapiens
<220> FEATURE:
<221> NAME/KEY: CDS
<222> LOCATION: (1)..(1389)
```

<400> SEQUENCE: 43

| | | | | | | | | | | | | | | | | |
|---|---|---|---|---|---|---|---|---|---|---|---|---|---|---|---|---|
| atg | tat | tcc | aat | gtg | ata | gga | act | gta | acc | tct | gga | aaa | agg | aag | gtt | 48 |
| Met | Tyr | Ser | Asn | Val | Ile | Gly | Thr | Val | Thr | Ser | Gly | Lys | Arg | Lys | Val | |
| 1 | | | | 5 | | | | | 10 | | | | | 15 | | |
| tat | ctt | ttg | tcc | ttg | ctg | ctc | att | ggc | ttc | tgg | gac | tgc | gtg | acc | tgt | 96 |
| Tyr | Leu | Leu | Ser | Leu | Leu | Leu | Ile | Gly | Phe | Trp | Asp | Cys | Val | Thr | Cys | |
| | | | 20 | | | | | 25 | | | | | 30 | | | |
| cac | ggg | agc | cct | gtg | gac | atc | tgc | aca | gcc | aag | ccg | cgg | gac | att | ccc | 144 |
| His | Gly | Ser | Pro | Val | Asp | Ile | Cys | Thr | Ala | Lys | Pro | Arg | Asp | Ile | Pro | |
| | | 35 | | | | | 40 | | | | | 45 | | | | |
| atg | aat | ccc | atg | tgc | att | tac | cgc | tcc | ccg | gag | aag | aag | gca | act | gag | 192 |
| Met | Asn | Pro | Met | Cys | Ile | Tyr | Arg | Ser | Pro | Glu | Lys | Lys | Ala | Thr | Glu | |
| | 50 | | | | | 55 | | | | | 60 | | | | | |
| gat | gag | ggc | tca | gaa | cag | aag | atc | ccg | gag | gcc | acc | aac | cgg | cgt | gtc | 240 |
| Asp | Glu | Gly | Ser | Glu | Gln | Lys | Ile | Pro | Glu | Ala | Thr | Asn | Arg | Arg | Val | |
| 65 | | | | | 70 | | | | | 75 | | | | | 80 | |
| tgg | gaa | ctg | tcc | aag | gcc | aat | tcc | cgc | ttt | gct | acc | act | ttc | tat | cag | 288 |
| Trp | Glu | Leu | Ser | Lys | Ala | Asn | Ser | Arg | Phe | Ala | Thr | Thr | Phe | Tyr | Gln | |
| | | | | 85 | | | | | 90 | | | | | 95 | | |
| cac | ctg | gca | gat | tcc | aag | aat | gac | aat | gat | aac | att | ttc | ctg | tca | ccc | 336 |
| His | Leu | Ala | Asp | Ser | Lys | Asn | Asp | Asn | Asp | Asn | Ile | Phe | Leu | Ser | Pro | |
| | | | 100 | | | | | 105 | | | | | 110 | | | |
| ctg | agt | atc | tcc | acg | gct | ttt | gct | atg | acc | aag | ctg | ggt | gcc | tgt | aat | 384 |
| Leu | Ser | Ile | Ser | Thr | Ala | Phe | Ala | Met | Thr | Lys | Leu | Gly | Ala | Cys | Asn | |
| | | 115 | | | | | 120 | | | | | 125 | | | | |
| gac | acc | ctc | cag | caa | ctg | atg | gag | gta | ttt | aag | ttt | gac | acc | ata | tct | 432 |
| Asp | Thr | Leu | Gln | Gln | Leu | Met | Glu | Val | Phe | Lys | Phe | Asp | Thr | Ile | Ser | |
| | 130 | | | | | 135 | | | | | 140 | | | | | |
| gag | aaa | aca | tct | gat | cag | atc | cac | ttc | ttc | ttt | gcc | aaa | ctg | aac | tgc | 480 |
| Glu | Lys | Thr | Ser | Asp | Gln | Ile | His | Phe | Phe | Phe | Ala | Lys | Leu | Asn | Cys | |
| 145 | | | | | 150 | | | | | 155 | | | | | 160 | |
| cga | ctc | tat | cga | aaa | gcc | cag | aaa | tcc | tcc | aag | tta | gta | tca | gcc | aat | 528 |
| Arg | Leu | Tyr | Arg | Lys | Ala | Gln | Lys | Ser | Ser | Lys | Leu | Val | Ser | Ala | Asn | |
| | | | | 165 | | | | | 170 | | | | | 175 | | |
| cgc | ctt | ttt | gga | gac | aaa | tcc | ctt | acc | ttc | aat | gag | acc | tac | cag | gac | 576 |
| Arg | Leu | Phe | Gly | Asp | Lys | Ser | Leu | Thr | Phe | Asn | Glu | Thr | Tyr | Gln | Asp | |
| | | | 180 | | | | | 185 | | | | | 190 | | | |
| atc | agt | gag | ttg | gta | tat | gga | gcc | aag | ctc | cag | ccc | ctg | gac | ttc | aag | 624 |
| Ile | Ser | Glu | Leu | Val | Tyr | Gly | Ala | Lys | Leu | Gln | Pro | Leu | Asp | Phe | Lys | |
| | | 195 | | | | | 200 | | | | | 205 | | | | |
| gaa | aat | gca | gag | caa | tcc | aga | gcg | gcc | atc | aac | aaa | tgg | gtg | tcc | aat | 672 |
| Glu | Asn | Ala | Glu | Gln | Ser | Arg | Ala | Ala | Ile | Asn | Lys | Trp | Val | Ser | Asn | |
| | 210 | | | | | 215 | | | | | 220 | | | | | |
| aag | acc | gaa | ggc | cga | atc | acc | gat | gtc | att | ccc | tcg | gaa | gcc | atc | aat | 720 |
| Lys | Thr | Glu | Gly | Arg | Ile | Thr | Asp | Val | Ile | Pro | Ser | Glu | Ala | Ile | Asn | |
| 225 | | | | | 230 | | | | | 235 | | | | | 240 | |
| gag | ctc | act | gtt | ctg | gtg | ctg | gtt | aac | acc | att | tac | ttc | aag | ggc | ctg | 768 |
| Glu | Leu | Thr | Val | Leu | Val | Leu | Val | Asn | Thr | Ile | Tyr | Phe | Lys | Gly | Leu | |
| | | | | 245 | | | | | 250 | | | | | 255 | | |
| tgg | aag | tca | aag | ttc | agc | cct | gag | aac | aca | agg | aag | gaa | ctg | ttc | tac | 816 |
| Trp | Lys | Ser | Lys | Phe | Ser | Pro | Glu | Asn | Thr | Arg | Lys | Glu | Leu | Phe | Tyr | |
| | | | 260 | | | | | 265 | | | | | 270 | | | |
| aag | gct | gat | gga | gag | tcg | tgt | tca | gca | tct | atg | atg | tac | cag | gaa | ggc | 864 |
| Lys | Ala | Asp | Gly | Glu | Ser | Cys | Ser | Ala | Ser | Met | Met | Tyr | Gln | Glu | Gly | |
| | | 275 | | | | | 280 | | | | | 285 | | | | |
| aag | ttc | cgt | tat | cgg | cgc | gtg | gct | gaa | ggc | acc | cag | gtg | ctt | gag | ttg | 912 |
| Lys | Phe | Arg | Tyr | Arg | Arg | Val | Ala | Glu | Gly | Thr | Gln | Val | Leu | Glu | Leu | |
| | 290 | | | | | 295 | | | | | 300 | | | | | |
| ccc | ttc | aaa | ggt | gat | gac | atc | acc | atg | gtc | ctc | atc | ttg | ccc | aag | cct | 960 |

-continued

```
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg      1008
Glu Lys Ser Leu Ala Lys Val Glu Lys Glu Leu Thr Pro Glu Val Leu
                325                 330                 335 caa gag tgg ctg gat gaa ttg gag gag atg atg ctg gtg gtc cac atg      1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa      1104
Pro Arg Phe Arg Ile Glu Asp Gly Phe Ser Leu Lys Glu Gln Leu Gln
        355                 360                 365 gac atg ggc ctt gtc gat ctg ttc agc cct gaa aag tcc aaa ctc cca      1152
Asp Met Gly Leu Val Asp Leu Phe Ser Pro Glu Lys Ser Lys Leu Pro
    370                 375                 380 ggt att gtt gca gaa ggc cga gat gac ctc tat gtc tca gat gca ttc      1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca      1248
His Lys Ala Phe Leu Glu Val Asn Glu Glu Gly Ser Glu Ala Ala Ala
                405                 410                 415 agt acc gct gtt gtg att gct ggc tcg cta aac ccc aac agg gtg act      1296
Ser Thr Ala Val Val Ile Ala Gly Ser Leu Asn Pro Asn Arg Val Thr
            420                 425                 430 ttc aag gcc aac agg cct ttc ctg gtt ttt ata aga gaa gtt cct ctg      1344
Phe Lys Ala Asn Arg Pro Phe Leu Val Phe Ile Arg Glu Val Pro Leu
        435                 440                 445 aac act att atc ttc atg ggc aga gta gcc aac cct tgt gtt aag          1389
Asn Thr Ile Ile Phe Met Gly Arg Val Ala Asn Pro Cys Val Lys
    450                 455                 460 taaaatgttc ttattctttg cacctcttcc tattttggt ttgtgaacag aagtaaaaat    1449
aaatacaaac tacttccatc tcacattaaa a                                   1480
```

<210> SEQ ID NO 44
<211> LENGTH: 463
<212> TYPE: PRT
<213> ORGANISM: Homo sapiens

<400> SEQUENCE: 44

```
Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160
```

```
Arg Leu Tyr Arg Lys Ala Gln Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Ser Leu Asn Pro Asn Arg Val Thr
            420                 425                 430

Phe Lys Ala Asn Arg Pro Phe Leu Val Phe Ile Arg Glu Val Pro Leu
        435                 440                 445

Asn Thr Ile Ile Phe Met Gly Arg Val Ala Asn Pro Cys Val Lys
    450                 455                 460

<210> SEQ ID NO 45
<211> LENGTH: 1480
<212> TYPE: DNA
<213> ORGANISM: Homo sapiens
<220> FEATURE:
<221> NAME/KEY: CDS
<222> LOCATION: (1)..(1389)

<400> SEQUENCE: 45 atg tat tcc aat gtg ata gga act gta acc tct gga aaa agg aag gtt        48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt        96
Tyr Leu Leu Ser Leu Leu Leu Ile Gly Phe Trp Asp Cys Val Thr Cys
            20                  25                  30 cac ggg agc cct gtg gac atc tgc aca gcc aag ccg cgg gac att ccc       144
His Gly Ser Pro Val Asp Ile Cys Thr Ala Lys Pro Arg Asp Ile Pro
        35                  40                  45
```

```
atg aat ccc atg tgc att tac cgc tcc ccg gag aag aag gca act gag      192
Met Asn Pro Met Cys Ile Tyr Arg Ser Pro Glu Lys Lys Ala Thr Glu
 50                  55                  60 gat gag ggc tca gaa cag aag atc ccg gag gcc acc aac cgg cgt gtc      240
Asp Glu Gly Ser Glu Gln Lys Ile Pro Glu Ala Thr Asn Arg Arg Val
 65                  70                  75                  80 tgg gaa ctg tcc aag gcc aat tcc cgc ttt gct acc act ttc tat cag      288
Trp Glu Leu Ser Lys Ala Asn Ser Arg Phe Ala Thr Thr Phe Tyr Gln
                 85                  90                  95 cac ctg gca gat tcc aag aat gac aat gat aac att ttc ctg tca ccc      336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat      384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct      432
Asp Thr Leu Gln Gln Leu Met Glu Val Phe Lys Phe Asp Thr Ile Ser
130                 135                 140 gag aaa aca tct gat cag atc cac ttc ttc ttt gcc aaa ctg aac tgc      480
Glu Lys Thr Ser Asp Gln Ile His Phe Phe Phe Ala Lys Leu Asn Cys
145                 150                 155                 160 cga ctc tat cga aaa gcc cag aaa tcc tcc aag tta gta tca gcc aat      528
Arg Leu Tyr Arg Lys Ala Gln Lys Ser Ser Lys Leu Val Ser Ala Asn
                165                 170                 175 cgc ctt ttt gga gac aaa tcc ctt acc ttc aat gag acc tac cag gac      576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag      624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat      672
Glu Asn Ala Glu Gln Ser Arg Ala Ala Ile Asn Lys Trp Val Ser Asn
210                 215                 220 aag acc gaa ggc cga atc acc gat gtc att ccc tcg gaa gcc atc aat      720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg      768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac      816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc      864
Lys Ala Asp Gly Glu Ser Cys Ser Ala Ser Met Met Tyr Gln Glu Gly
        275                 280                 285 aag ttc cgt tat cgg cgc gtg gct gaa ggc acc cag gtg ctt gag ttg      912
Lys Phe Arg Tyr Arg Arg Val Ala Glu Gly Thr Gln Val Leu Glu Leu
290                 295                 300 ccc ttc aaa ggt gat gac atc acc atg gtc ctc atc ttg ccc aag cct      960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg     1008
Glu Lys Ser Leu Ala Lys Val Glu Lys Glu Leu Thr Pro Glu Val Leu
                325                 330                 335 caa gag tgg ctg gat gaa ttg gag gag atg atg ctg gtg gtc cac atg     1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa     1104
Pro Arg Phe Arg Ile Glu Asp Gly Phe Ser Leu Lys Glu Gln Leu Gln
        355                 360                 365
```

```
gac atg ggc ctt gtc gat ctg ttc agc cct gaa aag tcc aaa ctc cca      1152
Asp Met Gly Leu Val Asp Leu Phe Ser Pro Glu Lys Ser Lys Leu Pro
370                 375                 380 ggt att gtt gca gaa ggc cga gat gac ctc tat gtc tca gat gca ttc      1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca      1248
His Lys Ala Phe Leu Glu Val Asn Glu Glu Gly Ser Glu Ala Ala Ala
            405                 410                 415 agt acc gct gtt gtg att gct ggc cgt cta aac ccc aac agg gtg act      1296
Ser Thr Ala Val Val Ile Ala Gly Arg Leu Asn Pro Asn Arg Val Thr
420                 425                 430 ttc aag gcc aac agg cct ttc ctg gtt ttt ata aga gaa gtt cct ctg      1344
Phe Lys Ala Asn Arg Pro Phe Leu Val Phe Ile Arg Glu Val Pro Leu
435                 440                 445 aac act att atc ttc atg ggc aga gta gcc aac cct tgt gtt aag          1389
Asn Thr Ile Ile Phe Met Gly Arg Val Ala Asn Pro Cys Val Lys
450                 455                 460 taaaatgttc ttattctttg cacctcttcc tattttttggt ttgtgaacag aagtaaaaat   1449
aaatacaaac tacttccatc tcacattaaa a                                   1480

<210> SEQ ID NO 46
<211> LENGTH: 463
<212> TYPE: PRT
<213> ORGANISM: Homo sapiens

<400> SEQUENCE: 46

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Ala Lys Leu Asn Cys
145                 150                 155                 160

Arg Leu Tyr Arg Lys Ala Gln Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
```

```
                225                 230                 235                 240
Glu Leu Thr Val Leu Val Leu Val Asn Thr Ile Tyr Phe Lys Gly Leu
                245                 250                 255
Trp Lys Ser Lys Phe Ser Pro Glu Asn Thr Arg Lys Glu Leu Phe Tyr
                260                 265                 270
Lys Ala Asp Gly Glu Ser Cys Ser Ala Ser Met Met Tyr Gln Glu Gly
                275                 280                 285
Lys Phe Arg Tyr Arg Arg Val Ala Glu Gly Thr Gln Val Leu Glu Leu
                290                 295                 300
Pro Phe Lys Gly Asp Asp Ile Thr Met Val Leu Ile Leu Pro Lys Pro
305                 310                 315                 320
Glu Lys Ser Leu Ala Lys Val Glu Lys Glu Leu Thr Pro Glu Val Leu
                325                 330                 335
Gln Glu Trp Leu Asp Glu Leu Glu Glu Met Met Leu Val Val His Met
                340                 345                 350
Pro Arg Phe Arg Ile Glu Asp Gly Phe Ser Leu Lys Glu Gln Leu Gln
                355                 360                 365
Asp Met Gly Leu Val Asp Leu Phe Ser Pro Glu Lys Ser Lys Leu Pro
                370                 375                 380
Gly Ile Val Ala Glu Gly Arg Asp Asp Leu Tyr Val Ser Asp Ala Phe
385                 390                 395                 400
His Lys Ala Phe Leu Glu Val Asn Glu Glu Gly Ser Glu Ala Ala Ala
                405                 410                 415
Ser Thr Ala Val Val Ile Ala Gly Arg Leu Asn Pro Asn Arg Val Thr
                420                 425                 430
Phe Lys Ala Asn Arg Pro Phe Leu Val Phe Ile Arg Glu Val Pro Leu
                435                 440                 445
Asn Thr Ile Ile Phe Met Gly Arg Val Ala Asn Pro Cys Val Lys
                450                 455                 460

<210> SEQ ID NO 47
<211> LENGTH: 1477
<212> TYPE: DNA
<213> ORGANISM: Homo sapiens
<220> FEATURE:
<221> NAME/KEY: CDS
<222> LOCATION: (1)..(1386)

<400> SEQUENCE: 47 atg tat tcc aat gtg ata gga act gta acc tct gga aaa agg aag gtt      48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt      96
Tyr Leu Leu Ser Leu Leu Leu Ile Gly Phe Trp Asp Cys Val Thr Cys
            20                  25                  30 cac ggg agc cct gtg gac atc tgc aca gcc aag ccg cgg gac att ccc     144
His Gly Ser Pro Val Asp Ile Cys Thr Ala Lys Pro Arg Asp Ile Pro
        35                  40                  45 atg aat ccc atg tgc att tac cgc tcc ccg gag aag aag gca act gag     192
Met Asn Pro Met Cys Ile Tyr Arg Ser Pro Glu Lys Lys Ala Thr Glu
    50                  55                  60 gat gag ggc tca gaa cag aag atc ccg gag gcc acc aac cgg cgt gtc     240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag     288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc     336
```

```
            His Leu Ala Asp Ser Lys Asn Asp Asn Asp Asn Ile Phe Leu Ser Pro
                        100                 105                 110 ctg agt atc tcc acg gct ttt gct atg acc aag ctg ggt gcc tgt aat        384
Leu Ser Ile Ser Thr Ala Phe Ala Met Thr Lys Leu Gly Ala Cys Asn
            115                 120                 125 gac acc ctc cag caa ctg atg gag gta ttt aag ttt gac acc ata tct        432
Asp Thr Leu Gln Gln Leu Met Glu Val Phe Lys Phe Asp Thr Ile Ser
            130                 135                 140 gag aaa aca tct gat cag atc cac ttc ttc ttt gcc aaa ctg aac tgc        480
Glu Lys Thr Ser Asp Gln Ile His Phe Phe Phe Ala Lys Leu Asn Cys
145                 150                 155                 160 cga ctc tat cga aaa gcc cag aaa tcc tcc aag tta gta tca gcc aat        528
Arg Leu Tyr Arg Lys Ala Gln Lys Ser Ser Lys Leu Val Ser Ala Asn
                165                 170                 175 cgc ctt ttt gga gac aaa tcc ctt acc ttc aat gag acc tac cag gac        576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag        624
Ile Ser Glu Leu Val Tyr Gly Ala Lys Leu Gln Pro Leu Asp Phe Lys
            195                 200                 205 gaa aat gca gag caa tcc aga gcg gcc atc aac aaa tgg gtg tcc aat        672
Glu Asn Ala Glu Gln Ser Arg Ala Ala Ile Asn Lys Trp Val Ser Asn
            210                 215                 220 aag acc gaa ggc cga atc acc gat gtc att ccc tcg gaa gcc atc aat        720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg        768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac        816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc        864
Lys Ala Asp Gly Glu Ser Cys Ser Ala Ser Met Met Tyr Gln Glu Gly
            275                 280                 285 aag ttc cgt tat cgg cgc gtg gct gaa ggc acc cag gtg ctt gag ttg        912
Lys Phe Arg Tyr Arg Arg Val Ala Glu Gly Thr Gln Val Leu Glu Leu
            290                 295                 300 ccc ttc aaa ggt gat gac atc acc atg gtc ctc atc ttg ccc aag cct        960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg       1008
Glu Lys Ser Leu Ala Lys Val Glu Lys Glu Leu Thr Pro Glu Val Leu
            325                 330                 335 caa gag tgg ctg gat gaa ttg gag gag atg atg ctg gtg gtc cac atg       1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa       1104
Pro Arg Phe Arg Ile Glu Asp Gly Phe Ser Leu Lys Glu Gln Leu Gln
            355                 360                 365 gac atg ggc ctt gtc gat ctg ttc agc cct gaa aag tcc aaa ctc cca       1152
Asp Met Gly Leu Val Asp Leu Phe Ser Pro Glu Lys Ser Lys Leu Pro
            370                 375                 380 ggt att gtt gca gaa ggc cga gat gac ctc tat gtc tca gat gca ttc       1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca       1248
His Lys Ala Phe Leu Glu Val Asn Glu Glu Gly Ser Glu Ala Ala Ala
                405                 410                 415 agt acc gct gtt gtg att gct ggc cta aac ccc aac agg gtg act ttc       1296
```

-continued

```
Ser Thr Ala Val Val Ile Ala Gly Leu Asn Pro Asn Arg Val Thr Phe
            420                 425                 430 aag gcc aac agg cct ttc ctg gtt ttt ata aga gaa gtt cct ctg aac    1344
Lys Ala Asn Arg Pro Phe Leu Val Phe Ile Arg Glu Val Pro Leu Asn
            435                 440                 445 act att atc ttc atg ggc aga gta gcc aac cct tgt gtt aag             1386
Thr Ile Ile Phe Met Gly Arg Val Ala Asn Pro Cys Val Lys
            450                 455                 460 taaaatgttc ttattctttg cacctcttcc tattttggt tgtgaacag aagtaaaaat    1446 aaatacaaac tacttccatc tcacattaaa a                                  1477

<210> SEQ ID NO 48
<211> LENGTH: 462
<212> TYPE: PRT
<213> ORGANISM: Homo sapiens

<400> SEQUENCE: 48

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160

Arg Leu Tyr Arg Lys Ala Gln Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300
```

```
Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
            325                 330                 335

Gln Glu Trp Leu Asp Glu Leu Glu Met Met Leu Val His Met
            340                 345                 350

Pro Arg Phe Arg Ile Glu Asp Gly Phe Ser Leu Lys Glu Gln Leu Gln
            355                 360                 365

Asp Met Gly Leu Val Asp Leu Phe Ser Pro Glu Lys Ser Lys Leu Pro
            370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
            405                 410                 415

Ser Thr Ala Val Val Ile Ala Gly Leu Asn Pro Asn Arg Val Thr Phe
            420                 425                 430

Lys Ala Asn Arg Pro Phe Leu Val Phe Ile Arg Glu Val Pro Leu Asn
            435                 440                 445

Thr Ile Ile Phe Met Gly Arg Val Ala Asn Pro Cys Val Lys
    450                 455                 460

<210> SEQ ID NO 49
<211> LENGTH: 41
<212> TYPE: DNA
<213> ORGANISM: Artificial
<220> FEATURE:
<223> OTHER INFORMATION: Forward primer

<400> SEQUENCE: 49
gccgactcta tcgaaaagcc cagaaatcct ccaagttagt g                 41

<210> SEQ ID NO 50
<211> LENGTH: 41
<212> TYPE: DNA
<213> ORGANISM: Artificial
<220> FEATURE:
<223> OTHER INFORMATION: Reverse primer

<400> SEQUENCE: 50
cactaacttg gaggatttct gggcttttcg atagagtcgg c                 41

<210> SEQ ID NO 51
<211> LENGTH: 33
<212> TYPE: DNA
<213> ORGANISM: Artificial
<220> FEATURE:
<223> OTHER INFORMATION: Forward primer

<400> SEQUENCE: 51
gttgtgattg ctggccattc gctaaacccc aac                          33

<210> SEQ ID NO 52
<211> LENGTH: 33
<212> TYPE: DNA
<213> ORGANISM: Artificial
<220> FEATURE:
<223> OTHER INFORMATION: Reverse primer

<400> SEQUENCE: 52
gttggggttt agcgaatggc cagcaatcac aac                          33

<210> SEQ ID NO 53
```

```
<211> LENGTH: 36
<212> TYPE: DNA
<213> ORGANISM: Artificial
<220> FEATURE:
<223> OTHER INFORMATION: Forward primer

<400> SEQUENCE: 53
gttgtgattg ctggccgtcc atcgctaaac cccaac                           36

<210> SEQ ID NO 54
<211> LENGTH: 36
<212> TYPE: DNA
<213> ORGANISM: Artificial
<220> FEATURE:
<223> OTHER INFORMATION: Reverse primer

<400> SEQUENCE: 54
gttggggttt agcgatggac ggccagcaat cacaac                           36

<210> SEQ ID NO 55
<211> LENGTH: 36
<212> TYPE: DNA
<213> ORGANISM: Artificial
<220> FEATURE:
<223> OTHER INFORMATION: Forward primer

<400> SEQUENCE: 55
gctgttgtga ttgctggcct aaacccaac agggtg                            36

<210> SEQ ID NO 56
<211> LENGTH: 36
<212> TYPE: DNA
<213> ORGANISM: Artificial
<220> FEATURE:
<223> OTHER INFORMATION: Reverse primer

<400> SEQUENCE: 56
caccctgttg ggtttaggc cagcaatcac aacagc                            36

<210> SEQ ID NO 57
<211> LENGTH: 34
<212> TYPE: DNA
<213> ORGANISM: Artificial
<220> FEATURE:
<223> OTHER INFORMATION: Forward primer

<400> SEQUENCE: 57
ctgttgtgat tgctggctcg ctaaacccca acag                             34

<210> SEQ ID NO 58
<211> LENGTH: 34
<212> TYPE: DNA
<213> ORGANISM: Artificial
<220> FEATURE:
<223> OTHER INFORMATION: Reverse primer

<400> SEQUENCE: 58
ctgttggggt ttagcgagcc agcaatcaca acag                             34

<210> SEQ ID NO 59
<211> LENGTH: 32
<212> TYPE: DNA
<213> ORGANISM: Artificial
<220> FEATURE:
<223> OTHER INFORMATION: Forward primer

<400> SEQUENCE: 59
```

```
tgtgattgct ggccgtctaa accccaacag gg                                    32
```

<210> SEQ ID NO 60
<211> LENGTH: 32
<212> TYPE: DNA
<213> ORGANISM: Artificial
<220> FEATURE:
<223> OTHER INFORMATION: Reverse primer

<400> SEQUENCE: 60

```
ccctgttggg gtttagacgg ccagcaatca ca                                    32
```

USE OF MUTATED ANTITHROMBINS FOR TREATING OR PREVENTING COAGULATION DISORDERS

Figure 1:
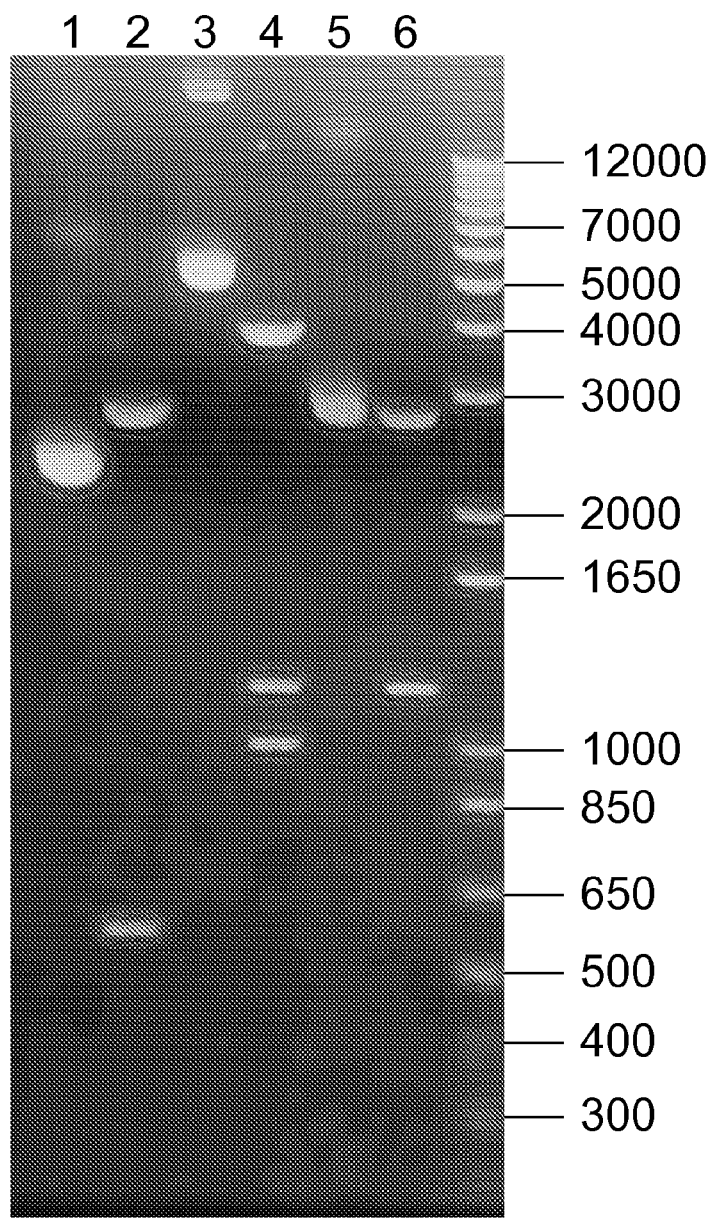

The present invention relates to the use of mutated antithrombins for treating or preventing coagulation disorders.

Antithrombin plays an essential role in maintaining the fluidity of blood. Blood coagulation is mediated by a series of serine proteases. Antithrombin is a potent inhibitor of Factors VIIa IXa, Xa, XIa, XIIa and IIa (thrombin).

The physiological importance of antithrombin in preventing excessive coagulation is revealed by studies of individuals whose antithrombin levels are decreased due to heredity or acquired deficiency. Such persons are prone spontaneous thrombosis and the associated risks of disseminated intravascular coagulation, cardiac infarction, cerebrovascular accident and pulmonary embolism.

It was well known that the therapeutic administration of anticoagulants (heparins, pentasaccharide Fondaparinux Arixtra® and pentasaccharide derivatives) prevents the formation of clots and the extension of existing clots within the blood and thus, is useful in the clinical prevention and management of venous thromboembolic disease.

The anticoagulant effect of antithrombin is enhanced by heparins and derivatives, in particular pentasaccharide, which greatly increases the rate of inhibitor-protease complex formation.

Only a fraction of heparin molecules are functional in this regard due to the presence in their structure of a specific pentasaccharide moiety capable of binding antithrombin with high affinity and inducing active conformational changes in the antithrombin.

The crystal structure of the free antithrombin and of antithrombin complexed with the above-mentioned pentasaccharide reveals that the pentasaccharide binding to an allosteric site on the inhibitor transmits conformational changes to a reactive proteinase binding loop on the inhibitor surface that enhances the loop accessibility to proteinases (Skinner, R., Abrahams, J-P., Whisstock, J. C., Lesk, A. M., Carrell, R. W., and Wardell, M. R. (1997) *J. Mol. Biol.* 266 601-609; Jin, L., Abrahams, J. P., Skinner, R., Petitou, M., Pike, R. N., and Carrell, R. W., (1997) *Proc. Natl. Acad. Sci., U.S.A.* 94, 14683-14688).

Heparin or the pentasaccharide is used as an anticoagulant in several clinical applications such as for treatment of various thrombotic diseases, unstable angina, and thrombosis prophylaxy in medical/surgical patients, for thrombosis management related to extracorporeal circulatory assistance or dialysis devices, for treatment of myocardial infarction (primarily and adjunctively with various thrombolytic agents).

However, the use of heparin can lead to undesired complications and in particular to hemorrhages. In some cases, this is due to the fact that the dosage of administered heparin is not appropriate, which might result in a limitation of the successful clinical use of heparin.

The only antidote available for heparin neutralisation is protamine. However, it is known that the protamine cannot neutralize the pentasaccharide (Giangrande P L. Fondaparinux (Arixtra): a new anticoagulant. *Int J Clin Pract* 2002; 56: 615-617), and is associated with various side effects (hemodynamic instability, anaphylactic shock and bleeding risk linked to an anticoagulant activity of protamine in case of overdosing), and in particular the administration of important doses of protamine increases the hemorrhage.

At this day, no completely suitable antidotes to heparin and to the pentasaccharide of heparin have been found and more particularly no suitable antidotes effective in vivo have been described, knowing that in the field of coagulation, in vitro tests are never sufficient to predict the in vivo effects.

For example, in the document (Krupinski et al. Antithrombotic effects of three thrombin inhibitors in a rat model of laser-induced thrombosis" *Haemostasis* 1989; 19 (2): 74-82) it is demonstrated that the anticoagulant effect of hirudin, NAPAP and argidipine do not differ in vitro, whereas ex vivo, the anticoagulant effect of hirudin is most important.

Another document (Yamashita et al. "The antithrombotic effect of potent bifunctional thrombin inhibitors based on hirudin sequence, P551 and P532, on He—Ne Laser induced thrombosis in rat mesenteric microvessels" *Thrombosis Research* 90 (1998) 199-206) suggests that "the interactions between thrombin and the inhibitors in vivo are different from those in vitro".

One of the aims of the inventions is to provide safe and suitable antidotes to heparin and to the pentasaccharide.

One of the aims of the inventions is to provide suitable antidotes to heparin and to the pentasaccharide, able to neutralize heparin and pentasaccharide, easy to use and devoid of side effects.

This is achieved through the use of appropriate mutated antithrombins.

More precisely, the present invention relates to the use of a mutated antithrombin having substantially no activity, in particular no anticoagulant activity, possibly in association with an anticoagulant, for the preparation of a drug intended for the prevention or treatment of pathologies linked to or associated with coagulation disorders.

The term <<mutated antithrombin>> designates a human antithrombin comprising at least a substitution, insertion and/or deletion of one or more amino acids within its amino acid sequence.

The said mutated antithrombins can be prepared according to the method described in the experimental part I/.

The human antithrombin sequence is described in Olds R. J., Lane D. A., Chowdhury V., De Stefano V., Leone G. and Thein S. L. "Complete nucleotide sequence of the antithrombin gene: evidence for homologous recombination causing thrombophilia>> *Biochemistry*. 32 (16), 4216-4224 (1993).

The human antithrombin sequence of the invention is an Homo sapiens serpin peptidase inhibitor, Glade C (antithrombin), member 1 (SERPINC1), mRNA. Accession NM 000488, Version NM 000488.2, GI:50541941.

There are many references which describe said DNA sequence (with signal peptide) but they are not absolutely identical because of the many natural polymorphisms of antithrombin which generally do not change the properties of the antithrombin.

The human aminosequence of antithrombin presents two forms: a "short form" (SEQ ID NO: 2) which does not comprise a signal peptide and a "long form" (SEQ ID NO: 26) which includes a signal peptide.

The signal peptide comprises 32 amino acids and is necessary for antithrombin secretion. It is removed during antithrombin processing and the plasma antithrombin circulates as the <<short form>>.

Accordingly, in the present invention, the mutated antithrombins amino acid sequences, represented by SEQ ID NO: 2, 4, 6, 8, 10, 12, 14, 16, 18, 20, 22 and 24, do not comprise the signal peptide and the mutated antithrombins amino acid sequences, represented, by SEQ ID NO: 26, 28, 30, 32, 34, 36, 38, 40, 42, 44, 46 and 48, include the signal peptide.

The mutated antithrombin of the invention can be used in association or not with an anticoagulant.

The term <<mutated antithrombin>> as used herein, designates:

mutated antithrombins which are different from mutants of antithrombin known in the art in that said mutated antithrombins of the invention have no anticoagulant activity, and able to compete in vivo with plasma antithrombin for glycosaminoglycans binding, and furthermore, when mutated antithrombins of the invention are used with anticoagulant, mutated antithrombins have, in addition to the above mentioned properties, the property to compete in vivo with plasma antithrombin with respect to the binding to the anticoagulant.

It has unexpectedly been found that said mutated antithrombins of the invention are able to compete in vivo with plasma antithrombin and can be used to prevent or treat excessive fluidity of blood.

Moreover, it has unexpectedly been found that the said mutated antithrombins are able to compete with plasma antithrombin with respect to the binding to the anticoagulant and that the therapeutic administration of mutated antithrombins, in association with anticoagulants, prevents the undesired complications, and in particular hemorrhages, resulting from side effects of said anticoagulant.

The expression <<mutated antithrombin having substantially no activity>> designates a mutated antithrombin which has lost its capacity to inhibit coagulation.

An example of a test to determine the absence of anticoagulant activity is described in the experimental part II/a) of the present application.

The expression <<anticoagulant>> designates a substance that prevents coagulation and can be used in vivo as a medication for thrombotic disorders.

The expression <<pathologies linked to or associated with coagulation disorders>> as used herein designates a coagulation excess or defect, caused by abnormalities in the composition of the blood, the quality of the vessel wall and/or the nature of the blood flow.

More preferably, the present invention relates to the use of a mutated antithrombin at a concentration from about 0.1 to about 10 fold the concentration of the plasmatic antithrombin, particularly from about 1 to about 5 fold the concentration of the plasma antithrombin.

The concentration of the plasma antithrombin is from about 150 µg/ml to about 350 µg/ml, particularly about 300 µg/ml.

In an advantageous embodiment, the present invention relates to the use of a mutated antithrombin, in association with an anticoagulant, for the preparation of a drug intended for the treatment or prevention of hemorrhagic disorders and related pathologies, resulting from side effects of said anticoagulant.

In many clinical situations, heparin and in particular the pentasaccharide of heparin, is effective for prevention and treatment of thromboembolic events, but would require dose adjustment.

If the dosage of administrated heparin is not appropriate, heparin can cause serious adverse effects, in particular hemorrhage.

The use of a mutated antithrombin such as described above, allows to neutralize in particular heparin or the pentasaccharide and to prevent and/or treat hemorrhage.

The expression <<hemorrhagic disorders and related pathologies resulting from side effects of said anticoagulant>> designates bleeding complications. Bleeding side effects ranged in severity from local hematomas to major hemorrhagic events including death.

The present invention relates to the use of the above mentioned mutated antithrombin, wherein said mutated antithrombin has the ability to bind to the anticoagulant and to shift, in particular in vivo, the binding between plasma antithrombin and said anticoagulant.

The expression <<mutated antithrombin has the ability to bind to the anticoagulant>> designates a mutated antithrombin which binding affinity for the anticoagulant is similar or higher than that of plasma antithrombin for the anticoagulant.

A test for the determination of the binding between the mutated antithrombin and the anticoagulant is for instance the measure of the intrinsic fluorescence of the mutated antithrombin in the absence or in the presence of increasing concentration of anticoagulant (Meagher, Beechem, Olson and Gettins J B C 1998, 23283-232).

The term <<to shift in vivo the binding>> corresponds to a competition between plasma antithrombin and mutated antithrombin for the anticoagulant binding.

A test for the determination of the shift of the binding by mutated antithrombins is for instance the measure of the plasma antithrombin anti factor Xa inhibitory activity in a plasma containing the anticoagulant.

This test is described in experimental part (II/b for in vitro experiments and III/2 for in vivo experiments).

It is important to investigate, in vivo in an experimental model, the effect of the mutated antithrombin on plasma antithrombin-anticoagulant complex because in vitro tests are not sufficient to predict the in vivo effect of the mutated antithrombins of the invention.

The term <<plasma antithrombin>> corresponds to an endogenous glycoprotein produced by the liver. The alpha-antithrombin is the dominant form in blood plasma. The physiological target proteases of plasma antithrombin are those of the intrinsic coagulation system, namely the active forms of factor VII, (VIIa), Xa, IXa, VIIa, XIa, XIIa and the thrombin. Proteases inactivation results as a consequence of the trapping the protease in an equimolar covalent complex with plasma antithrombin in which the active site of the protease enzyme is inaccessible to its usual substrate. It is known that plasma antithrombin has a high affinity for heparin and that inhibition rates on thrombin and factor Xa can be accelerated up to 10,000 fold in the presence of heparin.

In an advantageous embodiment, the present invention relates to the use of the above-mentioned mutated antithrombin in association with a mutant of antithrombin, the amino acid sequence of which differs from that of said mutated antithrombin, wherein said mutated antithrombin has the ability to shift, in particular in vivo, the binding between plasma antithrombin and said anticoagulant and the ability to shift, in particular in vivo, the binding between said mutant of antithrombin and said anticoagulant.

The term <<mutant of antithrombin>> designates all the variants of antithrombin with increased anticoagulant activity and which are different from endogenous mutants of antithrombin.

The term <<amino acid sequence of which differs from that of said mutated antithrombin>> designates that there is at least one amino acid which is different, by its nature, or its presence or absence, when comparing the sequence of the mutated antithrombin of the invention and the sequence of the mutant of antithrombin.

The present invention relates to the use of the above-mentioned mutated antithrombin, wherein said mutated antithrombin has substantially lost factor Xa inhibitory activity and thrombin (IIa) inhibitory activity.

In particular, the present invention relates to the use of the above-mentioned mutated antithrombin, wherein said mutated antithrombin has substantially lost its inhibitory activity of serine proteases involved in the blood coagulation.

The expression <<factor Xa inhibitory activity>> designates the ability of antithrombin to interact with factor Xa and to irreversibly trap and inactivate this enzyme.

The expression <<thrombin inhibitory activity>> designates the ability of antithrombin to interact with thrombin and to irreversibly trap and inactivate this enzyme.

A test for the determination of the loss of the thrombin inhibitory activity is for instance an assay performed in vitro, in which thrombin is incubated with an excess of the tested mutated antithrombins in the presence or absence of pentasaccharide and in the presence of a given concentration of chromogenic substrate S2238. When mutated antithrombin exhibits thrombin inhibitory activity, absorbance at 405 nm resulting from S2238 cleavage increases according to a first-order exponential as a function of time. At the opposite, when mutated antithrombin loses its thrombin inhibitory activity or in the absence of inhibitor, absorbance at 405 nm follows a linear increase during the period of the assay.

A test for the determination of the loss of the FXa inhibitory activity is for instance an assay performed in vitro, in which thrombin is incubated with an excess of the tested mutated antithrombin in the presence or absence of pentasaccharide and in the presence of a given concentration of chromogenic substrate S2765. When mutated antithrombin exhibits FXa inhibitory activity, absorbance at 405 nm resulting from S2765 cleavage increases according to a first-order exponential as a function of time. At the opposite, when mutated antithrombin loses its FXa inhibitory activity or in the absence of inhibitor, absorbance at 405 nm follows a linear increase during the period of the assay.

According to an advantageous embodiment, the use of the mutated antithrombin of the present invention is characterized in that the value of the dissociation equilibrium constant (Kd) of the complex resulting from the binding of said mutated antithrombin with said anticoagulant, at a given ionic strength, in particular at physiological ionic strength, is similar or lower than the value of the Kd of the complex between plasma antithrombin and said anticoagulant.

The corresponding dissociation equilibrium constant (Kd) is measured according to the method described by monitoring the change in intrinsic protein fluorescence upon binding of heparin (Meagher, Beechem, Olson and Gettins J B C 1998, 23283-23289).

Heparin (or pentasaccharide) binding to antithrombin is assessed by titrating fixed level of antithrombin with heparin and monitoring the tryptophan fluorescence increase signaling heparin binding. Excitation and emission wavelengths 280 and 340 nm respectively are used and titration curves are fitted to the quadratic equilibrium binding equation to obtain the Kd (Olson S T, Björk I and Shore JD, 1993, *Methods enzymol.*, 222, 525-560).

Similarly, the dissociation equilibrium constant (Kd) of the complex, resulting from the binding of plasma antithrombin with said anticoagulant, is measured using the same method, with purified plasma antithrombin.

The expression <<a given ionic strength, in particular at physiological ionic strength>> designates an ionic strength corresponding to 150 mM NaCl (according to the Vidal dictionary, injectable sodium chloride solution should be at 0.9%, corresponding to 154 mM).

The expression <<is similar or lower than>> designates a Kd which is between 5 fold higher to 500 fold lower, more particularly 2 to 50 fold lower to the Kd determined for plasma antithrombin, in our experimental conditions.

The mutated antithrombin of the invention can be active even if the Kd is 5 fold higher than that of the plasma antithrombin provided that the corresponding doses required to shift the binding between plasma antithrombin and said anticoagulant are therapeutically compatible.

According to an advantageous embodiment, the use of the mutated antithrombin of the present invention is characterized in that the value of the Kd of the complex resulting from the binding of said mutated antithrombin with said anticoagulant, at a given ionic strength, in particular at physiological ionic strength, is similar or lower than the value of the Kd of the complex between said mutant of antithrombin and said anticoagulant.

The Kd value of the complex between mutant of antithrombin and said anticoagulant is estimated according to the same procedure above-mentioned.

According to an advantageous embodiment, said anticoagulant is chosen among heparins, heparins derivatives, in particular unfractioned heparins, low molecular weight heparins, the anticoagulant pentasaccharide (Fondaparinux), (Org31540/SR90107, Arixtra®) and its derivatives (Idraparinux: SANORG 34006), and heparinoids (Danaparoid sodium ORG 10172).

Other examples of anticoagulants which can be used are pentasaccharide with anti-Xa activity, pentasaccharide with anti-Xa activity and anti-IIa activity (Chritian Noti and Peter Seeberger, *Chemistry and biology.* 2005; 12:731-756) (Synthetic analogues of the Antithrombin III-Binding Pentasaccharide Sequence of heparin" Ronald G. M. van Amsterdam; Gerard M. T. Vorgel; Arie Visser; Wim J. Kop; Marc T. Buiting; Dirk G. Meuleman. *Atheroscler Thromb Vasc Biol.* 1995; 15:495-503).

Among pentasaccharide derivatives, there can be mentioned compounds No 33-51-78-81-84 and 93 described in Noti et al. 2005 and compounds 32543 and 32271 described in van Amsterdam et al. 1995 (see references above).

According to an advantageous embodiment, the pathologies linked to or associated with coagulation disorders are among arterial or venous thrombotic disorders such as pulmonary embolism, deep vein thrombosis, myocardial infraction, unstable angina, stroke, disseminated intravascular coagulation and among hemorrhagic disorders such as FVIII deficiency (hemophilia A), FIX deficiency (hemophilia B), FVII deficiency, FX deficiency, FXI deficiency, FII deficiency, vWF deficiency, acquired antibodies against these coagulation factors, fibrinolysis abnormalities, platelets abnormalities, disseminated intravascular coagulation and any pathology associated with a combination of these deficiencies or abnormalities.

When used with an anticoagulant, the mutated antithrombin of the invention can be used for the preparation of a drug intended for the prevention or treatment of thrombotic disorders such as pulmonary embolism, deep vein thrombosis, myocardial infraction, unstable angina, stroke, disseminated intravascular coagulation.

In an advantageous embodiment, the present invention relates to the use of the above defined mutated antithrombin, wherein said mutated antithrombin comprises at least one mutation within the region from the amino acid at position 380 to the amino acid at position 400, particularly within the region from the amino acid at position 380 to the amino acid at position 397, particularly within the region from the amino acid at position 390 to the amino acid at position 394, in particular at position 393, the amino acid numbering referring to the antithrombin amino acid sequence represented by SEQ ID NO: 2, said mutation being a substitution, insertion or deletion.

The region from the amino acid at position 380 to the amino acid at position 400 is generally named "reactive center loop" (RCL). The residues in the RCL are numbered according to their positions relative to the scissile P1-P1' bond (non-primed numbers towards the N-terminus and primed numbers towards the C-terminus of the serpin). In particular, the region stretching from P14 to P4' (residues from 380 to 397) is complementary to the active site of its target protease. In particular, residues from P4 to P1' (residues from 390 to 394) directly interact within protease catalytic groove. In particular, residue P1 (393) is crucial for protease inhibition.

The mutated antithrombins of the invention can comprise others mutations, outside of the region from the amino acid at position 380 to the amino acid at position 400, provided there is no change in the above-mentioned properties of the mutated antithrombins.

In an advantageous embodiment, the present invention relates to the use of the mutated antithrombin of the invention, wherein said mutated antithrombin further comprises at least one mutation at the glycosylation sites at the amino acid at position 96, 135, 155 or 192, in particular at position 135.

Glycosylation sites are necessary for antithrombin secretion when antithrombin is expressed in eukaryotic cells. However, removing one site does not impair antithrombin secretion while increases heparin binding. Indeed, glycosylation chains are involved in antithrombin-heparin binding.

In an advantageous embodiment, the present invention relates to the use such as defined above, of a mutated antithrombin, wherein said mutated antithrombin is an amino acid sequence selected from the group consisting of:

SEQ ID NO:4, said amino acid sequence comprising, in the sequence of antithrombin represented by SEQ ID NO:2, the substitution of the amino acid at position 393, by an Histidine (His), or SEQ ID NO:6, said amino acid sequence comprising, in the sequence of antithrombin represented by SEQ ID NO:2, the insertion of a Proline (Pro) between the amino acid at position 393 and the amino acid at position 394, or SEQ ID NO:8, said amino acid sequence comprising, in the sequence of antithrombin represented by SEQ ID NO:2, the deletion of the amino acid at position 393, or SEQ ID NO:10, said amino acid sequence comprising, in the sequence of antithrombin represented by SEQ ID NO:2, the deletion of the amino acid at position 394.

When there is one mutation, the mutated antithrombins above-mentioned are called single mutants.

In an advantageous embodiment, the present invention relates to the use such as defined above, of a mutated antithrombin, wherein said mutated antithrombin is an amino acid sequence selected from the group consisting of:

SEQ ID NO:14, said amino acid sequence comprising, in the sequence of antithrombin represented by SEQ ID NO:2, the substitution of the amino acid at position 393, by an Histidine (His), and the substitution of the amino acid at position 135, by a Glutamine (Gln), or SEQ ID NO:16, said amino acid sequence comprising, in the sequence of antithrombin represented by SEQ ID NO:2, the insertion of a Proline (Pro) between the amino acid at position 393 and the amino acid at position 394, and the substitution of the amino acid at position 135, by a Glutamine (Gln), or SEQ ID NO:18, said amino acid sequence comprising, in the sequence of antithrombin represented by SEQ ID NO:2, the deletion of the amino acid at position 393 and at position 394, or SEQ ID NO:20, said amino acid sequence comprising, in the sequence of antithrombin represented by SEQ ID NO:2, the deletion of the amino acid at position 393 and the substitution of the amino acid at position 135, by a Glutamine (Gln), or SEQ ID NO:22, said amino acid sequence comprising, in the sequence of antithrombin represented by SEQ ID NO:2, the deletion of the amino acid at position 394 and the substitution of the amino acid at position 135, by a Glutamine (Gln), or SEQ ID NO:24, said amino acid sequence comprising, in the sequence of antithrombin represented by SEQ ID NO:2, the deletion of the amino acid at position 393 and at position 394, and the substitution of the amino acid at position 135, by a Glutamine (Gln).

When there are two or three mutations, the mutated antithrombins above-mentioned are called double and triple mutants respectively.

In an advantageous embodiment, the present invention relates to the use of the above-mentioned mutated antithrombin, wherein said mutated antithrombin comprises at least one mutation within the region from the amino acid at position 412 to the amino acid at position 432, particularly within the region from the amino acid at position 412 to the amino acid at position 429, particularly within the region from the amino acid at position 422 to the amino acid at position 426, in particular at position 425, the amino acid numbering referring to the antithrombin amino acid sequence comprising the signal peptide, represented by SEQ ID NO: 26, said mutation being a substitution, insertion or deletion.

The mutated antithrombins of the invention can comprise others mutations, outside of the region from the amino acid at position 412 to the amino acid at position 432, provided there is no change in the above-mentioned properties of the mutated antithrombins.

In an advantageous embodiment, the present invention relates to the use of the above-mentioned mutated antithrombin, wherein said mutated antithrombin further comprises at least one mutation at the glycosylation sites at the amino acid at position 128, 167, 187 or 224, in particular at position 167.

In an advantageous embodiment, the present invention relates to the use of the above-mentioned mutated antithrombin, wherein said mutated antithrombin is an amino acid sequence selected from the group consisting of:

SEQ ID NO:28, said amino acid sequence comprising, in the sequence of antithrombin represented by SEQ ID NO:26, the substitution of the amino acid at position 425, by an Histidine (His), or SEQ ID NO:30, said amino acid sequence comprising, in the sequence of antithrombin represented by SEQ ID NO:26, the insertion of a Proline (Pro) between the amino acid at position 425 and the amino acid at position 426, or SEQ ID NO:32, said amino acid sequence comprising, in the sequence of antithrombin represented by SEQ ID NO:26, the deletion of the amino acid at position 425, or SEQ ID NO:34, said amino acid sequence comprising, in the sequence of antithrombin represented by SEQ ID NO:26, the deletion of the amino acid at position 426.

In an advantageous embodiment, the present invention relates to the use of the above-mentioned mutated antithrombin, wherein said mutated antithrombin is an amino acid sequence selected from the group consisting of:

SEQ ID NO:38, said amino acid sequence comprising in the sequence of antithrombin represented by SEQ ID NO:26, the substitution of the amino acid at position 425, by an Histidine (His), and the substitution of the amino acid at position 167, by a Glutamine (Gln), or SEQ ID NO:40, said amino acid sequence comprising, in the sequence of antithrombin represented by SEQ ID NO:26, the insertion of a Proline (Pro) between the amino acid at position 425 and the amino acid at position 426, and the substitution of the amino acid at position 167, by a Glutamine (Gln), or SEQ ID NO:42, said amino acid sequence comprising, in the sequence of antithrombin represented by SEQ ID NO:26, the deletion of the amino acid at position 425 and at position 426, or SEQ ID NO:44, said amino acid sequence comprising, in the sequence of antithrombin represented by SEQ ID NO:26, the deletion of the amino acid at position 425 and the substitution of the amino acid at position 167, by a Glutamine (Gln), or SEQ ID NO:46, said amino acid sequence comprising, in the sequence of antithrombin represented by SEQ ID NO:26, the deletion of the amino acid at position 426 and the substitution of the amino acid at position 167, by a Glutamine (Gln), or SEQ ID NO:48, said amino acid sequence comprising, in the sequence of antithrombin represented by SEQ ID NO:26, the deletion of the amino acid at position 425 and at position 426 and the substitution of the amino acid at position 167, by a Glutamine (Gln).

The present invention also relates to a product comprising at least one mutated antithrombin having substantially no activity, in particular no anticoagulant activity, and at least one compound, in particular anticoagulant, as a combination product for a separate or sequential use in the prevention or treatment of hemorrhagic disorders and related pathologies resulting from side effects of said anticoagulant.

The expression <<for a separate or sequential use>> designates the use of the mutated antithrombin between 5 minutes to 7 days after the last said anticoagulant administration, in particular 5 minutes to 72 hours.

The present invention relates to the above-mentioned product, wherein said mutated antithrombin has the ability to bind to the anticoagulant and to shift, in particular in vivo, the binding between plasma antithrombin and said anticoagulant.

The present invention relates to the above-mentioned product, wherein said mutated antithrombin has the ability to shift, in particular in vivo, the binding between plasma antithrombin and said anticoagulant and the ability to shift, in particular in vivo, the binding between said mutant of antithrombin and said anticoagulant.

The present invention relates to the above-mentioned product, wherein said mutated antithrombin has substantially lost factor Xa inhibitory activity and thrombin inhibitory activity.

According to an advantageous embodiment, the product according to the present invention is characterized in that the value of the dissociation equilibrium constant (Kd) of the complex resulting from the binding of said mutated antithrombin with said anticoagulant, at a given ionic strength, in particular at physiological ionic strength, is similar or lower than the value of the Kd of the complex between plasma antithrombin and said anticoagulant.

According to an advantageous embodiment, the product according to the present invention is characterized in that the value of the Kd of the complex resulting from the binding of said mutated antithrombin with said anticoagulant, at a given ionic strength, in particular at physiological ionic strength, is similar or lower than the value of the Kd of the complex between said mutant of antithrombin and said anticoagulant.

According to an advantageous embodiment, said anticoagulant is chosen among heparins, heparins derivatives, in particular unfractioned heparins, low molecular weight heparins, the anticoagulant pentasaccharide, (Fondaparinux), and its derivatives (Idraparinux: SANORG 34006), and heparinoids (Danaparoid sodium ORG 10172).

According to an advantageous embodiment, said coagulation disorders are among arterial or venous thrombotic disorders such as pulmonary embolism, deep vein thrombosis, myocardial infraction, unstable angina, stroke, disseminated intravascular coagulation and among hemorrhagic disorders such as FVIII deficiency (hemophilia A), FIX deficiency (hemophilia B), FVII deficiency, FX deficiency, FXI deficiency, FII deficiency, vWF deficiency, acquired antibodies against these coagulation factors, fibrinolysis abnormalities, platelets abnormalities, disseminated intravascular coagulation and any pathology associated with a combination of these deficiencies or abnormalities.

In an advantageous embodiment, the present invention relates to the product such as defined above, wherein said mutated antithrombin comprises at least one mutation within the region from the amino acid at position 380 to the amino acid at position 400, particularly within the region from the amino acid at position 380 to the amino acid at position 397, particularly at least one mutation within the region from the amino acid at position 390 to the amino acid at position 394, in particular at position 393, the amino acid numbering referring to the antithrombin III amino acid sequence represented by SEQ ID NO: 2, said mutation being a substitution, insertion or deletion.

In an advantageous embodiment, the present invention relates to the product such as defined above, wherein said mutated antithrombin further comprises at least one mutation at the glycosylation sites at the amino acid at position 96, 135, 155 or 192, in particular at position 135.

In an advantageous embodiment, the present invention relates to the product such as defined above, wherein said mutated antithrombin is an amino acid sequence selected from the group consisting of:
SEQ ID NO:4,
SEQ ID NO:6,
SEQ ID NO:8, or
SEQ ID NO:10.

In an advantageous embodiment, the present invention relates to the product such as defined above, wherein said mutated antithrombin is an amino acid sequence selected from the group consisting of:
SEQ ID NO:14,
SEQ ID NO:16,
SEQ ID NO:18,
SEQ ID NO:20,
SEQ ID NO:22, or
SEQ ID NO:24.

In another advantageous embodiment, the present invention relates to the product such as defined above, wherein said mutated antithrombin comprises at least one mutation within the region from the amino acid at position 412 to the amino acid at position 432, particularly within the region from the amino acid at position 412 to the amino acid at position 429, particularly at least one mutation within the region from the amino acid at position 422 to the amino acid at position 426, in particular at position 425, the amino acid numbering referring to the antithrombin amino acid sequence comprising the signal peptide, represented by SEQ ID NO: 26, said mutation being a substitution, insertion or deletion.

In an advantageous embodiment, the present invention relates to the product such as defined above, wherein said mutated antithrombin further comprises at least one mutation at the glycosylation sites at the amino acid at position 128, 167, 187 or 224, in particular at position 167.

In an advantageous embodiment, the present invention relates to the product such as defined above, wherein said mutated antithrombin is chosen from the group consisting of:

SEQ ID NO:28,
SEQ ID NO:30,
SEQ ID NO:32 or
SEQ ID NO:34.

In an advantageous embodiment, the present invention relates to the product such as defined above, wherein said mutated antithrombin is chosen from the group consisting of:
SEQ ID NO:38,
SEQ ID NO:40,
SEQ ID NO:42,
SEQ ID NO:44,
SEQ ID NO:46, or
SEQ ID NO:48.

The present invention also relates to the use of a mutated antithrombin having substantially no activity, in particular no anticoagulant activity, without anticoagulant, for the preparation of a drug intended for the prevention or treatment of pathologies linked to or associated with coagulation disorders.

When used without association with an anticoagulant, the mutated antithrombin of the invention can be used for the preparation of a drug intended for the prevention or treatment of hemorrhagic disorders such as FVIII deficiency (hemophilia A), FIX deficiency (hemophilia B), FVII deficiency, FX deficiency, FXI deficiency, FII deficiency, vWF deficiency, acquired antibodies against these coagulation factors, fibrinolysis abnormalities, platelets abnormalities, disseminated intravascular coagulation and any pathology associated with a combination of these deficiencies or abnormalities.

In an advantageous embodiment, the present invention relates to the use such as defined above, of a mutated antithrombin having substantially no activity, in particular no anticoagulant activity, without anticoagulant, for the preparation of a drug intended for the prevention or treatment of hemorrhagic disorders.

The present invention also relates to a mutated antithrombin, which contains at least an amino acid insertion between the amino acid at position 393 and the amino acid at position 394, in the sequence of antithrombin represented by SEQ ID NO:2, in particular an insertion of a Proline (Pro), and in particular mutated antithrombin represented by SEQ ID NO: 6.

The present invention also relates to a mutated antithrombin, which contains at least an amino acid insertion between the amino acid at position 425 and the amino acid at position 426, in the sequence of antithrombin represented by SEQ ID NO:26, in particular an insertion of a Proline (Pro), and in particular mutated antithrombin represented by SEQ ID NO: 30.

The present invention also relates to a mutated antithrombin, which contains at least an amino acid deletion of the amino acid at position 393, in the sequence of antithrombin represented by SEQ ID NO:2, in particular mutated antithrombin represented by SEQ ID NO: 8.

The present invention also relates to a mutated antithrombin, which contains at least an amino acid deletion of the amino acid at position 425, in the sequence of antithrombin represented by SEQ ID NO:26, in particular mutated antithrombin represented by SEQ ID NO: 32.

The present invention also relates to a mutated antithrombin, which contains at least an amino acid deletion of the amino acid at position 394, in the sequence of antithrombin represented by SEQ ID NO:2, in particular mutated antithrombin represented by SEQ ID NO: 10.

The present invention also relates to a mutated antithrombin, which contains at least an amino acid deletion of the amino acid at position 426, in the sequence of antithrombin represented by SEQ ID NO:26, in particular mutated antithrombin represented by SEQ ID NO: 34.

The present invention also relates to a mutated antithrombin, which contains at least two mutations:

- the first mutation being, in the sequence of antithrombin represented by SEQ ID NO:2, the substitution of the amino acid at position 393, by an Histidine (His), the second mutation being the substitution of the amino acid at position 135, by a Glutamine (Gln), said mutated antithrombin being in particular represented by SEQ ID NO: 14,
- the first mutation being, in the sequence of antithrombin represented by SEQ ID NO:2, the insertion of a Proline (Pro) between the amino acid at position 393 and the amino acid at position 394, the second mutation being the substitution of the amino acid at position 135, by a Glutamine (Gln), said mutated antithrombin being in particular represented by SEQ ID NO: 16, or
- the first mutation being, in the sequence of antithrombin represented by SEQ ID NO:2, the deletion of the amino acid at position 393, the second mutation being the deletion of the amino acid at position 394, said mutated antithrombin being in particular represented by SEQ ID NO: 18, or
- the first mutation being, in the sequence of antithrombin represented by SEQ ID NO:2, the deletion of the amino acid at position 393, the second mutation being the substitution of the amino acid at position 135, by a Glutamine (Gln), said mutated antithrombin being in particular represented by SEQ ID NO: 20, or
- the first mutation being, in the sequence of antithrombin represented by SEQ ID NO:2, the deletion of the amino acid at position 394, the second mutation being the substitution of the amino acid at position 135, by a Glutamine (Gln), said mutated antithrombin being in particular represented by SEQ ID NO: 22, or
- the first mutation being, in the sequence of antithrombin represented by SEQ ID NO:2, the deletion of the amino acid at position 393, the second mutation being the deletion of the amino acid at position 394, and the third mutation being substitution of the amino acid at position 135, by a Glutamine (Gln), said mutated antithrombin being in particular represented by SEQ ID NO: 24.

The present invention also relates to a mutated antithrombin, which contains at least two mutations:

- the first mutation being, in the sequence of antithrombin represented by SEQ ID NO:26, the substitution of the amino acid at position 425, by an Histidine (His), the second mutation being the substitution of the amino acid at position 167, by a Glutamine (Gln), said mutated antithrombin being in particular represented by SEQ ID NO: 38,
- the first mutation being, in the sequence of antithrombin represented by SEQ ID NO:26, the insertion of a Proline (Pro) between the amino acid at position 425 and the amino acid at position 426, the second mutation being the substitution of the amino acid at position 167, by a Glutamine (Gln), said mutated antithrombin being in particular represented by SEQ ID NO: 40, or
- the first mutation being, in the sequence of antithrombin represented by SEQ ID NO:26, the deletion of the amino acid at position 425, the second mutation being the deletion of the amino acid at position 426, said mutated antithrombin being in particular represented by SEQ ID NO: 42, or
- the first mutation being, in the sequence of antithrombin represented by SEQ ID NO:26, the deletion of the amino acid at position 425, the second mutation being the substitution of the amino acid at position 167, by a Glutamine (Gln), said mutated antithrombin being in particular represented by SEQ ID NO: 44, or the first mutation being, in the sequence of antithrombin represented by SEQ ID NO:26, the deletion of the amino acid at position 426, the second mutation being the substitution of the amino acid at position 167, by a Glutamine (Gln), said mutated antithrombin being in particular represented by SEQ ID NO: 46, or the first mutation being, in the sequence of antithrombin represented by SEQ ID NO:26, the deletion of the amino acid at position 425, the second mutation being the deletion of the amino acid at position 426, and the third mutation being substitution of the amino acid at position 167, by a Glutamine (Gln), said mutated antithrombin being in particular represented by SEQ ID NO: 48.

The present invention also relates to a nucleotide sequence encoding a mutated antithrombin as defined above, in particular nucleotide sequences chosen in the group consisting of SEQ ID NO: 5, 7, 9, 13, 15, 17, 19, 21, 23, 29, 31, 33, 37, 39, 41, 43, 47.

The present invention also relates to a pharmaceutical composition comprising as active ingredient a mutated antithrombin as defined above, in combination with a pharmaceutical acceptable vehicle, in particular a mutated antithrombin of SEQ ID NO: 6, 8, 10, 14, 16, 18, 21, 22, 24, 30, 32, 34, 38, 40, 42, 44, 46, 48.

The present invention also relates to a pharmaceutical composition, comprising as active ingredient a mutated antithrombin, of SEQ ID NO:4, 12, 28 or 36 in combination with a pharmaceutical acceptable vehicle.

FIGURES

FIG. 1: Preparation of Shuttle Vector Carrying Full Length Antithrombin cDNA.

2 µg of pENTR vector containing truncated AT cDNA (lane 1 and 2), pCMV6 vector containing full length AT cDNA (lane 3 and 4) or shuttle vector pENTR-AT (lane 5 and 6) are loaded on 1% agarose gel before (lane 1, 3, 5) or after (lane 2, 4, 6) complete digestion by both SacII and StuI. Molecular weight standard sizes are indicated on the left hand of the figure and expressed in base pair (bp). SacII/StuI digestion of pCMV6 vector containing full length AT cDNA releases a 1182 bp band corresponding to full length AT cDNA cloned into pENTR vector isolated from SacII/StuI digestion of pENTR vector containing truncated AT cDNA. After ligation of these two fragments the final product is effectively recircularized and shows the expected profile for pENTR-AT after SacII/StuI digestion.

Figure 2:
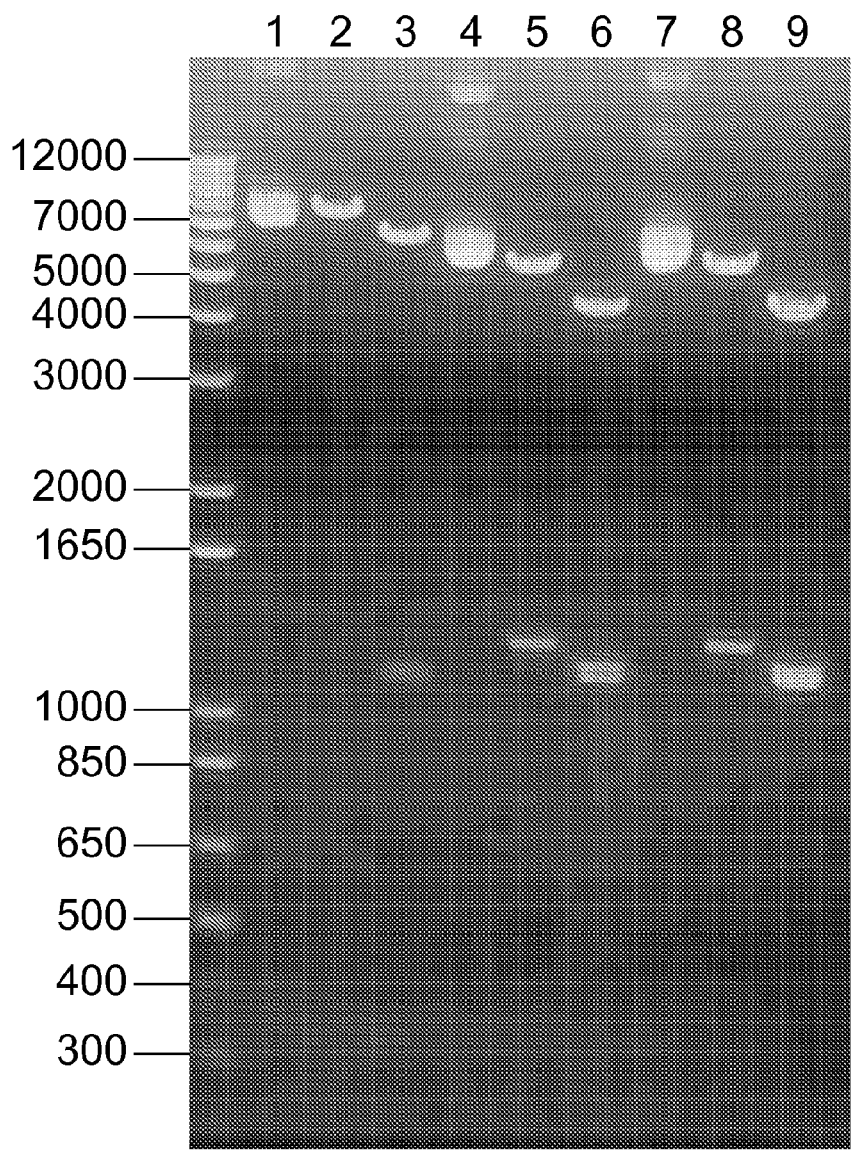

FIG. 2: Characterization of the AT Expression Vector.

2 µg of pCDNA 3.2 vector (lane 1, 2, 3), pCDNA 3.2 vector containing full length AT cDNA (lane 4, 5, 6) or pCDNA 3.2 vector containing full length AT-N135Q-Pro394 cDNA (lane 7, 8, 9) are loaded on 1% agarose gel before endonucleases treatment (lane 1, 4, 7), after cleavage by StuI (lane 2, 5, 8), or after complete cleavage by both SacII and StuI (lane 3, 6, 9). Molecular weight standard sizes are indicated on the right hand of the figure and expressed in base pair (bp). There is one SacII and one StuI cleavage site in pCDNA 3.2 vector at position 3189 and 4329 respectively. Therefore cleavage of pCDNA 3.2 by StuI only leads to linearization of the vector (7711 bp band) whereas cleavage of pCDNA 3.2 by both StuI and SacII cuts the vector in two fragments (6571 bp and 1140 bp). Substitution of 912-3174 fragment by AT cDNA fragment (1448 bp) into pCDNA 3.2 by recombination introduces one more SacII site at position 1070 and one more StuI site at position 2252 into pcDNA-AT. Then cleavage of pCDNA-AT by StuI gives two fragments (5634 bp and 1263 bp) and cleavage by both endonucleases gives 4 fragments (4452 bp, 1182 bp, 1140 and 123 bp). The same is true for -N135Q-Pro394 cDNA.

Figure 3:
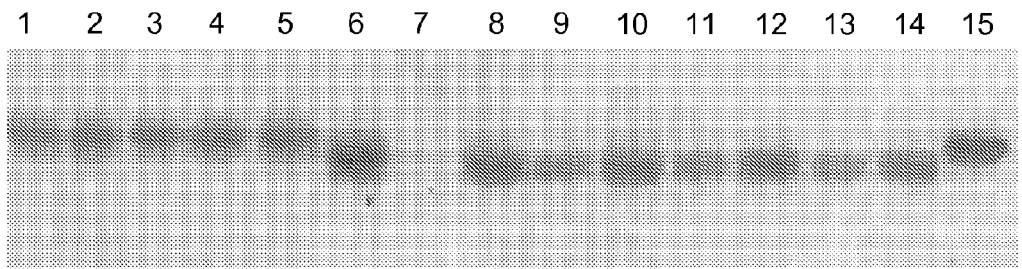

FIG. 3: Clone Screening for Secretion of Recombinant AT in Cell Culture Media.

For each clone isolated after transfection with pCDNA-AT (clone 1 to 5 in lane 1 to 5, respectively), pCDNA-AT-N135Q (clone 1 to 4 in lane 6 to 9, respectively), or with pCDNA-AT-N135Q-Pro394 (clone 1 to 5 in lane 10 to 14, respectively), 30 µl of conditioned media harvested after 24 hours contact with cells are analysed by western-blotting in denaturing condition for their ability to secrete full length recombinant antithrombin. For each clone a single band of variable intensity corresponding to recombinant antithrombin can be seen. Recombinant wild type antithrombin migrate at the same level than control antithrombin purified from plasma (lane 15, 150 ng/lane) and expression level is estimated around 2 mg/L according to band intensity measurement. For wt-AT, clone 4 is chosen for expansion into cell factory, since the level of expression seems to be slightly higher than the others. Mutant AT-N135Q (SEQ ID NO: 12) and AT-N135Q-Pro394 (SEQ ID NO: 16) migrate just below control antithrombin purified from plasma (lane 15) confirming the loss of a glycosylation site due to substitution N135Q. The stable expression clones selected for large scale protein production are clones 1 for both AT-N135Q (SEQ ID NO: 12) and AT-N135Q-Pro394 (SEQ ID NO: 16).

Figure 4:
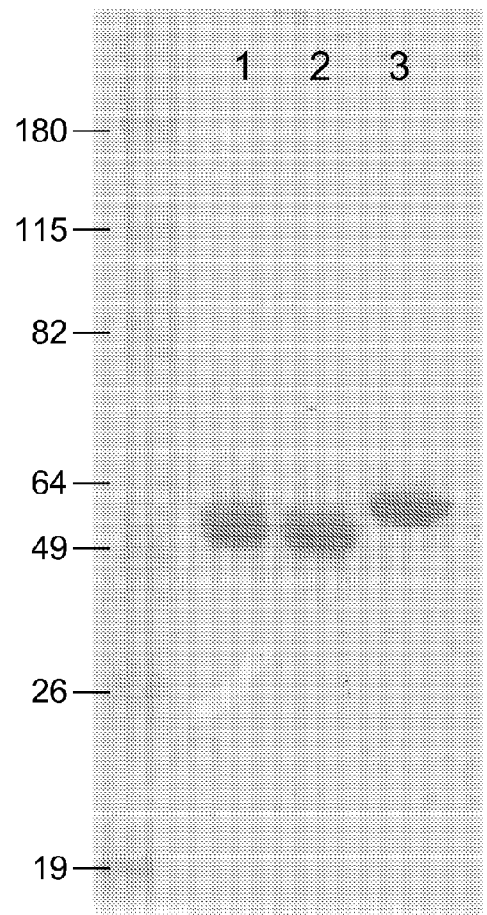

FIG. 4: Integrity and Purity of Recombinant Antithrombin.

To verify integrity and purity of recombinant antithrombin after heparin affinity purification and ion exchange concentration, 2 µg of AT-N135Q-R393H(SEQ ID NO: 14) (lane 1), AT-N135Q-Pro394 (SEQ ID NO: 16) (lane 2) or control plasma antithrombin (lane 3) are analyzed by SDS-PAGE followed by coomassie staining. As expected, the two mutated antithrombins migrate at molecular weight slightly lower than plasma antithrombin because of loss of a glycosylation site (substitution N135Q) and they show a single band pattern with band intensity corresponding to quantity loaded on the gel (based on absorbance estimation). Then recombinant antithrombin appears pure and can be tested for its anticoagulant properties and affinity for heparin derivatives. Molecular weight standard sizes are presented on the right hand of the figure and expressed in kiloDalton (KD)

Figure 5:
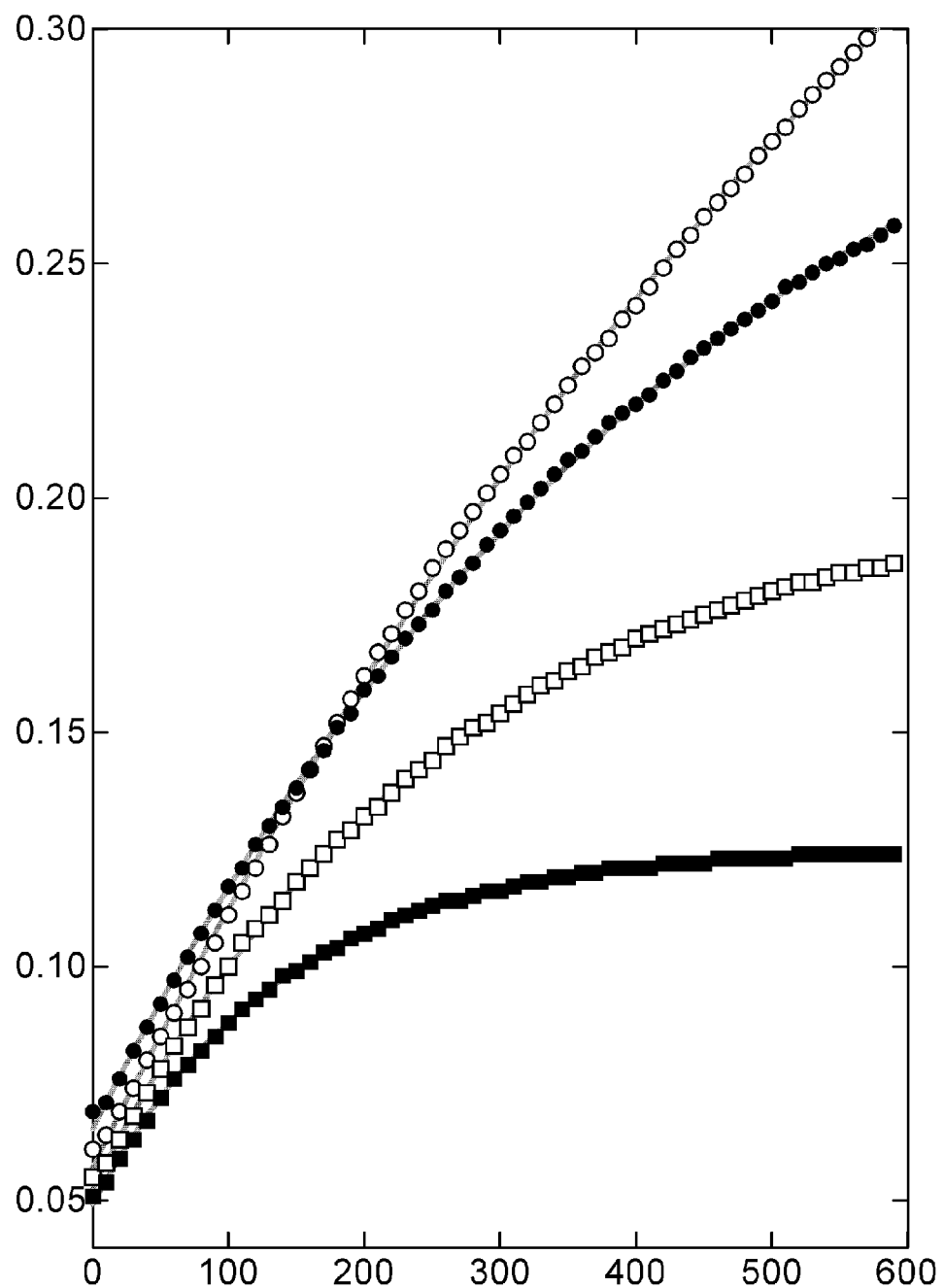
Figure 5:
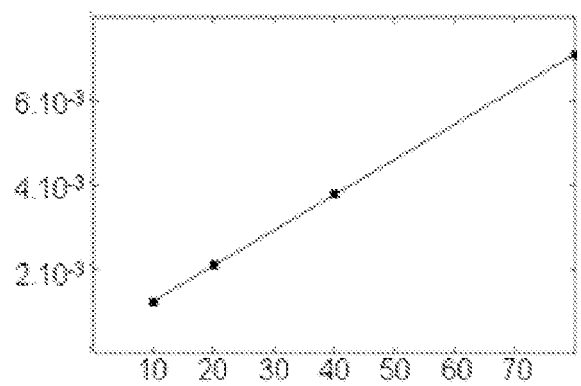

FIG. 5: Anti-Factor Xa Activity of Plasmatic or Mutated Antithrombins at Saturating Pentasaccharide Concentration.

FIG. 5 a: Plasma AT (black square (or black rectangle): 80 nM, hollow square: 40 nM, Black circle: 20 nM, hollow circle: 10 nM) is tested for its ability to inhibit chromogenic substrate S2765 (200 µM) hydrolysis by FXa (1 nM) in the presence of pentasaccharide (1 µM or 1.73 mg/L) in continuous assay. Time expressed in second is plotted in abscissa; absorbance at 405 nm is plotted in ordinate.

FIG. 5 b: FIG. 5 a substrate hydrolysis curves are fitted using equation 3 to determine the kinetic rate constant (k). This constant k is thus plotted as the function of AT concentration and fitted using equation 4 to determine inhibition rate constant kon. The plasma antithrombin concentration (nM) is plotted in abscissa; the kinetic rate constant (k) expressed in $s^{-1}$ is plotted in ordinate.

Figure 6:
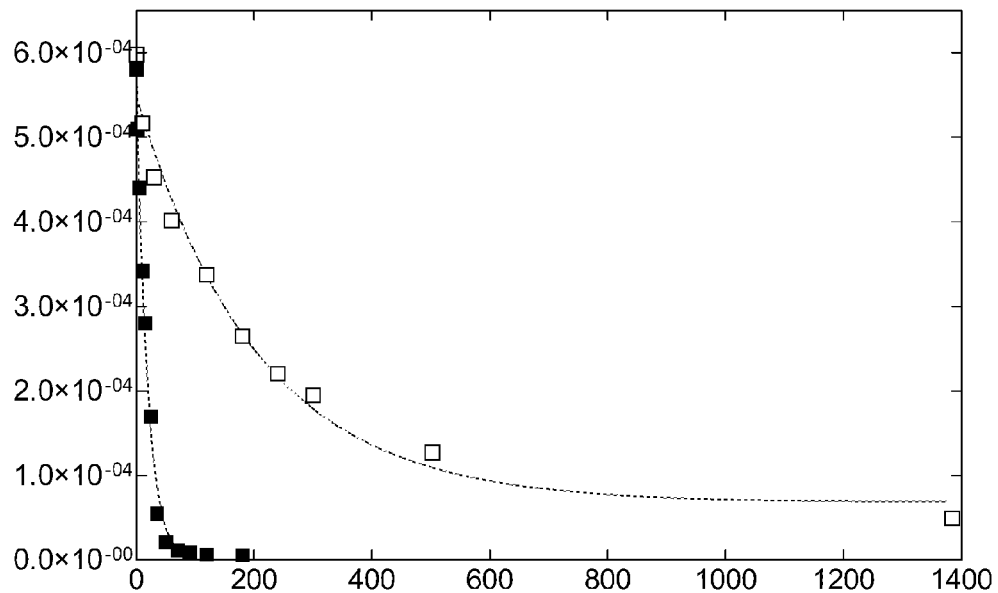

FIG. 6: Anti-Factor Xa Activity of Mutated Antithrombins in Discontinuous Assay

AT-N135Q-R393H (SEQ ID NO: 14) and AT-N135Q-Pro394 (SEQ ID NO: 16) are tested for their ability to inhibit FXa activity in discontinuous assay. In a first time AT-N135Q-R393H (SEQ ID NO: 14) (black square: 200 nM) or AT-N135Q-Pro394 (SEQ ID NO: 16) (hollow square: 2.5 µM) are incubated with FXa (20 nM) in the presence of pentasaccharide (10 µM or 17.3 mg/L) over a period of time from 0 to 120 min (for AT-N135Q-R393H, (SEQ ID NO: 14) or from 0 to 1400 min (for AT-N135Q-Pro394, SEQ ID NO: 16). In a second time FXa residual activity is measured by adding 190 µl of S2765 (200 µM) to 10 µl of previous mixture. Initial rate of substrate hydrolysis is then plotted as the function of incubation time with inhibitor and curves are fitted with equation 1 to determine kon (gray lines). Time expressed in minute is plotted in abscissa; substrate hydrolysis rate expressed in $OD/s^{-1}$ is plotted in ordinate.

Figure 7:
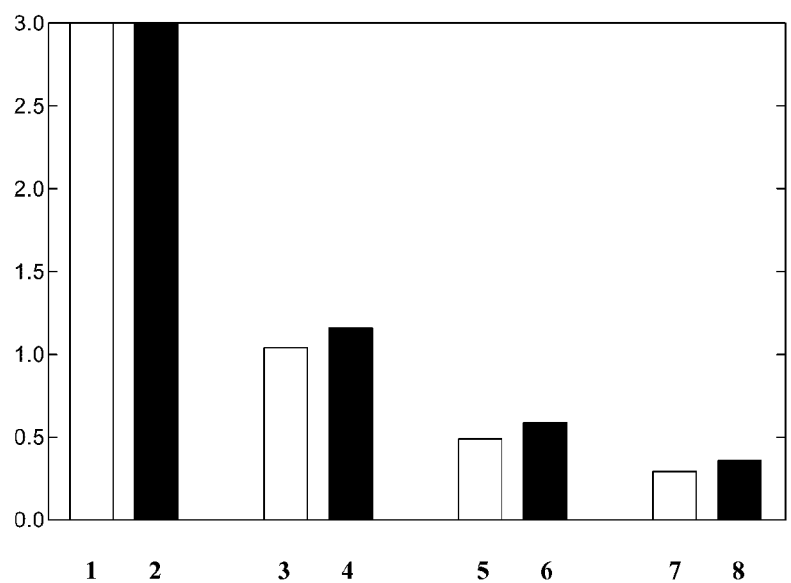

FIG. 7: AT can Compete with Plasma AT for Pentasaccharide Binding

AT-N135Q-R393H (SEQ ID NO: 14) and AT-N135Q-Pro394 (SEQ ID NO: 16) are tested in Rotachrom® heparin assay to establish residual pentasaccharide activity. Mutated antithrombins in a 1/1, 2/1 and 4/1 ratio compared to plasma antithrombin, are added to human plasma pool over-dosed with pentasaccharide (concentration of 3 µg/ml).

Bars 1, 3, 5 and 7 represent results with AT-N135Q-R393H (SEQ ID NO:14) and Bars 2, 4, 6 and 8 represent results with AT-N135Q-Pro394 (SEQ ID NO: 16). Bars 1 and 2 are control bars without mutated antithrombin. Bars 3 and 4 represent mutated antithrombin ratio 1/1 to plasma antithrombin. Bars 5 and 6 represent mutated antithrombin ratio 2/1 to plasma antithrombin. Bars 7 and 8 represent mutated antithrombin ratio 4/1 to plasma antithrombin.

Figure 8:
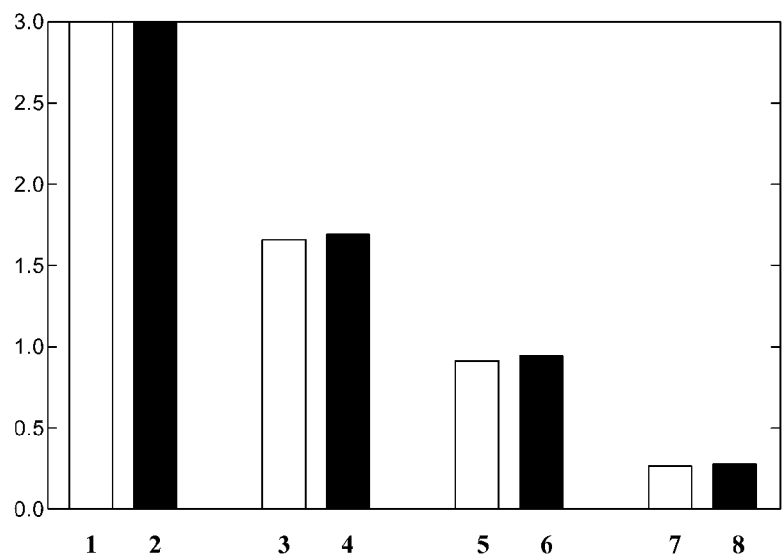

FIG. 8: AT can Compete with Plasma AT Forpentasaccharide Binding when Incubated on HUVEC Surface.

AT-N135Q-R393H(SEQ ID NO: 14) and AT-N135Q-Pro394 (SEQ ID NO: 16) are tested in Rotachrom® heparin assay to establish residual pentasaccharide activity. Mutated antithrombins in a 1/1, 2/1 and 4/1 ratio compared to plasma antithrombin, are added to human plasma pool over-dosed with pentasaccharide (concentration of 3 µg/ml) and incubated on HUVEC surface.

Bars 1, 3, 5 and 7 represent results with AT-N135Q-R393H (SEQ ID NO: 14) and Bars 2, 4, 6 and 8 represent results with AT-N135Q-Pro394 (SEQ ID NO: 16). Bars 1 and 2 are control bars without mutated antithrombin. Bars 3 and 4 represent mutated antithrombin ratio 1/1 to plasma antithrombin. Bars 5 and 6 represent mutated antithrombin ratio 2/1 to plasma antithrombin. Bars 7 and 8 represent mutated antithrombin ratio 4/1 to plasma antithrombin.

EXPERIMENTAL PART

In order to produce a mutated antithrombin having lost anticoagulant activity, in particular factor Xa and IIa inhibitory activity, and able to bind to heparin and to the pentasaccharide, different types of mutations have been contemplated and particularly, mutations within the reactive center loop (region from the amino acid 380 to amino acid 400), mutations within an exosite region remote from the loop accessible for proteinase interaction (Chuang Y J, Swanson R, Raja S M, Olson S T. Heparin enhances the specificity of antithrombin for thrombin and factor Xa independent of the reactive center loop sequence. Evidence for an exosite determinant of factor Xa specificity in heparin-activated antithrombin *J Biol Chem.* 2001; 276:14961-71) and mutations within a consensus sequence of glycosylation (amino acids 135 to 137 and 155 to 157) (Fan B, Crews B C, Turko W, Choay J, Zettlmeissl G, Gettins P. Heterogeneity of recombinant human antithrombin III expressed in baby hamster kidney cells. Effect of glycosylation differences on heparin binding and structure *J Biol Chem.* 1993; 268:17588-96).

Several mutations have been carried out to obtain mutated antithrombins, and in particular:
- deletion within the reactive loop of the antithrombin, in the region P4-P4' in order to eliminate antithrombin inhibitory activity toward any coagulant proteases such as FXa and FIIa,
- substitution of amino acids within the region P4-P4' (Ala 391-Asn 396) of the reactive loop, and in particular the substitution of the amino acid at position 393 (Arg) by an Histidine,
- insertion of a Proline between the amino acid at position 393 and the amino acid at position 394, and
- substitution of amino acids within the region of glycosylation of the antithrombin, and in particular the substitution of the amino acid at position 135 (Asp) by a Glutamine, in order to increase the affinity with heparin and pentasaccharide.

Material and Methods

I/Preparation of Mutated Antithrombins

Preparation of Shuttle Vector pENTR Carrying Full Length Antithrombin cDNA (pENTR-AT):

The antithrombin cDNA sequence initially cloned into pENTR vector (Invitrogen, HORF clone reference IOH14497) is found to be truncated and has to be replaced by the full length antithrombin sequence, cloned into pCMV6 (Origene, reference TC110831). The plasmid pCMV6 containing full length antithrombin cDNA is digested by both SacII and StuI endonucleases. The 1182 base pairs fragment is isolated on 1% agarose gel and purified using the QIAquick Gel Extraction Kit. This 1182 base pairs fragment, corresponding to the SacII-StuI fragment of antithrombin cDNA, is ligated into pENTR vector (2760 bp) also linearized by SacII and StuI and recover as described above. Result of this cassette exchange is verified by electrophoresis on 1% agarose gel (FIG. 1) and sequencing.

Mutagenesis on Antithrombin cDNA:

The resulting plasmid pENTR carrying cDNA encoding for wild type antithrombin (pENTR-ATwt) is used as a template for further mutagenesis by PCR using the QuickChange II Site-Directed Mutagenesis Kit according to the manufacturer recommendations (Stratagene). The wild type antithrombin has the same amino acid sequence as the plasma antithrombin but is produced under a recombinant form. Mutagenic primers (table 1) are used to introduce a codon for Glutamine in place of codon for Arginine 135 for production of plasmid pENTR-AT-N135Q. Single amino acid substitution of Arginine 393 by an Histidine (R393H), insertion of a Proline between Arginine 393 and Serine 394 (Pro394), or deletion of Arginine 393 (ΔR393), Serine 394 (ΔS394) or both Arginine 393 and Serine 394 (ΔR393S394) are introduced by PCR using the QuickChange II Site-Directed Mutagenesis Kit with pENTR-ATwt as template and mutagenic primers as described in table 1. The same couples of mutagenic primers are used in PCR reaction with pENTR-AT-N135Q as template to prepare plasmids carrying cDNA encoding for double-mutant and triple-mutant antithrombin N135Q-R393H(SEQ ID NO: 14), N135Q-Pro394 (SEQ ID NO: 16), N135Q-ΔR393 (SEQ ID NO: 20), N135Q-ΔS394 (SEQ ID NO: 22) and N135Q-ΔR393S394 (SEQ ID NO: 24) respectively. Then the integrity of each variant cassette that is to say cDNA encoding for the double-mutant or triple-mutant antithrombin above mentioned is established by DNA sequencing.

Cassette Exchange Between Shuttle Vector and Expression Vector:

All the cDNAs described above encoding for antithrombin, single antithrombin mutants or double antithrombin mutants are transferred from shuttle vector pENTR into eucaryote expression vector pCDNA 3.2 by recombination using Gateway LR Clonase II Enzyme Mix ("Gateway Technology" developed by Invitrogen). The final expression constructs are verified by electrophoresis on 1% agarose gel and sequencing again before transfection (FIG. 2).

Transfection of Eucaryote Cells and Protein Production:

Plasmid constructs resulting of previous recombination named pCDNA-ATwt, pCDNA-AT-N135Q, pCDNA-AT-R393H, pCDNA-AT-Pro394, pCDNA-AT-ΔR393, pCDNA-AT-ΔS394, pCDNA-AT-ΔR393S394, pCDNA-AT-N135Q-R393H, pCDNA-AT-N135Q-Pro394, pCDNA-AT-N135Q-ΔR393, pCDNA-AT-N135Q-ΔS394, and pCDNA-AT-N135Q-ΔR393S394, respectively are used for transfection of modified human embryonic kidney cells (HEK-293) or baby hamster kidney cells (BHK-21). Cells are grown in "Dulbeco's Modified Eagle's Medium/F-12" containing 2 mM L-Glutamine, 100 U/ml penicillin, 100 μg/ml Streptomycin and 5% foetal bovine serum (Invitrogen) and approximately $10^6$ cells are transfected with 20 μg of DNA by calcium-phosphate coprecipitation (Sambrook et al. Molecular cloning: A laboratory manual, $2^{nd}$ edition, page 16.33). The stable expression cell lines are selected by G418 (during clones selection, G418 concentration is 0.8 mg/ml in cell culture media and then decreased to 0.4 mg/ml to maintain selection pressure during clones amplification) and screened for antithrombin secretion by ELISA, using mouse monoclonal antibody anti antithrombin as capture antibody and Horse Radish Peroxydase conjugate sheep polyclonal antibody anti antithrombin as detecting antibody (BioAssay™ ELISA Kit (EUROMEDEX). The integrity of secreted antithrombin is established by western blotting using sheep monoclonal antibody anti antithrombin and Horse Radish Peroxydase conjugate donkey polyclonal antibody anti sheep (The Binding Site, UK) (FIG. 3). For each mutated antithrombin, a single stable expression clone is expanded into "cell factories nunclon" (Nunc) and large scale protein production is conducted with 300 μl/$cm^2$, (as recommended by manufacturer, the minimum volume suitable for a 6320 $cm^2$ culture area cell factory is 2 liters) of <<Dulbeco's Modified Eagle's Medium/F-12" containing 2 mM L-Glutamine, 100 U/ml penicillin, 100 μg/ml Streptomycin and 5 μg/ml Insulin/Transferrin/Selenium (Invitrogen). Conditioned media, harvested daily, are centrifuged for 15 min at 3000 g at 4° C., treated with 5 mM benzamidine, 5 mM EDTA and stored at −20° C.

Protein Purification:

Conditioned media are thawed, pooled, salt concentration adjusted to 0.4 M NaCl and then applied on an heparin immobilized column (Hitrap Heparin 5 ml or Heparin-sepharose CL6B 50 ml, GE Biological) equilibrated with 10 mM Tris, or with 20 mM phosphate buffer, 0.4 M NaCl and 0.1 mM EDTA, pH 7.4. The bound proteins are eluted in the same buffer with a gradient from 0.4 M to 2 M NaCl. The fractions eluted from 0.8 M NaCl and more contained only wild type antithrombin or mutated antithrombins with high heparin affinity. Mutated antithrombins carrying substitution of asparagine 135 by a glutamine (AT-N135Q (SEQ ID NO: 12), ATN135Q-R393H (SEQ ID NO: 14), AT-N135Q-Pro394 (SEQ ID NO: 16, AT-N135Q-ΔR393 (SEQ ID NO: 20), AT-N135Q-ΔS394 (SEQ ID NO: 22), AT-N135Q-ΔR393S394 (SEQ ID NO: 24)) are eluted from affinity column at higher ionic strength than wild type antithrombin, confirming that destruction of glycosylation site at position 135 increases affinity of antithrombin for heparin (about 90% of mutated antithrombin carrying substitution N135Q is eluted between 1 and 1.4 M NaCl compared to wild type antithrombin which 90% is eluted between 0.8 and 1.2 M NaCl). The collected fractions are pooled and the salt concentration is decreased either by over night dialysis against 10 mM Tris, or 20 mM phosphate, and 0.1 M NaCl, pH 7.4 at 4° C. or applied on an HiPrep 26/10 desalting column equilibrated with 10 mM Tris, or 20 mM phosphate, and 0.1 M NaCl, pH 7.4. The antithrombin is then concentrated by ion exchange chromatography using a "Resource Q" 1 ml column (GE, Biological) equilibrated with 10 mM Tris, or 20 mM phosphate, and 0.1 M NaCl, pH 7.4 and eluted in the same buffer with a NaCl gradient from 0.1 mM to 0.5 M or 20 mM to 0.5 M. The antithrombin concentration in each elution fraction is estimated by absorbance at 280 nM with an absorption coefficient $\epsilon$=0.65 $g^{-1}\cdot l\cdot cm^{-1}$ and the integrity of purified wild type antithrombin or mutated antithrombins is tested by western blotting using the same couple of antibodies as described before, and electrophoresis on 10% acrylamide/bisacrylamide gel in native and denaturing conditions followed by coomassie brilliant blue R-250 staining (FIG. 4). Then, the antithrombin preparation is aliquoted and stored at −80° C. before use for functional assay. The same procedure is used to purify plasma antithrombin (used as internal reference) from human plasma.

TABLE 1

| Sense | Mutation | Sequence | SEQ ID NO: |
|---|---|---|---|
| forward | N135Q | GCCGACTCTATCGAAAAGCCC AGAAATCCTCCAAGTTAGTG | 49 |
| reverse | N135Q | CACTAACTTGGAGGATTTCTG GGCTTTTCGATAGAGTCGGC | 50 |
| forward | R393H | GTTGTGATTGCTGGCCATTCGCTA AACCCCAAC | 51 |
| reverse | R393H | GTTGGGGTTTAGCGAATGGCCAGC AATCACAAC | 52 |
| forward | Pro394 | GTTGTGATTGCTGGCCGTCCATCGCTAAA CCCCAAC | 53 |
| reverse | Pro394 | GTTGGGGTTTAGCGATGGACGGCCAGCAA TCACAAC | 54 |
| forward | ΔR393-S394 | GCTGTTGTGATTGCTGGCCTAAACCCCAA CAGGGTG | 55 |
| reverse | ΔR393-S394 | CACCCTGTTGGGGTTTAGGCCAGCAATC ACAACAGC | 56 |

TABLE 1-continued

| Sense | Mutation | Sequence | SEQ ID NO: |
|---|---|---|---|
| forward | ΔR393 | CTGTTGTGATTGCTGGCTCGCTAAAC CCCAACAG | 57 |
| reverse | ΔR393 | CTGTTGGGGTTTAGCGAGCCAGCAAT CACAACAG | 58 |
| forward | ΔS394 | TGTGATTGCTGGCCGTCTAAACCC CAACAGGG | 59 |
| reverse | ΔS394 | CCCTGTTGGGGTTTAGACGGCCA GCAATCACA | 60 |

II/In Vitro Characterization of the Mutated Antithrombins

Characterization of the mutated antithrombins aims at
a) demonstrating that, in a purified system, the following mutated antithrombins: AT-R393H(SEQ ID NO: 4), AT-Pro394 (SEQ ID NO: 6), AT-ΔR393-S394 (SEQ ID NO: 18), AT-ΔR393 (SEQ ID NO: 8), AT-ΔS394 (SEQ ID NO: 10), AT-N135Q-R393H(SEQ ID NO: 14), AT-N135Q-Pro394 (SEQ ID NO: 16), AT-N135Q-ΔR393-S394 (SEQ ID NO: 24), AT-N135Q-ΔR393 (SEQ ID NO: 20) and AT-N135Q-ΔS394 (SEQ ID NO: 22) exhibit a negligible anti FXa and anti FIIa activity compared with that of wild type antithrombin (AT-wt) in the presence or absence of heparin or pentasaccharide, b) demonstrating that, in plasma, the following mutated antithrombins AT-R393H(SEQ ID NO: 4), AT-Pro394 (SEQ ID NO: 6), AT-ΔR393-5394 (SEQ ID NO: 18), AT-ΔR393 (SEQ ID NO: 8), AT-ΔS394 (SEQ ID NO: 10), AT-N135Q-R393H(SEQ ID NO: 14), AT-N135Q-Pro394 (SEQ ID NO: 16), AT-N135Q-ΔR393-S394 (SEQ ID NO: 24), AT-N135Q-ΔR393 (SEQ ID NO: 20), AT-N135Q-ΔS394 (SEQ ID NO: 22), can compete with plasma antithrombin for heparin or pentasaccharide binding and produce a significant decrease in anti factor Xa or anti factor IIa activity in plasma.

a) Anti Factor Xa Inhibitory Activity of the Mutated Antithrombins in a Purified System The kinetic assays for antithrombin inhibition of factor Xa (FXa, Kordia) are performed in 'kinetic' buffer (Hepes, 20 mM phosphate, pH 7.4, 0.15 M NaCl, 0.1% PEG 8000 and 1 mg/ml bovine serum albumin) in pseudo first order conditions. Briefly, factor Xa is incubated with an excess of tested antithrombins (corresponding to plasma antithrombin, or wild type antithrombin or mutated antithrombins and varying in each assay realized) in the presence or absence of pentasaccharide (Fondaparinux sodique, Arixtra®, GlaxoSmithKline) and the factor Xa residual activity is measured as a function of time. The pentasaccharide is added in excess in the reaction media so that every tested antithrombin is bound to the pentasaccharide. In the absence of pentasaccharide, polybrene is added in order to neutralize any sulfated glycosaminoglycan that may be present in the reaction media. The residual factor Xa activity is measured as the increase in absorbance at 405 nm resulting from cleavage of the chromogenic substrate (S2765 or S2222, Chromogenix) using a microplate reader (Dynatech MR 5000). The analysis of the data is performed using the GraphPad Prism version 3 software. Absorbance recording is continuous or discontinuous according to the expected inhibition rate constant (kon).

The inhibition rate constant (kon) is the second order rate constant given in $M^{-1}\cdot s^{-1}$ which define the velocity of stable complex formation between protease and antithrombin (higher is the kon value, faster will the complex be established).

When the expected kon is lower than $10^4$ $M^{-1}\cdot s^{-1}$ the discontinuous method is used. Factor Xa (0.2 to 1 μM, or 0.1 to 1 μM) is incubated with tested antithrombins (0.2 to 10 μM, or 1 to 10 μM) in the presence of pentasaccharide (10 to 100 μM) or polybrene (100 μg/ml) in a final volume of 10 μl for 10 seconds to 5 hours, or 10 seconds to 24 hours. At the end of this incubation period, 190 μl of kinetic buffer containing 200 μM substrate is added and absorbance at 405 nm is recorded.

The kinetic rate constant (k) is estimated by fitting the substrate hydrolysis initial rate curve to equation (1) using non-linear regression with v0 and v∞ being the substrate hydrolysis rate at time to or too respectively.

$$vt=(v0+v\infty)\cdot\exp(-k\cdot t) \quad (1)$$

The inhibition rate constant (kon) is calculated from the rate constant (k) using equation (2) where AT is the tested antithrombin concentration.

$$k=AT\cdot kon \quad (2)$$

When the expected kon is higher than $10^4$ $M^{-1}\cdot s^{-1}$' the continuous method is used. The tested antithrombin (0.01 to 1 μM, or 0.1 to 1 μM) is incubated with the substrate (200 μM) in the presence of pentasaccharide or polybrene in a final volume of 100 μL, or 190 μl, and the reaction is started by addition of 100 μL, or 10 μL, of factor Xa (2 nM or 10 nM). The rate constant (k) is obtained by fitting the substrate hydrolysis curve to equation (3) or (3') using non-linear regression analysis where A0 is the absorbance at t0, and vi and vs are respectively the initial and final rates of substrate hydrolysis in the absence of tested antithrombin.

$$A405=A0+vi\cdot(1-\exp(-k\cdot t))/k. \quad (3)$$

Equation (3') is also used, particularly in presence of plasma.

$$A405=A0+vs*t+(vi-vs)*(1-\exp(-k\cdot t))/k. \quad (3')$$

The inhibition rate constant (kon) is calculated from the kinetic constant (k) using equation (4) that takes into account the competitive effect of the substrate, with S being the initial substrate concentration, Km, the Michaelis constant for factor Xa-substrate interaction, AT the tested antithrombin concentration.

$$k=(kon/(1+S/Km))\cdot[AT] \quad (4)$$

Mutated antithrombins and wild type AT inhibitory activity are measured in the same conditions and compared with plasma AT inhibitory activity.

The results with or without pentasaccharide are:

wild type antithrombin and AT-N135Q (SEQ ID NO: 12) factor Xa inhibitory activity is similar to plasma antithrombin factor Xa inhibitory activity, factor Xa inhibitory activity of the following mutated antithrombins: AT-R393H(SEQ ID NO: 4), AT-Pro394 (SEQ ID NO: 6), AT-ΔR393-5394 (SEQ ID NO: 18), AT-ΔR393 (SEQ ID NO: 8), AT-ΔS394 (SEQ ID NO:

10), AT-N135Q-R393H(SEQ ID NO: 14), AT-N135Q-Pro394 (SEQ ID NO: 16), AT-N135Q-ΔR393-S394 (SEQ ID NO: 24), AT-N135Q-ΔR393 (SEQ ID NO: 20), AT-N135Q-ΔS394 (SEQ ID NO: 22), is negligible compared with wild type antithrombin factor Xa inhibitory activity.

For example, inhibition rate constant (kon) of plasma AT for factor Xa in the presence of saturating amount of pentasaccharide is estimated using continuous method (FIGS. 5 *a* and 5 *b*). A value of $2.52\times10^{5}$ $M^{-1}\cdot s^{1}$ is found which is comparable to published values (Olson S T, Björk I, Sheffer R, Craig P A, Shore J D, Choay J., *J Biol Chem.* 1992 Jun. 25; 267 (18): 12528-38, "Role of the antithrombin-binding pentasaccharide in heparin acceleration of antithrombin-proteinase reactions. Resolution of the antithrombin conformational change contribution to heparin rate enhancement.) Using this method AT-N135Q-R393H(SEQ ID NO:14) and AT-N135Q-Pro394 (SEQ ID NO: 16) are found to be slow factor Xa inhibitors, even in the presence of saturating pentasaccharide concentration. Thus, discontinuous method was performed to evaluate kon values for factor Xa inhibition by AT-N135Q-R393H(SEQ ID NO: 14) and AT-N135Q-Pro394 (SEQ ID NO: 16) in the presence of pentasaccharide (FIG. 6). AT-N135Q-R393H(SEQ ID NO: 14) anticoagulant activity is largely reduced whereas AT-N135Q-Pro394 (SEQ ID NO: 16) is almost devoid of anti-factor Xa activity. AT-N135Q-R393H (SEQ ID NO: 14) and AT-N135Q-Pro394 (SEQ ID NO: 16) kon values are estimated at 4415 $M^{-1}\cdot s^{-1}$ and 33 $M^{-1}\cdot s^{-1}$, respectively, which is 95 times and at least 7600 times lower than plasma AT.

b) Anti Factor Xa Inhibitory Activity of the Mutated Antithrombins in Human Plasma Anti factor Xa inhibitory activity of mutated antithrombins AT-R393H(SEQ ID NO: 4), AT-Pro394 (SEQ ID NO: 6), AT-ΔR393-5394 (SEQ ID NO: 18), AT-ΔR393 (SEQ ID NO: 8), AT-ΔS394 (SEQ ID NO: 10), AT-N135Q-R393H(SEQ ID NO: 14), AT-N135Q-Pro394 (SEQ ID NO: 16), AT-N135Q-ΔR393-S394 (SEQ ID NO: 24), AT-N135Q-ΔR393 (SEQ ID NO: 20), AT-N135Q-ΔS394 (SEQ ID NO: 22) is measured in pentasaccharide containing plasma. The plasma concentrations of pentasaccharides are defined on the basis on those measured in patients treated by the pentasaccharide under the conditions of a regular (curative) use of this molecule or in patients presenting an overdose of this drug, knowing that the optimal equilibrium concentration is 1.20-1.26 mg/L and the minimal equilibrium concentration is 0.46-0.62 mg/L during a curative pentasaccharide treatment (monograph, Arixtra®).

The anti factor Xa assay is performed using the Rotachrom® heparin method (Stago) adaptated for absorbance reading on a microplate reader (Dynatech MR 5000), or a STA analyser (Stago).

The procedure consists in mixing 30 μl of pentasaccharide containing plasma sample diluted four times in kinetic buffer, with 75 μl of chromogenic substrate (1 mM, provided in Rotachrom® heparin kit). After 4 min incubation, 75 μl of bovine factor Xa (24 nM, Rotachrom® heparin kit) is added to the plasma-substrate mixture. The factor Xa activity is measured a 405 nm absorbance increase, resulting from cleavage of the chromogenic substrate, using a microplate reader (Dynatech MR 5000). The rate constant (k), proportional to anti-factor Xa activity, is obtained by fitting the substrate hydrolysis curve to equation (3) or (3').

Firstly, the assay is calibrated in citrated (0.105 M) normal human plasma containing pentasaccharide concentrations ranging from 0 to 3 mg/L. A standard curve is generated and anti-factor Xa activity is expressed as mg of pentasaccharide per liter of plasma.

Secondly, to evaluate the anti factor Xa inhibitory activity of mutated antithrombins, the mutated antithrombin (0-0.6 g/L, preferably 0.15-0.6 g/L, final concentration, in kinetic buffer) is pre-incubated with an equal volume of pentasaccharide (0-3 mg/L, preferably 1-3 mg/L) containing plasma samples, during 30 min at 37° C.

Under these conditions, the mutated antithrombin concentration range from one to four times that of the plasma antithrombin level, which is compatible with a therapeutic use of antithrombin. Indeed, very high doses of mutated antithrombin, with a 5 fold increase in plasma antithrombin level, have already been used during clinical trials without side effects (Leitner J M, Firbas C, Mayr F B, Reiter R A, Steinlechner B, Jilma B., Recombinant human antithrombin inhibits thrombin formation and interleukin 6 release in human endotoxemia. Clin Pharmacol Ther. 2006 January; 79(1):23-34). Anti factor Xa inhibitory activity is then evaluated as previously described.

Finally to evaluate effect of mutated antithrombin on anti-factor Xa activity in conditions as close as possible to in vivo conditions, Rotachrom® heparin method is used to test anti-factor Xa activity in plasma pre-incubated with mutated antithrombin (0-0.6 g/L, preferably 0.15-0.6 g/L in kinetic buffer), during 30 min at 37° C. on human umbilical vein endothelial cells (HUVEC) in culture. Cells are inoculated at 20 000 cells/$cm^2$ in 96 well plate and grown to confluence for 24 hours in EGM-2 media (Clonetics, Cambrex). After two wash with phosphate buffer saline (Gibco, Invitrogen) cells are starved for 4 hours in EBM-2 media (Clonetics, Cambrex) and then washed again twice in phosphate buffer saline to prevent excess contamination with heparin present in the culture medium. HUVEC coated wells are then used for 30 min incubation of pentasaccharide containing plasma-mutated antithrombin mixture (125 μl/$cm^2$) before Rotachrom® heparin assay It is demonstrated that the mutated antithrombins compete with plasma antithrombin for pentasaccharide binding and are able to decrease significantly the plasma anti-Xa activity.

In the condition of the assay, addition of AT-R393H(SEQ ID NO: 4), AT-Pro394 (SEQ ID NO: 6), AT-ΔR393-S394 (SEQ ID NO: 18), AT-ΔR393 (SEQ ID NO: 8), AT-ΔS394 (SEQ ID NO: 10), AT-N135Q-R393H(SEQ ID NO: 14), AT-N135Q-Pro394 (SEQ ID NO: 16), AT-N135Q-ΔR393-S394 (SEQ ID NO: 24), AT-N135Q-ΔR393 (SEQ ID NO: 20), AT-N135Q-A5394 (SEQ ID NO: 22) produces a significant decrease in anti-Xa activity of a pentasaccharide contained in plasma sample.

To estimate whether mutated antithrombin can be used as reversal of pentasaccharide in case of over-dosing, AT-N135Q-R393H(SEQ ID NO: 14) and AT-N135Q-Pro394 (SEQ ID NO: 16) are tested in Rotachrom® heparin assay for their ability to restore factor Xa activity. Under conditions of treatment for prevention of venous thromboembolic events, optimal pentasaccharide concentration ranges between 1.2 and 1.26 μg/mL in plasma. To mimic an over-dosing, pentasaccharide is added to human plasma pool at concentration of 3 μg/ml. Rotachrom® heparin assay is then performed by incubation of plasma over-dosed with pentasaccharide in the presence of mutated antithrombin in a ratio 1/1, 2/1, and 4/1 compared to plasma antithrombin concentration (i.e. 0.15, 0.3, 0.6 g/l). In this ex vivo assay, anti-factor Xa activity is proportional to the amount of pentasaccharide bound natural antithrombin present in tested plasma, which amount is directly proportional to pentasaccharide concentration in plasma. Therefore, effect of mutated antithrombin is expressed as a virtual decrease in pentasaccharide concentration that corresponds indeed to decrease in pentasaccharide bound natural antithrombin concentration (FIG. 7). AT-N135Q-R393H(SEQ ID NO: 14) or AT-N135Q-Pro394 (SEQ ID NO: 16) at concentration equal to plasmatic antithrombin concentration is able to significantly decrease anti-factor Xa activity to a level comparable to curative pentasaccharide treatment (from 3 µg/mL to virtually 1.04 µg or 1.16 µg/mL, respectively). When AT-N135Q-R393H(SEQ ID NO: 14) is tested in 2 or 4 fold molar excess compared to natural antithrombin, virtual pentasaccharide concentration decreases to 0.49 or 0.29 µg/mL respectively (0.59 or 0.36 respectively with AT-N135Q-Pro394 (SEQ ID NO: 16)).

To estimate whether monomutated antithrombin can be used as reversal of pentasaccharide in case of over-dosing, AT-Pro394 (SEQ ID NO: 6) is tested in Rotachrom® heparin assay for its ability to restore factor Xa activity. AT-Pro394 (SEQ ID NO: 6) treatment is performed under the same conditions as for AT-N135Q-R393H(SEQ ID NO: 14) and AT-N135Q-Pro394 (SEQ ID NO: 16) when mimicking a pentasaccharide over-dosing. AT-Pro394 (SEQ ID NO: 6) at concentration equal to plasmatic antithrombin concentration is able to significantly decrease anti-factor Xa activity. When AT-Pro394 (SEQ ID NO: 6) is tested in 2 or 4 fold molar excess compared to natural antithrombin, virtual pentasaccharide concentration decreases to a level comparable to curative pentasaccharide treatment.

To evaluate the role of blood-vessel endothelium, or more precisely, the role of glycosamino-glycans exposed on endothelial cell surface, on competition between natural antithrombin and mutated antithrombin for pentasaccharide binding, the same experiment as described above is done but with pre-incubation of pentasaccharide containing plasma-mutated antithrombin mixture on HUVEC surface (FIG. 8). Pre-incubation on cell surface slightly influences effect of mutated antithrombin as reversal for pentasaccharide in case of over-dosing since in a ratio 1/1, 2/1, and 4/1 compared to plasma antithrombin concentration, AT-N135Q-R393H(SEQ ID NO: 14) decreases anti-factor Xa activity from 3 μg/mL of pentasaccharide to virtually 1.66, 0.91 and 0.26 μg/mL respectively (compared to 1.04, 0.49 and 0.29 μg/mL in the absence of endothelial cell during pre-incubation). In the same conditions AT-N135Q-Pro394 (SEQ ID NO: 16) decreases anti-factor Xa activity from 3 μg/mL of pentasaccharide to virtually 1.69, 0.94 and 0.27 μg/mL, respectively (compared to 1.16, 0.59 and 0.36 μg/mL in the absence of endothelial cell during pre-incubation).

Similarly, the same experiment as described above to evaluate the role of blood-vessel endothelium on competition between natural antithrombin and monomutated antithrombin for pentasaccharide binding is done, with pre-incubation of pentasaccharide containing plasma-monomutated antithrombin mixture on HUVEC surface. In the same conditions, pre-incubation on cell surface slightly influences effect of monomutated antithrombin as reversal for pentasaccharide in case of over-dosing, and AT-Pro394 (SEQ ID NO: 6) decreases anti-factor Xa activity of pentasaccharide.

This ex-vivo competition experiment, strongly suggests that monomutated and mutated antithrombin can be used as reversal for pentasaccharide at a dose equal to plasma antithrombin in case of moderate over-dosing. A four molar excess of mutated antithrombin decreases about 10 times (or more) initial pentasaccharide concentration and is still compatible with therapeutic use in case of severe over-dosing.

c) Example of Anti Factor Xa Inhibitory Activity of the Mutated Antithrombins in Mouse Plasma During the animal experimentation (see detailed protocol below), human mutated antithrombins compete with murine antithrombin for their binding to the pentasaccharide. Thus, preliminary in vitro assays are performed to determine the human mutated antithrombin concentration necessary to compete with the murine antithrombin present in mouse plasma supplemented with Fondaparinux.

These experiments are performed as described in section II-b, using mouse plasma instead of human plasma.

It is demonstrated that the mutated antithrombins compete with plasma antithrombin for pentasaccharide binding and are able to decrease significantly the plasma anti-Xa activity.

In the condition of the assay, addition of AT-R393H (SEQ ID NO: 4), AT-Pro394 (SEQ ID NO: 6), AT-ΔR393-5394 (SEQ ID NO: 18), AT-ΔR393 (SEQ ID NO: 8), AT-ΔS394 (SEQ ID NO: 10), AT-N135Q-R393H(SEQ ID NO: 14), AT-N135Q-Pro394 (SEQ ID NO: 16), AT-N135Q-ΔR393-S394 (SEQ ID NO: 24), AT-N135Q-ΔR393 (SEQ ID NO: 20), AT-N135Q-A5394 (SEQ ID NO: 22) produces a significant decrease in anti-Xa activity of a pentasaccharide contained in mouse plasma.

It is demonstrated that mutated antithrombins compete with plasma antithrombin for pentasaccharide binding in human plasma and in mouse plasma. The amount of human mutated antithrombins required to compete with mouse antithrombins is equal or more important.

III/In Vivo Characterization of the Mutated Antithrombins

The efficiency of the mutated antithrombins AT-R393H (SEQ ID NO: 4), AT-Pro394 (SEQ ID NO: 6), AT-ΔR393-S394 (SEQ ID NO: 18), AT-ΔR393 (SEQ ID NO: 8), AT-ΔS394 (SEQ ID NO: 10), AT-N135Q-R393H(SEQ ID NO: 14), AT-N135Q-Pro394 (SEQ ID NO: 16), AT-N135Q-ΔR393-S394 (SEQ ID NO: 24), AT-N135Q-ΔR393 (SEQ ID NO: 20), AT-N135Q-A5394 (SEQ ID NO: 22) as antidotes is evaluated in a murine model.

a) Animals

Animals (mice CF, males adults; or swiss mice, female adults (JANVIER)) are anesthetized using a protocol that does not modify the coagulation parameters, and in accordance with the European guidelines for animal experimentation.

The different drugs to be tested (fondaparinux, low molecular weight heparin, full length heparin and the mutated antithrombins) are administrated by intra-venous injection in the caudal vein to avoid the variability encountered when administration is performed subcutaneously. However, Heparin derivatives (fondaparinux, low molecular weight heparin and full length heparin) could also be administrated subcutaneously.

The blood is collected by punction in cave vein into tubes containing 0.105 mol/L trisodium citrate (1:10). Platelet-poor plasma is obtained by centrifugation at 2300 g for 10 minutes at 12° C. and stored at −80° C. until use.

b) Experimental Protocol

The following elements are determined:

the doses of fondaparinux inducing an overdose in mice, the mutated antithrombins time course, and in particular the time required to observe a maximal biological effect, the minimal doses of mutated antithrombins necessary to neutralize fondaparinux.

For each of these experiments, 4 groups of 5 mice each are used:

In the first group mice receive fondaparinux vehicle and then antidote (mutated antithrombin) vehicle.

In the second group, mice receive fondaparinux and then antidote vehicle

In the third group, mice receive fondaparinux vehicle and then antidote

In the last group, mice receive fondaparinux and then antidote

1—Determination of the Doses of Fondaparinux Inducing an Overdose in Mice Published data concerning fondaparinux pharmacokinetics in rats (Herbert J 4197), or experimental determination of fondaparinux pharmacokinetics in mice are used to develop the model.

In rat, fondaparinux has a maximal antithrombotic activity at doses of 100 nmol/kg (or 0.17 mg/kg).

Using this dose, the Cmax is 1.2±0.8 nmol/ml (or 2.1±1.4 mg/L). To induce an overdose, a 3 fold doses (300 nmol/kg, or 0.52 mg/kg) is tested. At this dose, the fondaparinux plasma concentration is about 3.5 to 4 nmol/ml (or 6 to 7 mg/L). An anti-Xa activity is determined to ensure that an overdose is obtained.

Anti FXa activity measurements is performed as previously described using a Stachrom Heparin® kit on a STA (Stago, France) or a Rotachrom Heparin® kit with procedure adapted for measurement in microplate reader (Dynatech MR 5000). A calibration curve with pentasaccharide is performed, allowing the expression of the results in nmol/ml (or in mg/L) of plasma.

2—Study of the Mutated Antithrombins Time of Action

In rats, fondaparinux has a Tmax of 5 min after intra-venous injection of 100 nmol/kg (or 0.17 mg/kg), or 30 min after subcutaneous injection of 100 nmol/kg (or 0.17 mg/kg).

In mouse, an overdose of fondaparinux is observed at 300 nmol/kg (or 0.52 mg/kg) but maximal concentration in plasma is observed less than 15 min after sub-cutaneous injection.

Thus, the antidote (mutated antithrombins) is administered intravenously, 5 min after the intra-venous injection of the fondaparinux, and 5, 15 or 30 min after the subcutaneous injection of the fondaparinux.

The mutated antithrombin time course is studied by measuring the plasma anti-Xa activity 5 min, 10 min, 20 min and 40 min after the antidote administration.

These experiments allow to determine the time of action of the antidote.

3—Determination of the Minimal Doses of Mutated Antithrombins Necessary for Fondaparinux Neutralization Once the time of action determined, a dose response curve is performed in vivo to determine the dose of antidote necessary to obtain a decrease in Fondaparinux plasma concentration within the therapeutic range around 1.2 nmol/ml (or 2 mg/L), or around 0.7 nmol/ml (or 1.2 mg/L).

Using these experimental conditions, injection of mutated antithrombins (AT-R393H(SEQ ID NO: 4), AT-Pro394 (SEQ ID NO: 6), AT-ΔR393-S394 (SEQ ID NO: 18), AT-ΔR393 (SEQ ID NO: 8), AT-ΔS394 (SEQ ID NO: 10), AT-N135Q-R393H(SEQ ID NO: 14), AT-N135Q-Pro394 (SEQ ID NO: 16), AT-N135Q-ΔR393-S394 (SEQ ID NO: 24), AT-N135Q-ΔR393 (SEQ ID NO: 20) or AT-N135Q-ΔS394 (SEQ ID NO: 22)), result in a significant decrease of the plasma anti FXa activity in mice treated with pentasaccharide.

The invention claimed is:

1. A method for inhibiting or treating coagulation disorders resulting from side effects of an anticoagulant selected from the group consisting of low molecular weight heparins, danaparoid sodium, fondaparinux and idraparinux, comprising administering to a person in need thereof a pharmaceutically effective amount of a mutated antithrombin having substantially no anticoagulant activity, wherein said mutated antithrombin is a non-wild type mutated antithrombin that differs from plasma antithrombin by having substantially lost factor Xa inhibitory activity and thrombin inhibitory activity and an increased affinity for the anticoagulant so that said mutated antithrombin is able to bind to the anticoagulant and to shift, including in vivo, the binding between plasma antithrombin and anticoagulant, and wherein said mutated antithrombin comprises, referring to amino acid numbering of the plasma antithrombin amino acid sequence represented by SEQ ID NO: 2:

at least one mutation within the region from the amino acid at position 380 to the amino acid at position 400 to provide a substantial loss of factor Xa inhibitory activity and thrombin inhibitory activity, said mutation being selected from the group consisting of an insertion between the amino acids at positions 393 and 394, a deletion of the amino acid at position 393, a deletion of the amino acid at position 394, and a deletion of the amino acids at positions 393 and 394, said mutation and at least one mutation at the glycosylation sites at the amino acid at position 96, 135, 155 or 192 to provide a loss of glycosylation and an increase in affinity for the anticoagulant compared to the amino acid sequence represented by SEQ ID NO: 2.

2. The method according to claim 1, wherein said mutated antithrombin is in association with a mutant of antithrombin, the amino acid sequence of which differs from that of said mutated antithrombin, wherein said mutated antithrombin has the ability to shift, including in vivo, the binding between plasma antithrombin and said anticoagulant and the ability to shift, including in vivo, the binding between said mutant of antithrombin and said anticoagulant.

3. The method according to claim 1, wherein the value of the dissociation equilibrium constant (Kd) of the complex resulting from the binding of said mutated antithrombin with said anticoagulant, at physiological ionic strength, is similar or lower than the value of the Kd of the complex between the amino acid sequence represented by SEQ ID NO: 2 and said anticoagulant.

4. The method according to claim 2, wherein the value of the Kd of the complex resulting from the binding of said mutated antithrombin with said anticoagulant, at physiological ionic strength, is similar or lower than the value of the Kd of the complex between said mutant of antithrombin and said anticoagulant.

5. The method according to claim 1, wherein the anticoagulant is selected from the group consisting of fondaparinux and idraparinux.

6. The method according to claim 1, wherein said at least one mutation within the region from the amino acid at position 380 to the amino acid at position 400 includes a deletion of the amino acid at position 394.

7. The method according to claim 1, wherein said at least one mutation within the region from the amino acid at position 380 to the amino acid at position 400 includes a deletion of the amino acid at position 393.

8. The method according to claim 1, wherein said at least one mutation at a glycosylation site includes a mutation at the glycosylation sites at the amino acid at position 135.

9. The method according to claim 1, wherein said mutated antithrombin is an amino acid sequence selected from the group consisting of:

SEQ ID NO:16, said amino acid sequence comprising, in the sequence of antithrombin represented by SEQ ID NO:2, the insertion of a Proline (Pro) between the amino acid at position 393 and the amino acid at position 394, and the substitution of the amino acid at position 135, by a Glutamine (Gln), SEQ ID NO:20, said amino acid sequence comprising, in the sequence of antithrombin represented by SEQ ID NO:2, the deletion of the amino acid at position 393 and the substitution of the amino acid at position 135, by a Glutamine (Gln), SEQ ID NO:22, said amino acid sequence comprising, in the sequence of antithrombin represented by SEQ ID NO:2, the deletion of the amino acid at position 394 and the substitution of the amino acid at position 135, by a Glutamine (Gln), and SEQ ID NO:24, said amino acid sequence comprising, in the sequence of antithrombin represented by SEQ ID NO:2, the deletion of the amino acid at position 393 and at position 394, and the substitution of the amino acid at position 135, by a Glutamine (Gln).

10. A method for inhibiting or treating coagulation disorders resulting from side effects of an anticoagulant selected from the group of low molecular weight heparins, danaparoid sodium, fondaparinux and idraparinux, comprising administering to a person in need thereof a pharmaceutically effective amount of a mutated antithrombin having substantially no anticoagulant activity, wherein, said mutated antithrombin is a non-wild type mutated antithrombin that differs from plasma antithrombin by having substantially lost factor Xa inhibitory activity and thrombin inhibitory activity and an increased affinity for the anticoagulant so that said mutated antithrombin is able to bind to the anticoagulant and to shift, including in vivo, the binding between plasma antithrombin and anticoagulant, and wherein said mutated antithrombin comprises, referring to amino acid numbering of the plasma antithrombin amino acid sequence comprising the signal peptide, represented by SEQ ID NO: 26:

at least one mutation within the region from the amino acid at position 412 to the amino acid at position 432 to provide a substantial loss of factor Xa inhibitory activity and thrombin inhibitory activity, said mutation being selected from the group consisting of an insertion between the amino acids at positions 425 and 426, a deletion of the amino acid at position 425, a deletion of the amino acid at position 426, and a deletion of the amino acids at positions 425 and 426, said mutation and at least one mutation at the glycosylation sites at the amino acid at position 128, 167, 187 or 224 to provide a loss of glycosylation and an increase in affinity for the anticoagulant compared to the amino acid sequence represented by SEQ ID NO: 26.

11. The method according to claim 10, wherein said mutated antithrombin comprises a mutation at the amino acid at position 425.

12. The method according to claim 10, wherein said mutated antithrombin further comprises a mutation at the glycosylation sites at the amino acid at position 167.

13. The method according to claim 10, wherein said mutated antithrombin is an amino acid sequence selected from the group consisting of:

SEQ ID NO:28, said amino acid sequence comprising, in the sequence of antithrombin represented by SEQ ID NO:26, the substitution of the amino acid at position 425, by an Histidine (His), SEQ ID NO:30, said amino acid sequence comprising, in the sequence of antithrombin represented by SEQ ID NO:26, the insertion of a Proline (Pro) between the amino acid at position 425 and the amino acid at position 426, SEQ ID NO:32, said amino acid sequence comprising, in the sequence of antithrombin represented by SEQ ID NO:26, the deletion of the amino acid at position 425, and SEQ ID NO:34, said amino acid sequence comprising, in the sequence of antithrombin represented by SEQ ID NO:26, the deletion of the amino acid at position 426.

14. The method according to claim 10, wherein said mutated antithrombin is an amino acid sequence selected from the group consisting of:

SEQ ID NO:38, said amino acid sequence comprising in the sequence of antithrombin represented by SEQ ID NO:26, the substitution of the amino acid at position 425, by an Histidine (His), and the substitution of the amino acid at position 167, by a Glutamine (Gln), SEQ ID NO:40, said amino acid sequence comprising, in the sequence of antithrombin represented by SEQ ID NO:26, the insertion of a Proline (Pro) between the amino acid at position 425 and the amino acid at position 426, and the substitution of the amino acid at position 167, by a Glutamine (Gln), SEQ ID NO:44, said amino acid sequence comprising, in the sequence of antithrombin represented by SEQ ID NO:26, the deletion of the amino acid at position 425 and the substitution of the amino acid at position 167, by a Glutamine (Gln), SEQ ID NO:46, said amino acid sequence comprising, in the sequence of antithrombin represented by SEQ ID NO:26, the deletion of the amino acid at position 426 and the substitution of the amino acid at position 167, by a Glutamine (Gln), and SEQ ID NO:48, said amino acid sequence comprising, in the sequence of antithrombin represented by SEQ ID NO:26, the deletion of the amino acid at position 425 and at position 426 and the substitution of the amino acid at position 167, by a Glutamine (Gln).

15. A method for inhibiting or treating coagulation disorders resulting from side effects of an anticoagulant selected from the group consisting of low molecular weight heparins, danaparoid sodium, fondaparinux and idraparinux, comprising administering to a person in need thereof a pharmaceutically effective amount of a mutated antithrombin having substantially no anticoagulant activity, wherein said mutated antithrombin is a non-wild type mutated antithrombin that differs from plasma antithrombin by having substantially lost factor Xa inhibitory activity and thrombin inhibitory activity and an increased affinity for the anticoagulant so that said mutated antithrombin is able to bind to the anticoagulant and to shift, including in vivo, the binding between plasma antithrombin and anticoagulant, and wherein said mutated antithrombin is represented by SEQ ID NO: 18, which comprises, referring to amino acid numbering of the plasma antithrombin amino acid sequence represented by SEQ ID NO: 2:

the deletion of the amino acid at position 393 and at position 394, and at least one mutation at the glycosylation sites at the amino acid at position 96, 135, 155 or 192 to provide a loss of glycosylation and an increase in affinity for the anticoagulant compared to the amino acid sequence represented by SEQ ID NO: 2.

16. A method for inhibiting or treating coagulation disorders resulting from side effects of an anticoagulant selected from the group consisting of low molecular weight heparins, danaparoid sodium, fondaparinux and idraparinux, comprising administering to a person in need thereof a pharmaceutically effective amount of a mutated antithrombin having substantially no anticoagulant activity, wherein, said mutated antithrombin is a non-wild type mutated antithrombin that differs from plasma antithrombin by having substantially lost factor Xa inhibitory activity and thrombin inhibitory activity and an increased affinity for the anticoagulant so that said mutated antithrombin is able to bind to the anticoagulant and to shift, including in vivo, the binding between plasma antithrombin and anticoagulant, and wherein said mutated antithrombin is represented by SEQ ID NO: 42, which comprises, referring to amino acid numbering of the plasma antithrombin amino acid sequence comprising the signal peptide, represented by SEQ ID NO: 26:

the deletion of the amino acid at position 425 and at position 426, and at least one mutation at the glycosylation sites at the amino acid at position 128, 167, 187 or 224 to provide a loss of glycosylation and an increase in affinity for the anticoagulant compared to the amino acid sequence represented by SEQ ID NO: 26.

* * * * *